US012576010B2

(12) United States Patent
Hernandez et al.

(10) Patent No.: US 12,576,010 B2
(45) **Date of Patent: *Mar. 17, 2026**

(54) MEDICINE DISPENSING SYSTEM HAVING STAIR-STEP DOSING INDICATORS

(71) Applicant: CD Acquisitions, LLC, Denver, CO (US)

(72) Inventors: Caleb Hernandez, Denver, CO (US); Daniel Hoffman, New York, NY (US)

(73) Assignee: CD Acquisitions, LLC, Denver, CO (US)

( * ) Notice: Subject to any disclaimer, the term of this patent is extended or adjusted under 35 U.S.C. 154(b) by 155 days.

This patent is subject to a terminal disclaimer.

(21) Appl. No.: 18/107,347

(22) Filed: Feb. 8, 2023

(65) Prior Publication Data

US 2023/0218482 A1 Jul. 13, 2023

Related U.S. Application Data

(63) Continuation of application No. 16/841,483, filed on Apr. 6, 2020, now Pat. No. 11,583,475.

(Continued)

(51) Int. Cl.
*A61J 7/00* (2006.01)
*A61B 5/107* (2006.01)
(Continued)

(52) U.S. Cl.
CPC ........... *A61J 7/0076* (2013.01); *A61J 7/0023* (2013.01); *A61J 7/0046* (2013.01); *A61J 7/0053* (2013.01);
(Continued)

(58) Field of Classification Search
CPC ...... A61J 7/0076; A61J 7/0023; A61J 7/0046; A61J 7/0053; A61J 2205/20; A61J 1/065; A61J 2200/76; G01F 11/006; G01F 11/027; A61B 5/1072; A61M 5/178; A61M 2005/3126
See application file for complete search history.

(56) References Cited

U.S. PATENT DOCUMENTS

| 2,888,015 A | 5/1959 | Hunt |
| 4,716,888 A | 1/1988 | Wesner |
| (Continued) | | |

FOREIGN PATENT DOCUMENTS

| WO | 199101710 A1 | 2/1991 |
| WO | 2020072549 A1 | 4/2020 |

OTHER PUBLICATIONS

Lee Young, "International Search Report and Written Opinion Regarding International Application No. PCT/US20/26927", Jul. 9, 2020, p. 10, Published in: US.

(Continued)

*Primary Examiner* — Frederick C Nicolas
(74) *Attorney, Agent, or Firm* — NOD Law PC

(57) ABSTRACT

A medicine dispensing device, configured to contain a liquid medicine to be dispensed by the medicine dispensing device and having a plurality of dosing indicia spaced apart from each other around and in relation to a circumference of a surface of the medicine dispensing device, each dosing indicia being of a different height relative to a reference level and corresponding to different dose of the liquid medicine.

20 Claims, 58 Drawing Sheets

Related U.S. Application Data

(60) Provisional application No. 62/830,287, filed on Apr. 5, 2019.

(51) Int. Cl.

| | |
|---|---|
| *A61J 1/06* | (2006.01) |
| *A61M 5/178* | (2006.01) |
| *A61M 5/31* | (2006.01) |
| *G01F 11/00* | (2006.01) |
| *G01F 11/02* | (2006.01) |

(52) U.S. Cl.

CPC .......... *A61M 5/178* (2013.01); *G01F 11/006* (2013.01); *G01F 11/027* (2013.01); *A61B 5/1072* (2013.01); *A61J 1/065* (2013.01); *A61J 2200/76* (2013.01); *A61J 2205/20* (2013.01); *A61M 2005/3126* (2013.01)

(56) References Cited

U.S. PATENT DOCUMENTS

| | | | | |
|---|---|---|---|---|
| 5,010,656 | A | 4/1991 | Broselow | |
| 5,495,854 | A | 3/1996 | Currie | |
| 5,699,937 | A | 12/1997 | Canela | |
| 6,132,416 | A | 10/2000 | Broselow | |
| 6,769,302 | B1 | 8/2004 | King et al. | |
| 6,904,867 | B2 * | 6/2005 | Zamjahn | G09F 11/23 |
| | | | | 141/381 |
| 9,828,140 | B1 | 11/2017 | Molina | |
| 10,632,263 | B2 | 4/2020 | Lockhart et al. | |
| 11,583,475 | B2 | 2/2023 | Hernandez et al. | |
| 2002/0029635 | A1 | 3/2002 | Kremen | |
| 2007/0135772 | A1 | 6/2007 | Grogan, Jr. | |
| 2007/0214692 | A1 | 9/2007 | Ferrara | |
| 2008/0067191 | A1 | 3/2008 | Ferrara | |
| 2008/0178637 | A1 | 7/2008 | Etesse et al. | |
| 2014/0027502 | A1 | 1/2014 | Schwartz | |
| 2015/0094650 | A1 | 4/2015 | Young | |
| 2016/0067143 | A1 | 3/2016 | Ferrara | |
| 2016/0166776 | A1 | 6/2016 | Appelbaum | |
| 2017/0151391 | A1 | 6/2017 | Hernandez | |
| 2018/0140509 | A1 | 5/2018 | Grogan, Jr. | |
| 2020/0397660 | A1 | 12/2020 | Hernandez et al. | |

OTHER PUBLICATIONS

Med Alliance Group, "Certa Dose Pals Syringe Holder Kit Video V 18", Retrieved from https://www.youtube.com/watch?v=fW8PRxXIT-I, Dec. 5, 2018, p. 2.

Nicolas, Frederick, "Office Action Issued in U.S. Appl. No. 16/841,483", May 18, 2022, Published in: US.

Nicolas, Frederick, "Office Action Issued in U.S. Appl. No. 16/841,483", Sep. 15, 2021, Published in: US.

"First Office Action", issued in corresponding Chinese Patent Application No. 202080041345.5, filed Dec. 3, 2021 (English translation provided).

"Second Office Action", issued in corresponding Chinese Patent Application No. 202080041345.5, filed Dec. 3, 2021 (English translation provided).

* cited by examiner

400

SELECT MEDICATION TO BE
ADMINISTERED — 401

DETERMINE DRUG DOSES FOR EACH
OF THE COLOR CODED LENGTH
ZONES FOR THE SELECTED
MEDICATION — 402

DETERMINE SOLUTION
CONCENTRATION OF THE
MEDICATION — 403

DETERMINE VOLUMETRIC CAPACITY
OF THE MEDICINE DISPENSING
DEVICE — 404

CALCULATE INDIVIDUAL AND TOTAL
COLOR BAND OR ZONE WIDTHS. — 405

500

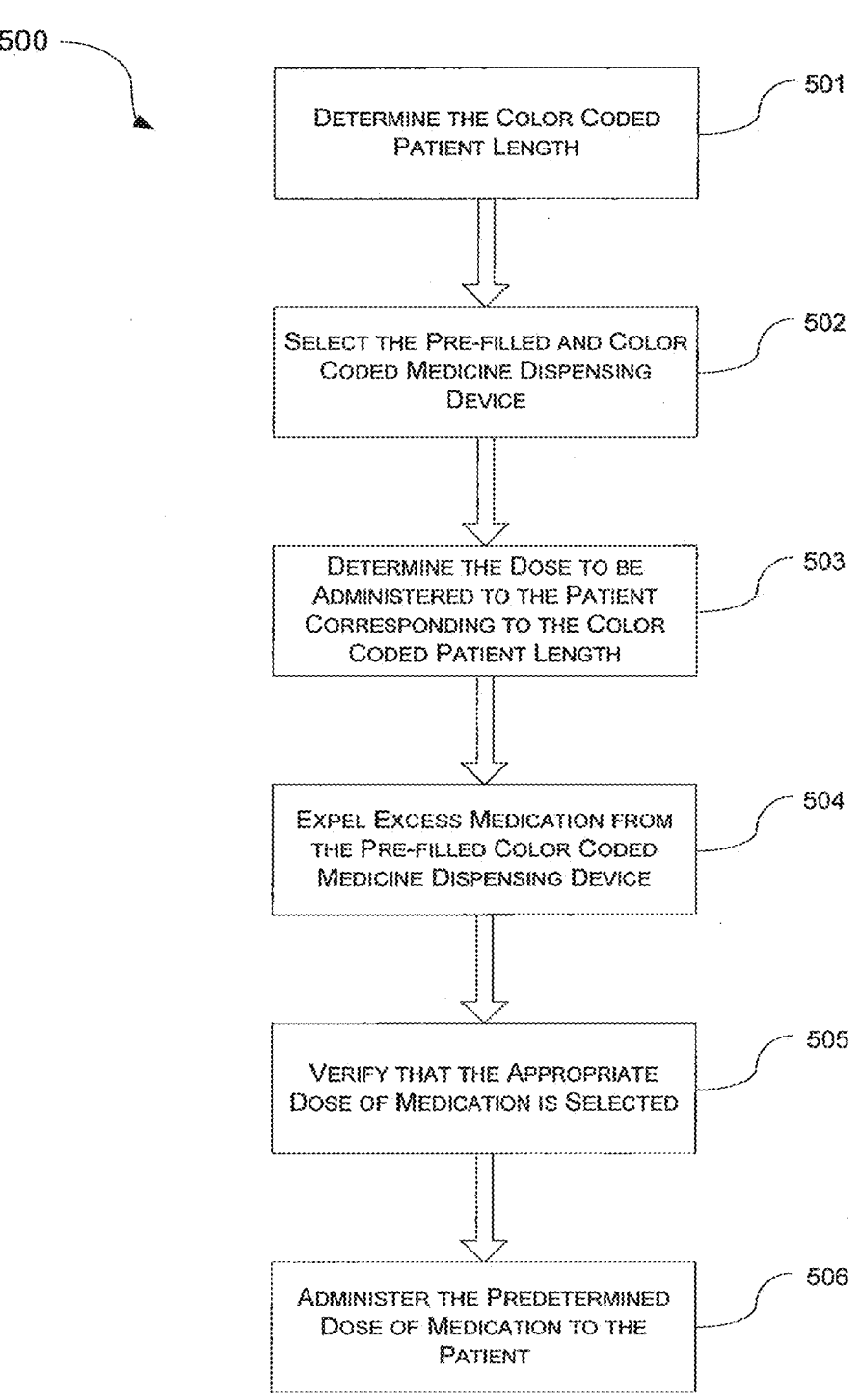

501
DETERMINE THE COLOR CODED
PATIENT LENGTH

502
SELECT THE PRE-FILLED AND COLOR
CODED MEDICINE DISPENSING
DEVICE

503
DETERMINE THE DOSE TO BE
ADMINISTERED TO THE PATIENT
CORRESPONDING TO THE COLOR
CODED PATIENT LENGTH

504
EXPEL EXCESS MEDICATION FROM
THE PRE-FILLED COLOR CODED
MEDICINE DISPENSING DEVICE

505
VERIFY THAT THE APPROPRIATE
DOSE OF MEDICATION IS SELECTED

506
ADMINISTER THE PREDETERMINED
DOSE OF MEDICATION TO THE
PATIENT

FIG. 5

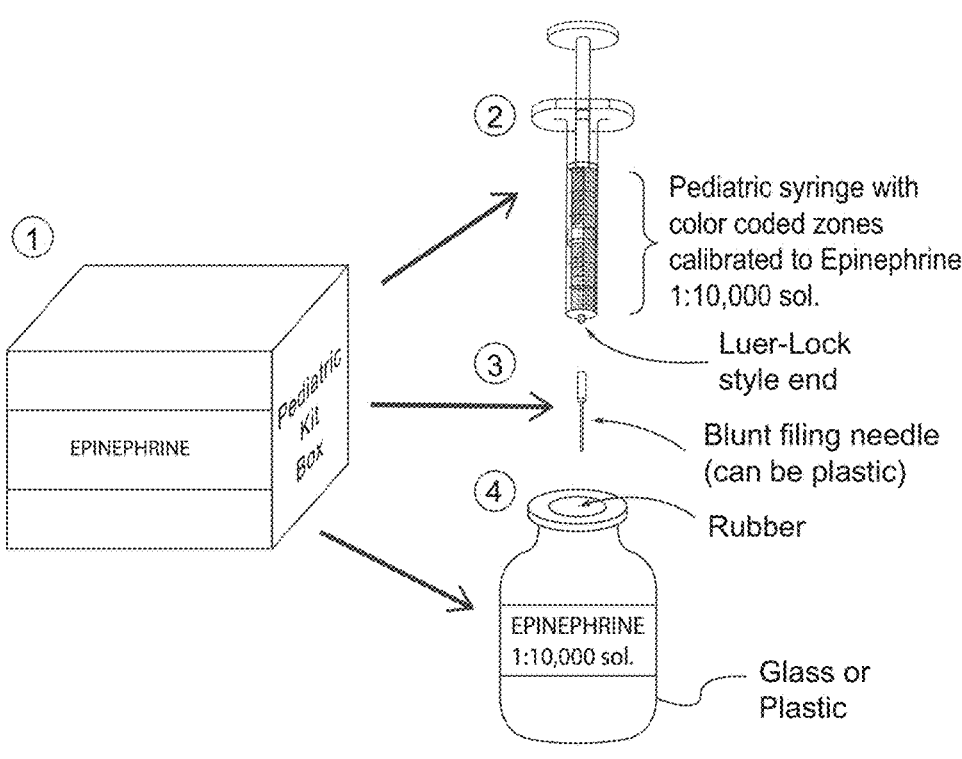
Pediatric syringe with color coded zones calibrated to Epinephrine 1:10,000 sol.
Luer-Lock style end
Blunt filing needle (can be plastic)
Rubber
Glass or Plastic
Steps
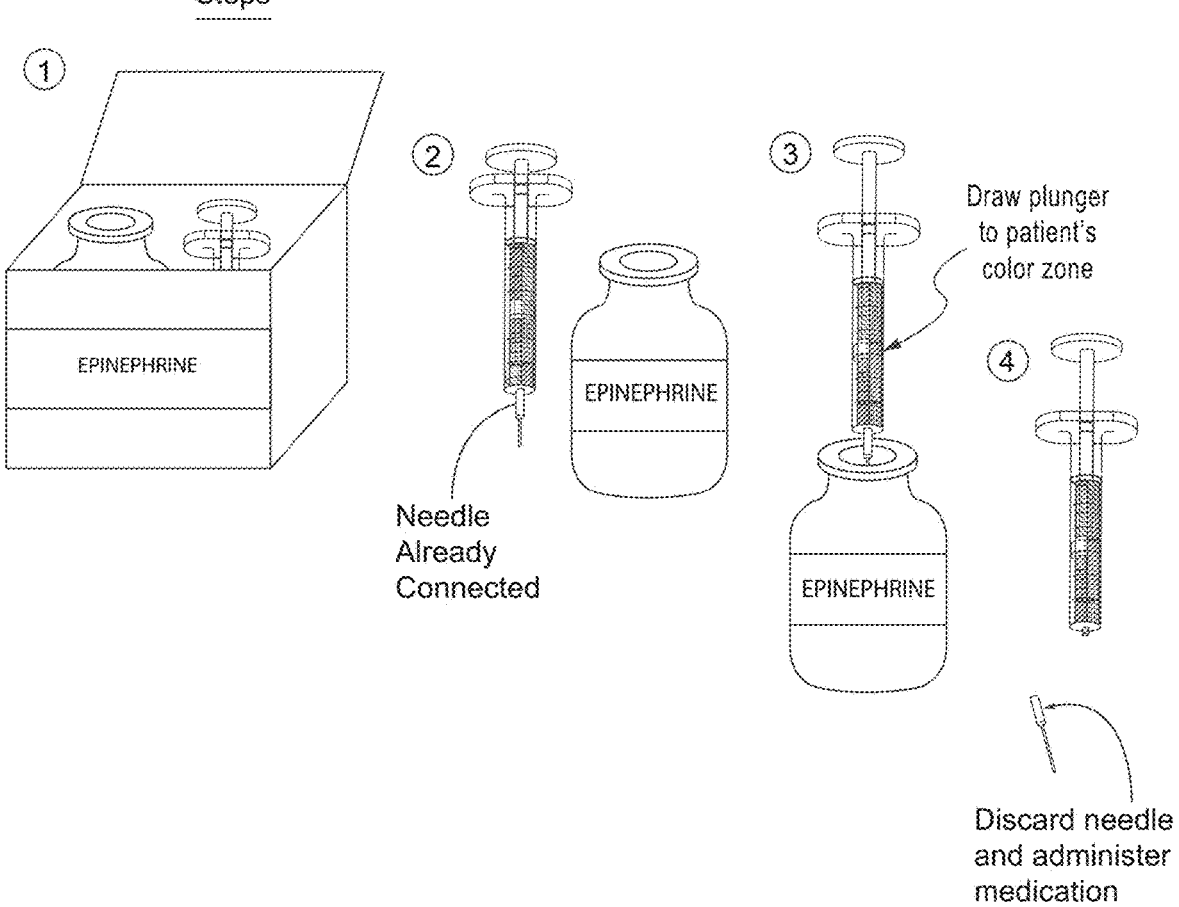
Needle Already Connected
Draw plunger to patient's color zone
Discard needle and administer medication
FIG. 7

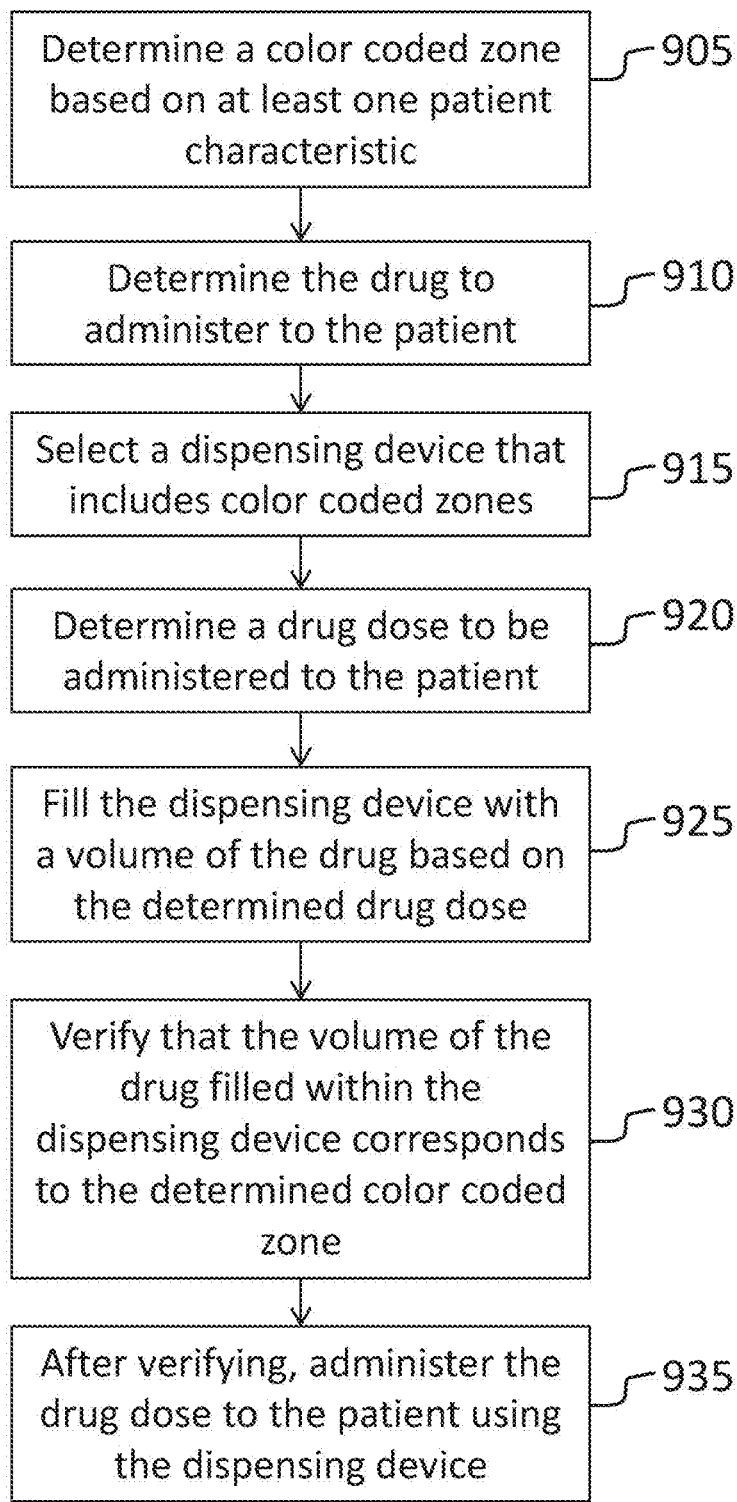

Determine a color coded zone based on at least one patient characteristic — 905

Determine the drug to administer to the patient — 910

Select a dispensing device that includes color coded zones — 915

Determine a drug dose to be administered to the patient — 920

Fill the dispensing device with a volume of the drug based on the determined drug dose — 925

Verify that the volume of the drug filled within the dispensing device corresponds to the determined color coded zone — 930

After verifying, administer the drug dose to the patient using the dispensing device — 935

FIGURE 9A

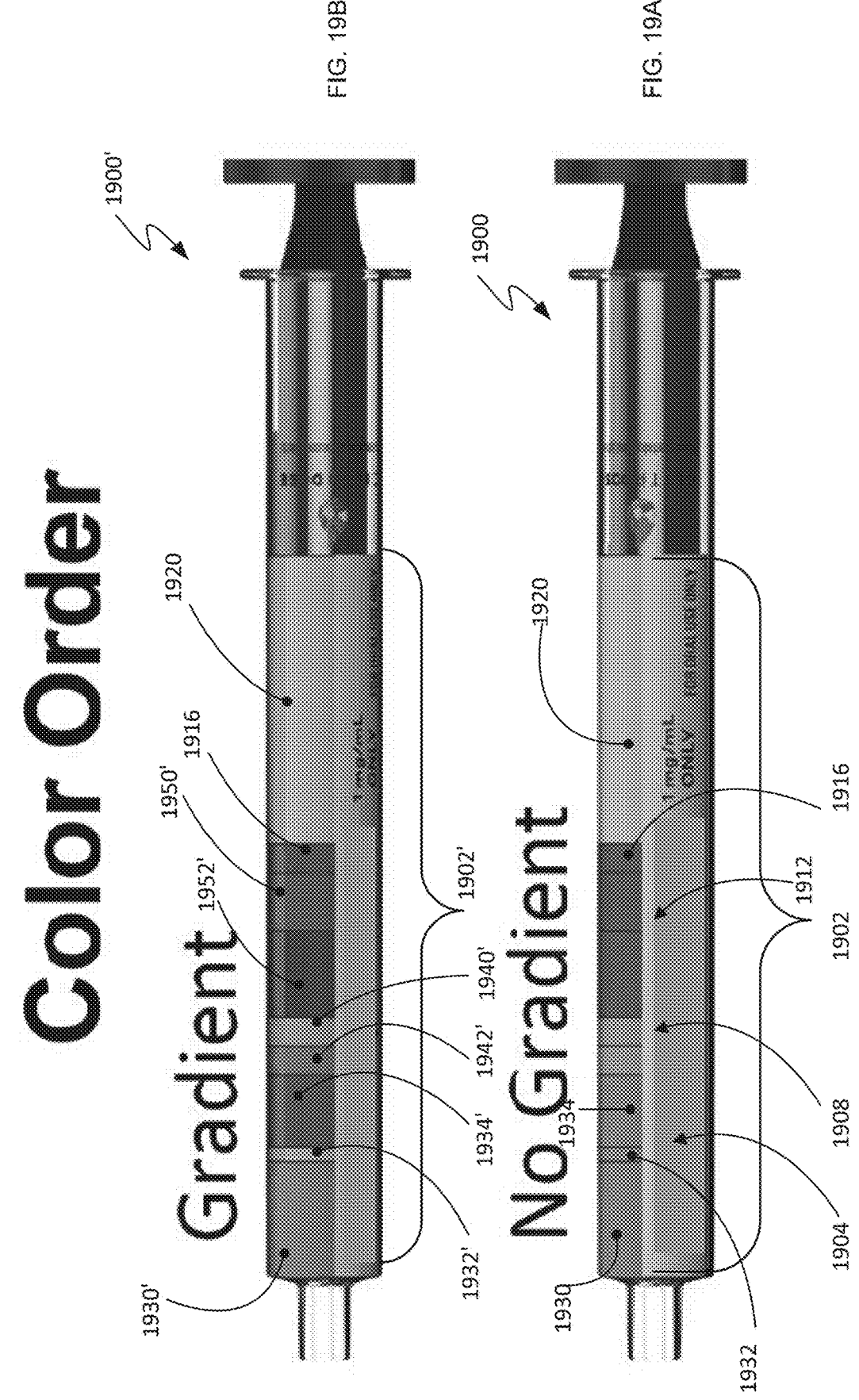

2400

2410

| DRUG 1 / CONDITION 1 | |
| --- | --- |
| ZONE COLOR | DOSE (mg or mL) |
| | |
| | 1.1 |
| | 1.6 |
| | 1.7 |
| | 2 |
| | 2.5 |

| DRUG 1 / CONDITION 2 | |
| --- | --- |
| ZONE COLOR | DOSE (mg or mL) |
| | |
| | 0.8 |
| | 0.9 |
| | 1.4 |
| | 1.6 |
| | 1.8 |
| | 2.4 |
| | 2.8 |
| | 3 |
| | 5 |

2700

| Your Child | DRUG XYZ | |
|---|---|---|
| Select Dose | COLOR | DOSE [mg or mL] |
| ☐ | A | 0.8 |
| ☐ | B | 0.9 |
| ☐ | C | 1.1 |
| ☐ | D | 1.4 |
| ☐ | E | 1.6 |
| ☐ | F | 1.7 |
| ☐ | G | 1.8 |
| ☐ | H | 2 |
| ☐ | I | 2.4 |
| ☐ | J | 2.5 |
| ☐ | K | 2.8 |
| ☐ | L | 3.0 |
| ☐ | M | 5.0 |

2710

2712

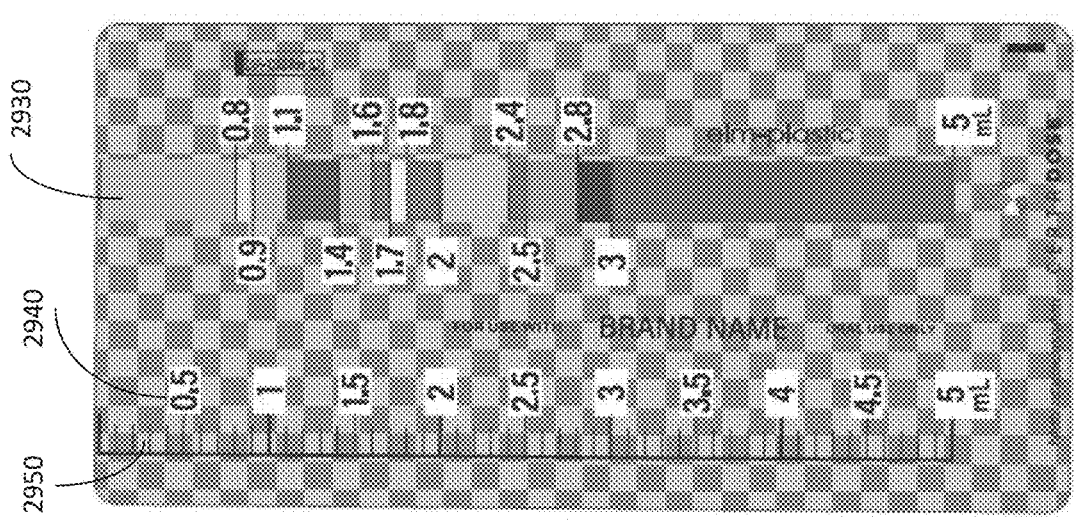
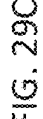
FIG. 29C
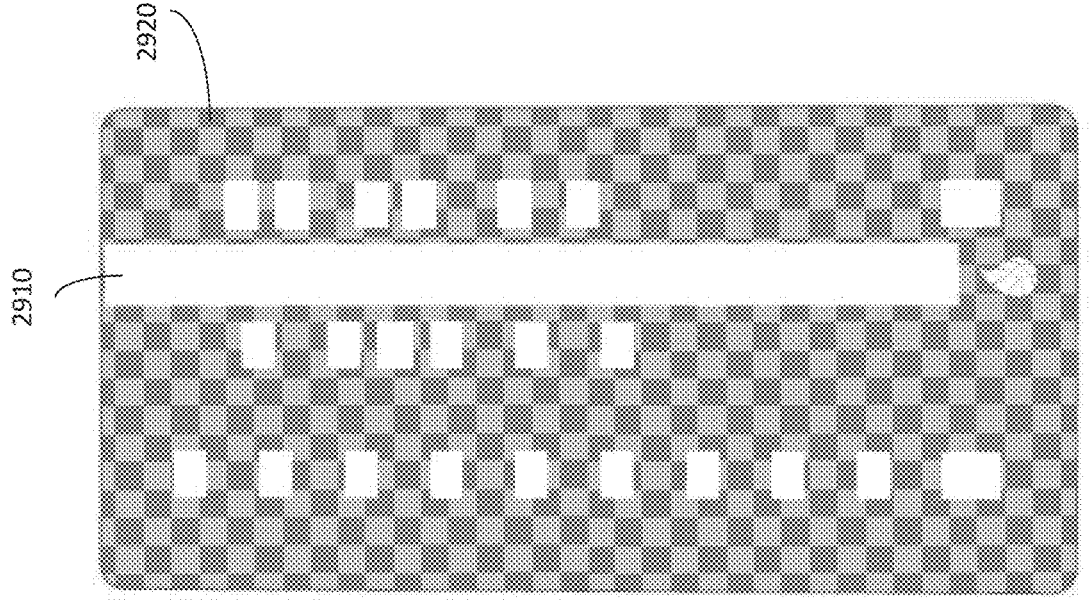
FIG. 29B

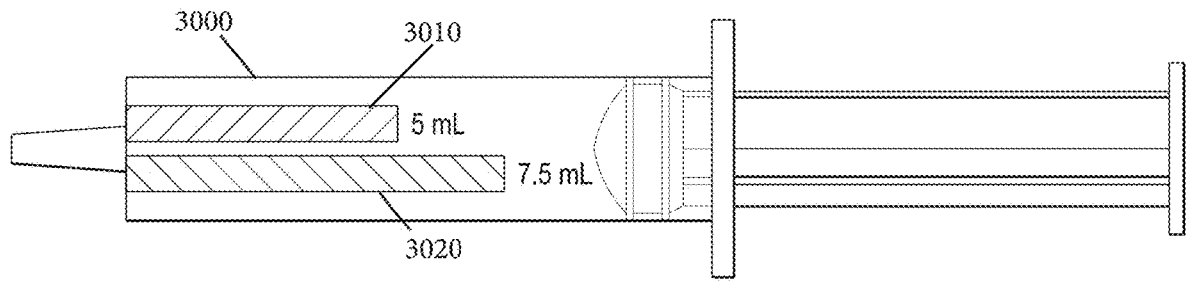
FIG. 30
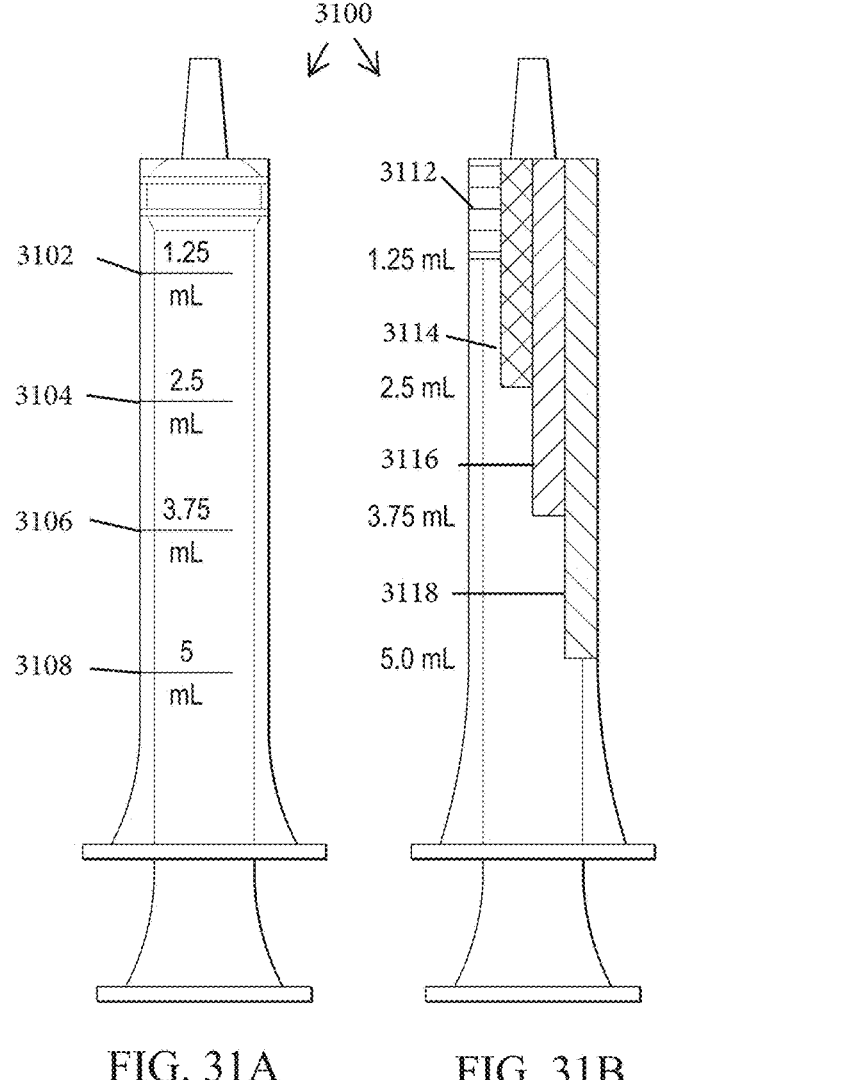
FIG. 31A           FIG. 31B

MEDICINE DISPENSING SYSTEM HAVING STAIR-STEP DOSING INDICATORS

PRIORITY

The present Application is a continuation of U.S. patent application Ser. No. 16/841,483 filed Apr. 6, 2020 entitled "MEDICINE DISPENSING SYSTEM HAVING STAIR-STEP DOSING INDICATORS" issuing as U.S. Pat. No. 11,583,475 on Feb. 21, 2023 which claims priority to Provisional Application No. 62/830,287, filed Apr. 5, 2019, entitled "MEDICINE DISPENSING SYSTEM HAVING STAIR-STEP DO SING INDICATORS" and are assigned to the assignee hereof and hereby expressly incorporated by reference herein.

FIELD OF DISCLOSURE

The present disclosure relates to a medicine-dosing device, and more particularly to a medicine dosing device having particularly arranged and designed dosing labels, and methods for administering appropriate doses of medicine thereby.

BACKGROUND

Administering proper drug doses accurately and efficiently during an emergency or intensive care situation is of critical importance. This is particularly of essence in an emergency or critical care situations, and especially those that involve pediatric patients as even small dosing mistakes can lead to disastrous consequences. However, even under the best of circumstances and despite the best of efforts of medical personnel, inadvertent mistakes are sometimes made because of the multitude of steps involved in the drug administration process. More specifically, in a typical situation appropriate drug dosage must first be determined, which usually involves multi-step mathematical calculations. This is followed by plurality of steps involved in the actual drug administration process, which may include selection of a correct medicine to be administered or medical dosing device to be used. Because each step carries with it a potential for introducing an error into the overall drug administration process, reducing the number of steps that must be executed can significantly increase the overall accuracy and efficiency of the process.

Drug dosages conventionally are determined based on the weight of the patient. However, this method can, at times, be inappropriate and inaccurate especially in the emergency and critical care situations. Thus, at times, patient length can be used, as it allows for a quick and efficient determination of drug dosages, involves the use of a color-coded measuring tape for determining the length of a patient. More specifically, the Broselow® Pediatric Emergency Tape is a well-known instrument that correlates easily obtainable patient length to drug dosages. The details of the instrument and the method of its use are disclosed in the U.S. Pat. Nos. 4,716,888 and 6,132,416 to Broselow which are incorporated by reference into the present disclosure. In general, the method involves measuring and coding patient length to one of the color zones provided on the tape and using the color-coded length to determine a drug dosage to be administered to the patient. By segmenting the tape into plurality of color coded zones rather than the typically used inches or centimeters, with each color zone corresponding to a given length range, the length of the patient can be easily read and noted as being of a certain color rather than as a specific measurement in centimeters or inches. In other words, each color-coded length zone corresponds to a certain, predetermined range of the actual lengths as measured in either metric or imperial units. For example, the grey color zone on the tape may correspond to a length range from 42.20 cm to 60.79 cm and the pink color zone on the tape may correspond to the length range from 60.80 cm to 67.79 cm.

Thus, a patient whose length falls within the first length range would be coded as gray and a patient whose length falls within the second length range would be coded as pink. The appropriate drug dosages for the two patients would then be selected from a list of predetermined drug dosages listed on the tape. Other commercially available length/weight-based tapes, such as the PediaTape and the Handtevy tape, are used in a similar fashion.

Although the step of determining drug dosages has been greatly simplified with the use of aforementioned method, a number of other issues still remain that often lead to dosing errors or that make the medication administration process inefficient. For instance, in order to arrive at a correct dose of medicine that is to be administered once the medication dosage is determined a number of other calculations, such as those involving, for example, concentration of the medication, still need to be performed. Furthermore, the selection of a correct medicine, an appropriate medicine dosing device or drawing of a correct predetermined volume of medication into the medicine dosing device can each introduce an error or slow down the process of administering medication to the patient. Even in situations when medication dosages are based on dosing systems other than the conventional weight based systems, such as for example patient age, body surface area or volume, dosing inaccuracies may be observed due to the type of calibrations used in such systems. In particular, a typically used constant incremental change in dosages may result in a loss in needed dosing accuracy when such systems are used.

Thus, despite the availability of various techniques designed to simplify the process of drug dosage determination and administration, there still exists a possibility of errors because of the pressure of time and the environment under which the treatment is delivered, as well as the type of dosing systems that are being used. Accordingly, there is need for a device for, and method of, accurately and efficiently delivering drugs, especially to pediatric patients.

SUMMARY

A medicine dispensing device for administering a liquid medicine is disclosed herein. The medicine dispensing device includes a cup configured to contain a liquid medicine to be dispensed by the medicine dispensing device. The cup includes a side wall, a circular bottom element and an open top.

The device further includes a plurality of dosing indicia spaced apart from each other around and in relation to a circumference of a surface of the side wall. Each dosing indicia is of a different height relative to a reference level and corresponds to a different dose of the liquid medicine.

In one implementation the plurality of dosing indicia are correlated to a plurality of values of a physical characteristic of a patient. Each of the plurality of dosing indicia may be of a different color. In addition, each of the plurality of dosing indicia may include a first portion of a first transparency and a second portion of a second transparency different from the first transparency. A first of the plurality of dosing indicia may be separated from a second of the plurality of dosing indicia by approximately 180 degrees on the surface of the side wall, which in one implementation is frustoconical. Each of the plurality of dosing indicia may further include a volumetric indication.

In another aspect the disclosure relates to a medicine dispensing device including a frustoconical cup configured to contain a liquid medicine to be dispensed. The device further includes a plurality of color-coded dosing indicia spaced apart from each other around and in relation to a circumference of a lateral surface of the frustoconical cup. Each dosing indicia is of a different height relative to a reference level and corresponds to a different dose of the liquid medicine.

In one implementation each dosing indication on the frustoconical cup further includes a volumetric indication. The reference level may be coincident with or proximate an interior bottom surface of the frustoconical cup. Each of the plurality of dosing indicia may include a first portion of a first transparency and a second portion of a second transparency different from the first transparency.

The disclosure is also directed to a medicine dispensing device including a syringe having a barrel configured to contain a liquid medicine to be dispensed by the medicine dispensing device. A plurality of color-coded dosing indicia are spaced around a circumference of a surface of the barrel. Each dosing indicia is of a different height relative to a reference level and corresponds to a different dose of the liquid medicine. The reference level may be proximate an end of the barrel.

In one implementation the dispensing device includes a syringe, and the plurality of color-coded dosing indicia are correlated to a plurality of values of a physical characteristic of a patient. Each of the plurality of dosing indicia may be of a different color. In addition, each of the plurality of dosing indicia may include a first portion of a first transparency and a second portion of a second transparency different from the first transparency. A first of the plurality of dosing indicia may be separated from a second of the plurality of dosing indicia by approximately 180 degrees on the surface of the barrel. Each of the plurality of dosing indicia may further be rectangular, of a different color, and include a volumetric indication.

In yet another aspect the disclosure is directed to a medicine dispensing device including a spoon configured to receive a liquid medicine to be dispensed. A plurality of color-coded dosing indicia are spaced apart from each other around and in relation to a portion of the spoon configured to hold the liquid medicine to be dispensed, each dosing indicia being of a different length relative to a reference and corresponding to different dose of the liquid medicine.

In one implementation, the dispensing device includes a spoon, and the plurality of dosing indicia are correlated to a plurality of values of a physical characteristic of a patient. Each of the plurality of dosing indicia may be of a different color. In addition, each of the plurality of dosing indicia may include a first portion of a first transparency and a second portion of a second transparency different from the first transparency. Each of the plurality of dosing indicia may further be rectangular, of a different color, and include a volumetric indication.

BRIEF DESCRIPTION OF THE DRAWINGS

FIG. 5 is flow diagram showing a method of administering a medication using the disclosed pre-filled and marked medicine-dosing device.

FIG. 7 illustrates an exemplary emergency medical treatment kit for administering a medication according to one embodiment of the current disclosure.

FIGS. 9A-9B illustrate alternative methods of administering a medication according to some embodiments.

FIGS. 13-17B depict a medicine dispensing device in the form of a syringe 1300 configured to deliver either or both of treatment dosages and prophylaxis dosages of a particular drug.

FIGS. 19A and 19B, and 20A and 20B depict a syringe having a series of multi-segment color-coded bands of varying widths.

FIGS. 29A-C show views of a label that may be printed to manufacture a medicine dispensing device of the present disclosure.

FIG. 30 illustrates an embodiment of a medicine dispensing device in the form of a syringe having two stair-stepped dosing indicators.

FIGS. 31A and 31B illustrate a front and back side of a medicine dispensing device in the form of syringe for administering a liquid medicine with a set of stair-step dosing indicia.

DETAILED DESCRIPTION

Figure 1A:
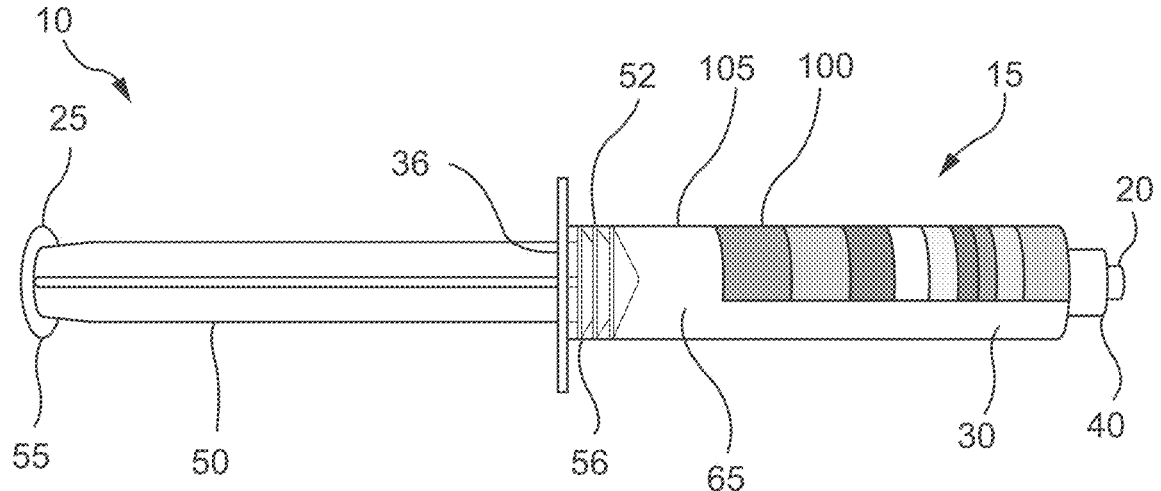
FIGS. 1A-1D are perspective views of a medicine-dosing device according to one embodiment of the current disclosure.

The present application describes a device, system, and a method for administering proper medication doses to patients. The device and system are configured to address the five "rights" of medicine delivery; that is, giving the right patient the right drug in the right dose by the right route at the right time. In particular, a pre-marked medicine dosing/dispensing device designed to minimize medication dosing errors, as well as to improve the overall accuracy and efficiency of administering medication, especially in the emergency and critical care situations, is provided.

As discussed in detail below, in one embodiment the medicine dosing device 10 is a syringe 15 that includes an elongate barrel 30 marked with predetermined color-coded volumetric medicine doses 100 and a plunger 50. The medicine-dosing device, according to one embodiment, may be further pre-filled with a fluid 105 that corresponds to a medication to be administered to a patient. A method for determining specific volumetric doses for a plurality of medications based on different factors is also disclosed. In particular, according to one embodiment the method involves generating labels or marking medical dosing devices with doses that are determined based on, for example, volumetric capacity of medical dosing device and/or drug concentration.

Also, a method for administering proper medication doses using the pre-marked medicine-dosing device is discussed. The method disclosed leads to a significant reduction in the amount of time required to determine and administer a dose of medication to a patient and at the same time decreases the risk that such doses will be miscalculated or otherwise erroneously administered.

Device

For a detailed discussion of the first embodiment of the pre-labeled medicine dosing/dispensing device 10, reference is now made to FIGS. 1A-1D. As shown in FIG. 1A, the medicine dosing device 10 according to one embodiment is a syringe 15 that includes a proximal end 25 and a distal end 20 opposite the proximal end. The syringe includes a vessel, such as a syringe barrel 30 at the distal end for holding therein a medicine that is to be dispensed, and a plunger 50 that extends proximally from an opening 36 located at the proximal end 35 of the syringe barrel to the proximal end 55 of the plunger at the proximal end 25. The syringe barrel and plunger are both manufactured from material such as plastic, glass or any other suitable transparent medical grade material that is inert or will not disrupt the chemical balance of the fluid inside.

Figure 1B:
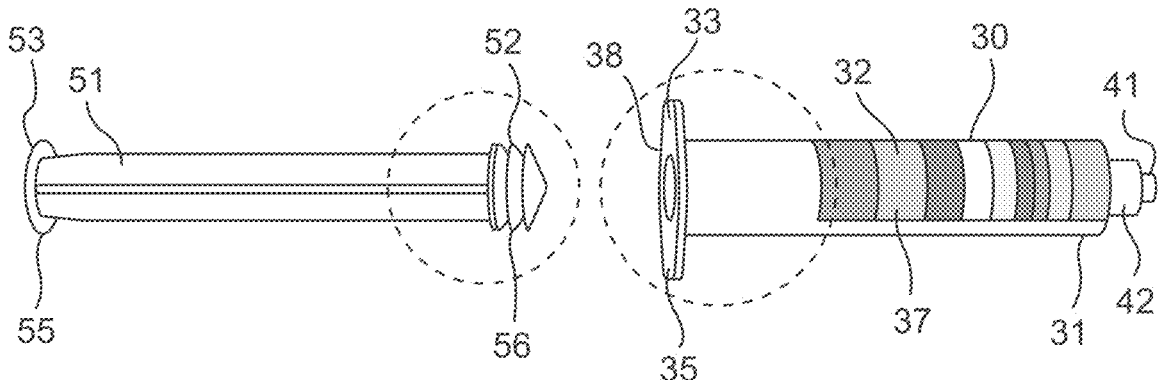
Figure 1C:
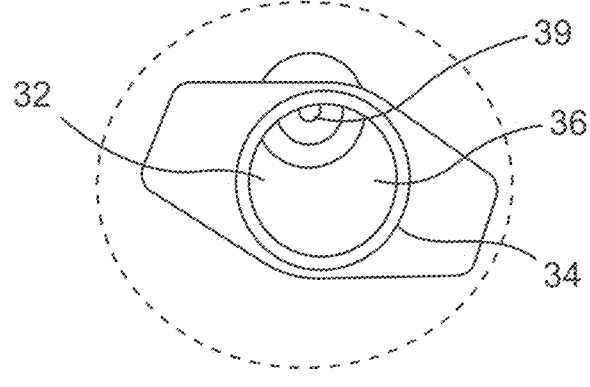
Figure 1D:
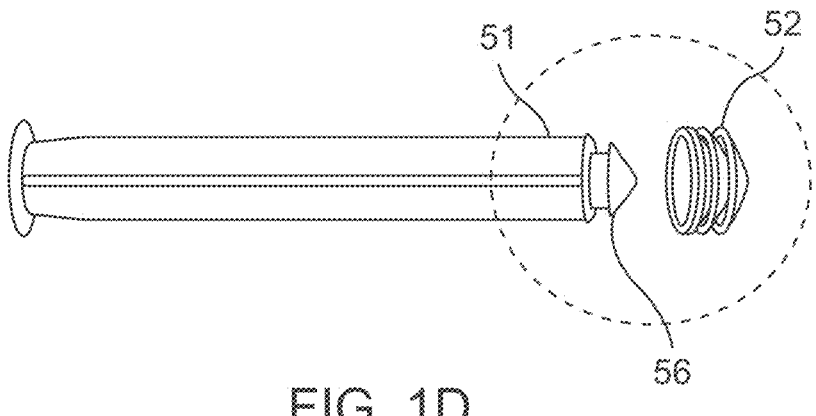

As illustrated in FIG. 1B the syringe barrel 30 is elongate and substantially cylindrical and includes a distal end 31 and a proximal end 35. The syringe barrel further includes and outer circumferential surface 37 and an inner circumferential surface 38. A chamber 32 capable of receiving a plunger and retaining a fluid therein is defined by the inner circumferential surface 38 of the barrel between the distal and proximal ends 31 and 35. A flange 33, which can serve as a finger grip to provide for an easier handing of the syringe, is integrally formed with the proximal end of the barrel and defines an opening 36 for receiving the plunger. Proximate the opening 36, along the inner surface of the barrel, is a ridge 34, shown in FIG. 1C, that prevents the plunger from slipping out of the barrel once it is engaged with the barrel.

The opening 36 is in communication with the chamber 32 and an orifice 39 located at the distal end 20 of the syringe barrel. A tip 40 for attaching a needle, nozzle or tubing for expelling the liquid contained within the syringe barrel 30 is integrally formed with the distal end 20 of the barrel and in communication with the orifice 39. The tip may include coaxially positioned inner 41 and outer 42 members. According to one embodiment the tip may include a Luer taper fitting. In some embodiments, the tip may be configured based on the type of drug that the syringe is used to deliver. For example, oral tips may be used on syringes configured for medicines that are oral, and in particular, the oral tip may be different from an intravenous ("IV") or intermuscular ("IM") tip, thereby ensuring that the medicine is delivered by the right route. Similarly, syringes configured for IV and IM drugs may be configured with IV and IM tips, respectively, such that they, too, can only be delivered via the right route.

The plunger 50, according to one embodiment shown in FIG. 1B, includes a plunger rod 51 and a rubber or plastic gasket or stopper 52 attached to the distal end 56 of the plunger rod. The gasket forms a tight seal between the inner surface of the barrel and the plunger in order to prevent the contents of the syringe from escaping out the back of the syringe. An annular flange 53 is integrally formed with the proximal end 55 of the plunger rod. The plunger 50 has an elongate shape complementary to that of the chamber 30 and is designed such that it can be pushed along the chamber (inside of the cylindrical barrel or tube) allowing the syringe to expel fluid through the tip 40 or orifice 39 at the distal end of the barrel. Alternatively, the plunger can include any other configuration capable of forcing the fluid from inside the chamber 30 through the tip 40 or orifice 39.

According to one embodiment of the present disclosure, the medicine dosing device may be prefilled with a pre-selected drug. Initially, when the medicine dosing device is prefilled and the syringe is in the pre-medication adminis-tration position, the substantial length of the plunger rod extends longitudinally outside of the syringe barrel. In other words, as shown in FIG. 1A, prior to the administration of the medicine, only the gasket 52 and the distal end 56 of the plunger rod are initially inside the syringe barrel, at the proximal end 35 of the barrel, with the remaining part of the plunger length outside of the barrel such that its proximal end 55 is in its most extended configuration.

Alternatively, the medicine dosing device may not be prefilled. The medicine dosing device may be marked, for example, with a drug name, concentration, volumetric mark-ings, color coded zones, and/or the like. In embodiments, the medicine dosing device may have a "stair-stepped" visual dosing indicator, which will be described more thoroughly later in the disclosure. A medical professional may draw the drug (i.e., the drug with the name marked on the device) with the proper concentration into the medicine dosing device to reach the appropriate volumetric markings and/or color-coded zones. In some embodiments, the medicine dosing device comes as a part of a kit that includes a medicine vessel containing the drug to be administered. The drug in the medicine vessel may be drawn into the medicine dosing device immediately prior to the drug administration process. In such embodiments, the plunger rod may remain inside the syringe barrel until the drug is drawn into the syringe.

Figure 2A:
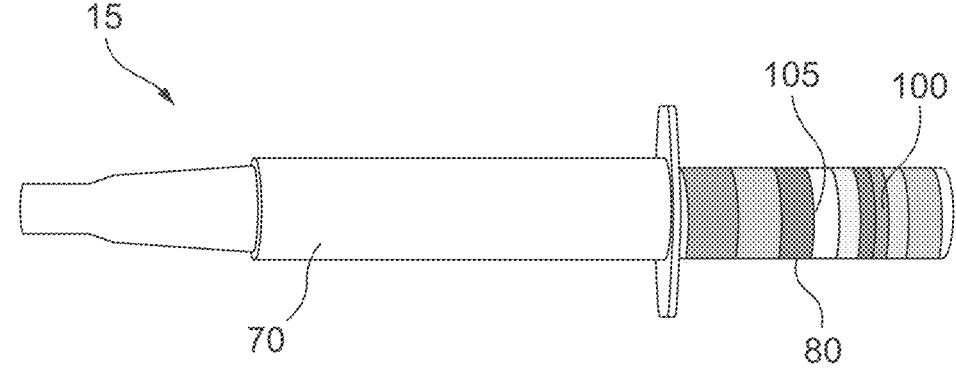
FIGS. 2A-2D are perspective views of a medicine-dosing device according to another embodiment of the current disclosure.
Figure 2B:
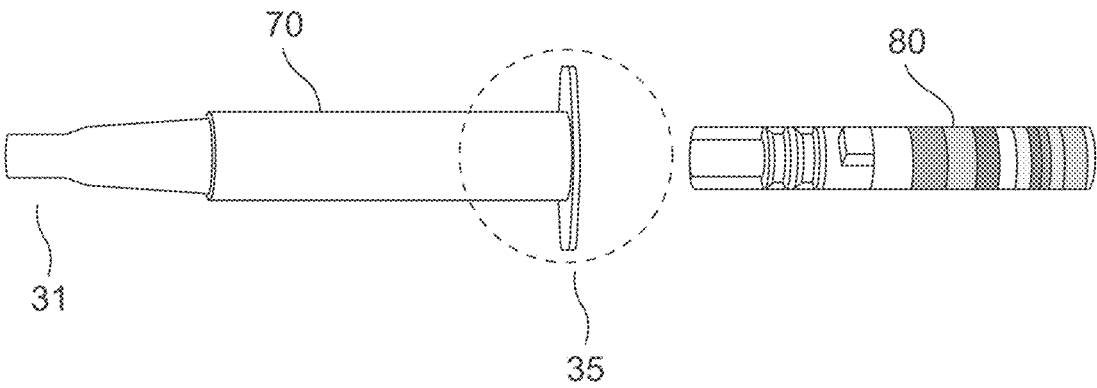
Figures 2C, 2D:
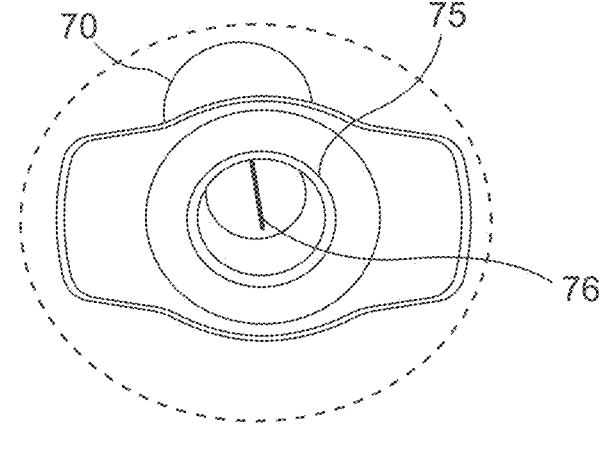

According to another embodiment shown in FIGS. 2A, syringe 15 may include an elongate barrel 70 and a plunger 80 marked with predetermined color-coded volumetric medicine doses 100 and/or prefilled with a fluid 105 that corresponds to a medication to be administered to a patient. In this configuration, as illustrated in FIG. 2C the syringe barrel includes an inner tubular body 75 that is generally coaxially aligned with the larger diameter of the cylindrical barrel. The inner tubular body has a needle 76 coaxially positioned within the inner tubular body and longitudinally aligned with the inner tubular body. The plunger 80, shown in FIG. 2D, includes a substantially cylindrical member or vial 81 and a stopper 82. Because the syringe barrel and the plunger are initially separated, as shown in FIG. 2B, prior to the administration of the medication, the plunger 80 needs to be inserted into the proximal end 35 of the syringe barrel, such that the stopper 82 fully engages with the inner tubular body 75 and the needle 76.

According to yet another embodiment of the current disclosure the plunger and/or plunger stopper can be color coded based on the medication contained in the barrel. Such color coding of the plunger can further increase efficiency with which medication is administered and can make the administration even less error prone as visual inspection of the plunger can provide a quick verification of the correct-ness of the medication to be administered. Alternatively, or in addition to the color-coded plunger and/or plunger stop-per, the plunger and/or plunger stopper may be further marked with the name and/or concentration of the drug to further limit the possibility that a mistake is made.

Alternatively, the medicine dosing device can include any vessel, such as for example a tube, vial, bag, cup, spoon, or bottle, capable of containing therein and expelling therefrom a desired medicine. For example, the medicine dosing device could be a bag containing an IV fluid. According to this embodiment, the bag may be marked with a series of color-coded zones along with the traditional volume mark-ings. When used in combination with the traditional volume markings, the color-coded zones could serve as a reminder to the medical personnel of a correct volume of each medication that can be given to a patient based on the patient's color zone. The color-coded zones may also be used as a key for entering a correct total volume to be dispensed into the IV pump for a given medication.

The description will now turn to the markings on the surface of the medicine dosing device. In case of a syringe, the markings may be placed along a circumferential surface of the syringe barrel or plunger. As shown in FIGS. 1 through 3, the markings include a series of substantially translucent bands or zones 100 indicative of the possible medicine doses to be administered to a patient. Although the markings shown in the figures include a series of color-coded zones, the markings could also include zones with different patterns, textures, etc. Regardless of the type of the marking used, the markings are either directly imprinted, painted, etched or stained on an inside or outside surface of the medicine dosing device or a label or sleeve may be generated that can be affixed or placed over the outer surface of the medicine dosing device. The applied markings are such that the fluid level, once the device is filled, can be easily seen through the markings.

Figure 3A:
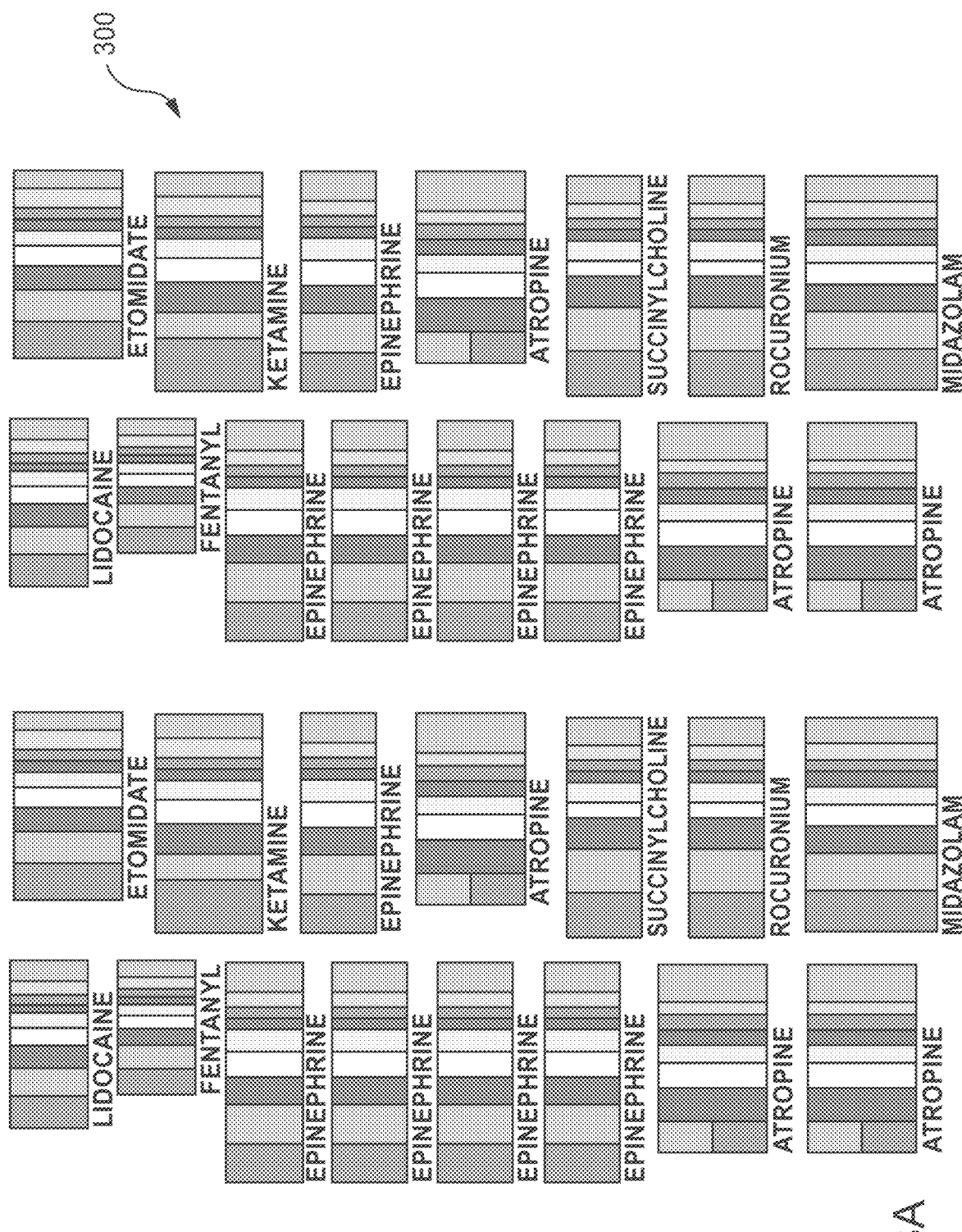
FIGS. 3A-3D are plan views of the labels with the color-coded medication doses.

FIG. 3A shows a plurality of labels in accordance with one embodiment of the current disclosure. Each label 300 is substantially rectangular in shape and is sized based on the volumetric capacity of the medical dosing device to which the label is to be affixed. In other words, because of the volumetric variations among the medicine dosing devices and as a result of variations in the circumferential outer surface of such devices, the size or dimensions of the label is adjusted accordingly to ensure that it properly covers the outer surface of the of the medical dosing device. For example, when labels are made for syringes with two different volumetric barrel capacities, the label size is either increased or decreased in both length and width to accom-modate for the changes in the outer surface of the barrel.

Figure 3B:
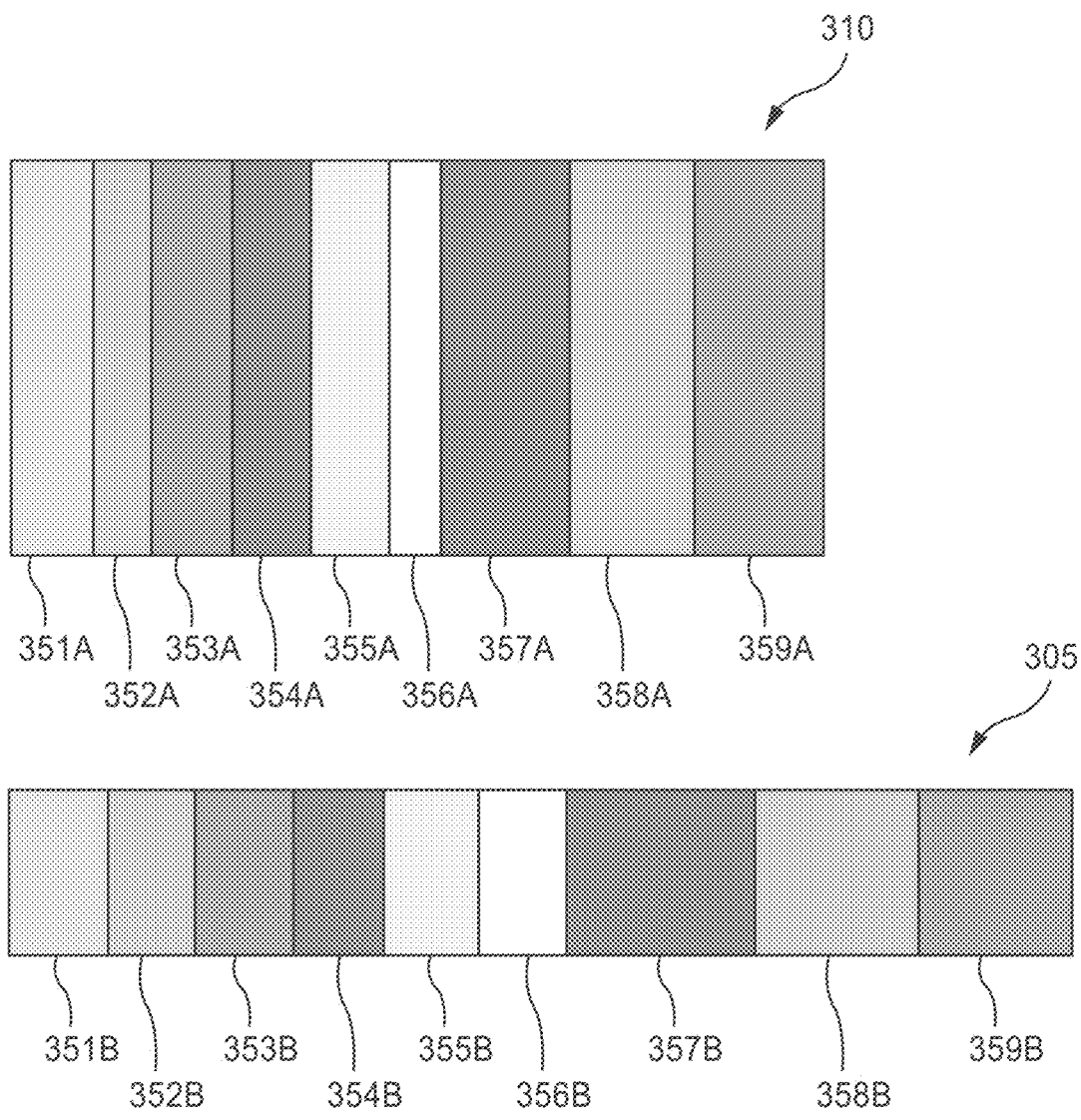

Along with the changes in the label size, appropriate corresponding changes to the widths of the color bands or zones that are printed on the label are also made based on medicine dosing device used to dispense the medication. More specifically, in order to take into account the variations in the volume of a medicine-dispensing dev ice, the changes to the widths of the color bands or zones need to be made in order to maintain the same volumetric dose of medicine across various medicine dispensing devices. For example, as shown in FIG. 3B, labels for the same medicine loaded into a 10 cc medicine dispensing device and 5 cc dispensing device have two different widths for each color band or zone in order to keep the medicine doses the same for both medicine dosing devices. In other words, in order to dis-pense the same amount of medication using a 10 cc dis-pensing device as compared to using a 5 cc dispensing device, the width of the color bands 351A-359A on the label 310 for the 10 cc device would be smaller than the color bands 351B-359B on the label 305 for the 5 cc dispensing device in order to deliver the same amount of medication to the patient.

Similarly, the concentration of the medication that is used also affects the widths of the color bands or zones printed on the label. More specifically, the widths of the color bands or zones are determined based on the concentration of the medication, with the medication at a higher concentration corresponding to a smaller volumetric dose, or smaller band width, than the medication at a lower concentration.

Figure 3C:
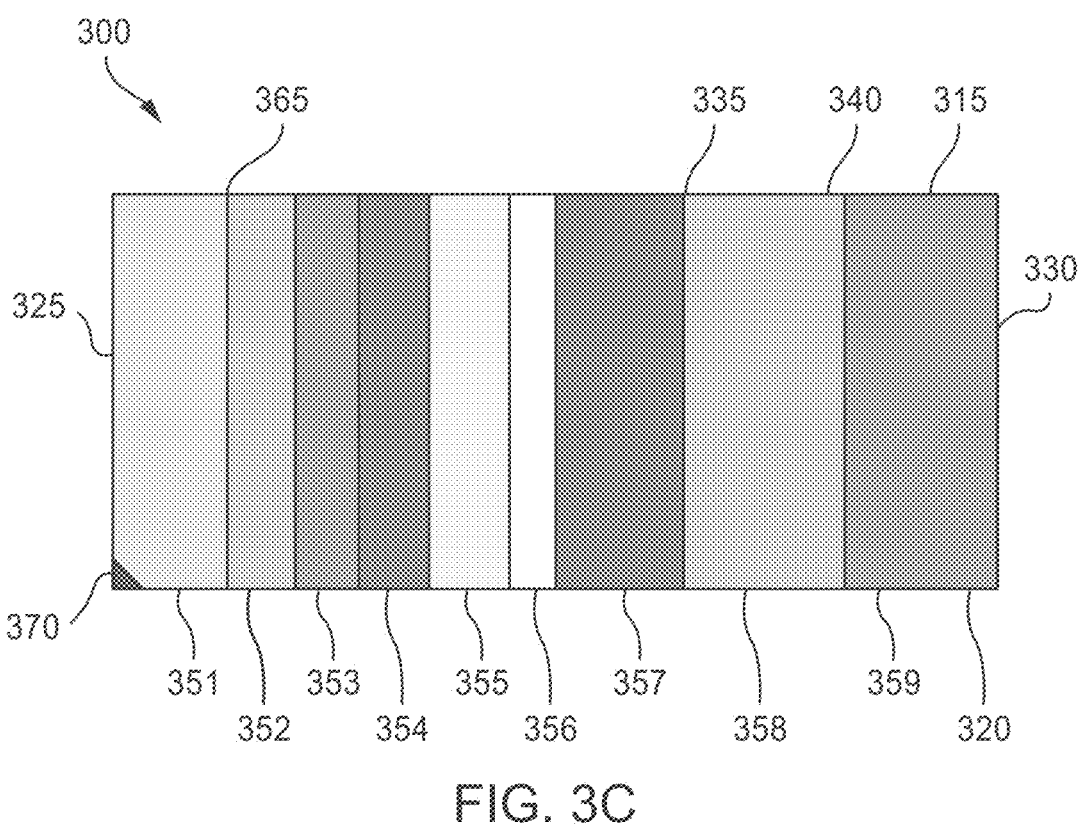

As depicted in FIG. 3C the label 300 has opposing parallel sides 315 and 320 and opposing parallel ends 325 and 330 and includes a series of consecutive color bands or zones 351 through 359 of varying widths that correspond to the medication doses for patients with a particular characteristic. The characteristic may correspond to patient length (as discussed above), patient weight, patient age, patient surface area/volume, and/or the like. More specifically, each color band has a width that is defined by leading 335 and trailing 340 edges that are parallel to the opposing ends 325 and 330 of the label and which, once the label is affixed to the medicine dispensing device, corresponds in volume to a predetermined dose of medicine appropriate for the patient characteristic of a patient that falls within a predefined color-coded range. In other words, each color band or zone on the label represents a medication dose correlated to respective color-coded length range, weight range, age range, surface area/volume range, or other physiological characteristic.

Still referring to FIG. 3C, according to one embodiment, nine distinct color bands 351-359 can be used to distinguish between nine different doses of medication corresponding to nine distinct color-coded patient characteristic ranges. More specifically, each of the colors corresponds to one of nine different doses of a specific medication. As shown in the FIG. 3C, in one particular implementation, band colors may include grey 351, pink 352, red 353, purple 354, yellow 355, white 356, blue 357, orange 358 and green 359, with the grey color band corresponding to the smallest dose of the medication and the green color band corresponding to the largest dose of medication that can be delivered. A solid black line(s) 365 may be utilized at the boundaries between the various color bands or zones to facilitate the process of drug administration as will be discussed in more detail below. Although the discussion will be made with reference to the specific colors shown in the FIGS. 3A-3C, it can be readily appreciated that other colors or markings may be used. Alternatively, or additionally, color names may be printed within the band or zone widths in addition to or instead of colors.

Figure 3D:
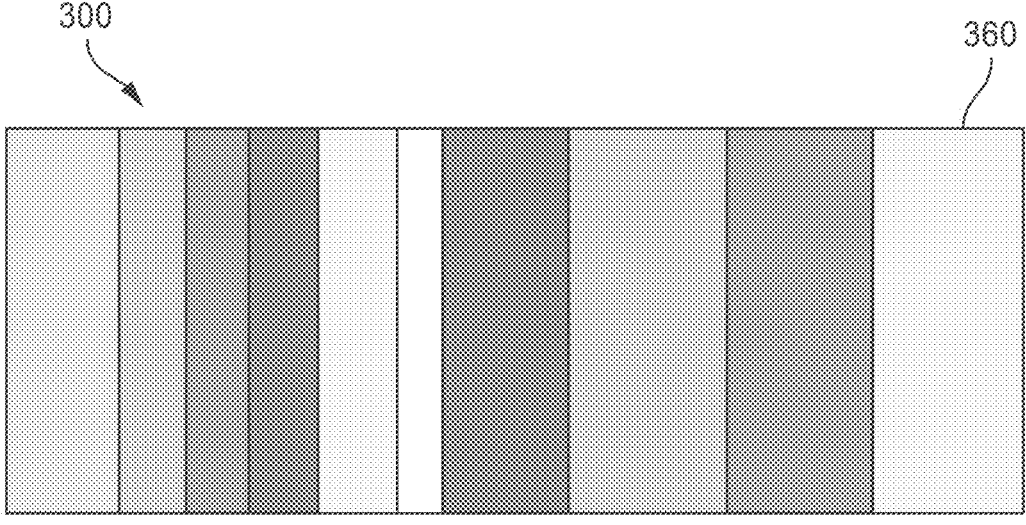

According to yet another embodiment shown in FIG. 3D, a label may include ten different bands of colors with the tenth band 360 corresponding to the largest dose of medication that can be delivered. In this particular embodiment the largest dose can correspond to the universal dose that can be delivered to any patient whose characteristic (e.g., length, weight, etc.) falls outside of the previously disclosed colored ranges. For example, the universal label in accordance with this embodiment can be applied to the universal medicine-dosing device that can be used for both pediatric and adult patients and as such eliminates a need for having two separate medicine dosing systems for the two distinct patient groups.

Although, in the examples provided above a specific number of color bands have been discussed, it should be noted that any number of color bands that allow for more precise medicine dosing can be used. In some cases, the previously defined bands or zones can be further subdivided into sub-band or sub-zone to allow for a more precise medicine dosing. As a non-limiting example, in some embodiments, there may be thirty-six markings (sub-zones) within nine color zones. This may increase precision when administering a drug to a patient.

Also, in accordance with another embodiment of the current disclosure, and as shown in FIG. 3C one of the label edges can include a mark 370 that would help ensure that the label is correctly affixed or positioned on the syringe or plunger. For example, the label edge that is to be aligned with the distal end of the syringe barrel can be marked in order to prevent affixing the label to the barrel in the reverse direction, and thus leading to the incorrect doses being administered at a later time. For example, the edge of the label with the color band corresponding to the smallest dose can include a mark at its leading edge that facilitates the alignment of the label with a distal end of the syringe barrel.

Furthermore, in accordance with another embodiment as shown in FIG. 3A, the label may include the name of the medication that is to be administered or any other information that may be important to ensuring that a correct medication would be administered to the patient. In particular, the name of the medication can be imprinted along the length of the label or any other position as long as it provides for an easy verification of the correctness of the medicine in the medicine-dosing device. Additionally, for drugs that are administered at time intervals, the label may be marked with the corresponding time interval, or a separate calendar, either paper or electronic, may be provided such that the patient and/or medical professionals can keep track of dosing intervals.

Method of Determining and Generating Dosing Information

Figure 4:
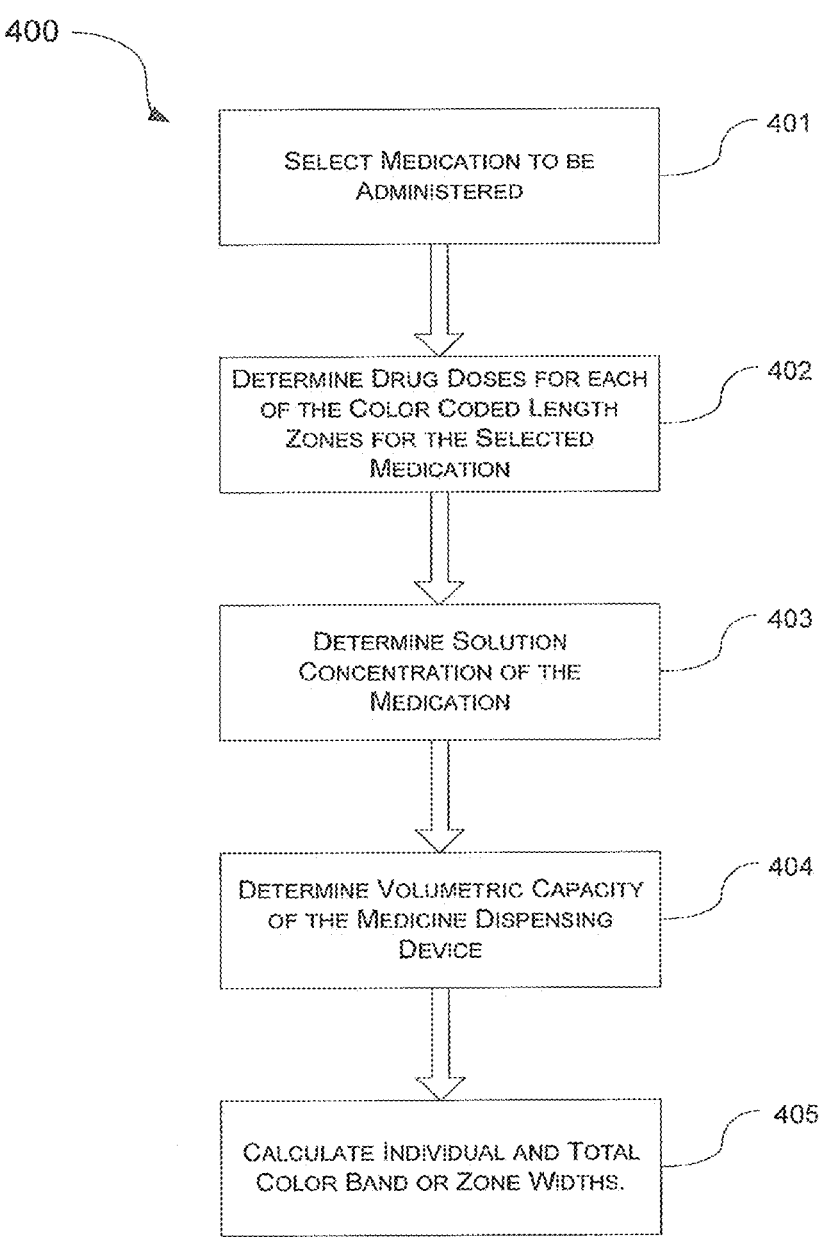
FIG. 4 is flow diagram showing a method of determining and printing the color-coded medication dose labels.

The discussion will now turn to a method 400 for determining the medicine doses for a plurality of medications and medicine dispensing devices. In one particular example, shown in FIG. 4, the method may include generating of a color-coded dose label that can be applied to a selected medical dosing device. As shown in FIG. 4, the method 400 begins at step 401 during which the selection of the medicine for which the dosing label is to be generated is made. As related to emergency or critical care situations some of the most commonly used medications include, for example, atropine, lidocaine, fentanyl, epinephrine, etomidate, ketamine, succinylcholine, rocuronium, and midazolam to name a few. However, it should be appreciated that the method can be equally applied to any other medication that can be administered using the disclosed medicine dispensing device.

Once the medication for which a label is to be generated is identified, the doses of the drug for each of the color-coded characteristic (e.g., length, weight, etc.) zones previously discussed is determined at step 402. Depending on the drug, the width of the color-coded zones may differ. Table 1 below provides doses in mg for some of the above listed drugs. As can be seen in Table 1, the doses for each drug differ not only based on the type of the drug but also based on the length (i.e., characteristic) of the patient. Thus, for example, as shown in Table 1, a dose for a patient falling within the yellow color-coded length zone is 26 mg for succinylcholine and 13 mg for rocuronium. In case the same drug is to be administered to two different patients whose length falls within different color-coded lengths, two different medication doses would be used as shown. For example, in the case of epinephrine, with one of the patient lengths being coded as red and the other as blue, the dose of medication to be administered to each patient would be 0.085 mg and 0.21 mg, respectively. Alternatively, doses of the drug may be determined based on dosing recommendations other than those based on the length of the patient, such as, for example, the patient's weight, age, surface area/volume, and/or the like.

After the dose to be administered to the patient is determined at step 402, the drug concentration for the drug selected in step 401 is then determined at step 403. The concentration of the drug is directly related to the volume that needs to be administered. In other words, a smaller volume of the same medication needs to be administered for a solution with a higher concentration than for a solution with a lower concentration.

The next step, step 404, involves selection of a medicine dispensing device to which the label is to be applied. As described above, because medicine dispensing devices come in various volumetric sizes, a medicine dispensing device's conversion factor that is based on the length and width of the medicine dosing device and/or the concentration of the medication may be used to take into account the variations in size and/or shape of different medicine dispensing devices for which the label is to be generated. Thus, once the medicine dispensing device of a particular volume is selected for administering the selected medication, a corresponding conversion factor listed in Table 1 can be used in order to calculate both the individual color band/zone widths and a total band widths that correspond to the determined medication doses (step 405). More specifically, the width of each color band/zone that corresponds to the determined medication dose is calculated based on the dose of the drug to be administered, the solution concentration and medicine dispensing device volumetric capacity. According to one embodiment all of the calculations may be performed by a computer processing unit (CPU) in response to a user provided input.

Applying of the label to the medicine dosing device may take place once the width of each color-band or zone is determined and the label is printed. For instance, when the label is to be applied to a syringe having a barrel and a plunger, with the barrel designed for holding the medicine that is to be dispensed, the label may be place along the outer circumferential surface of the barrel by aligning one of the edges of the label that corresponds to a color band of the smallest dosing with the distal edge of the syringe barrel of the medicine dispensing device 10. Alternatively, in a syringe in which a plunger serves as a vessel for holding the medicine, the label may be placed along the outer circumferential surface of the plunger by aligning one of the edges of the label that corresponds to a color band of the smallest dosing with the proximal end of the medicine dosing device.

Although the pre-calculated band/zone widths for each of the selected medication, medicine dispensing device volumetric capacity and solution concentration may be printed on a label that can be applied to the medicine dispensing device, the dosing information may also be directly imprinted, etched, stained or painted on the medicine dispensing device. Alternatively, the dosing information can be printed on a sleeve or label that can be placed over the medicine dispensing device. In embodiments, a dosing label may be fixedly attached to the medicine dispensing device such that it does not move once attached.

Depending on the embodiment, the appropriately labeled medicine-dosing device may be prefilled with a desired medication, with the fluid volume corresponding to the maximum dose that can be administered to the patient whose, for example, length falls within the maximum length zone. When the medicine dosing unit is prefilled with the selected medication the label can be applied either before or after the medicine dosing device is filled. In case the medicine dosing device is filled with a selected medication immediately prior to the medication administration process, as might be the case when the medicine dosing device is included as a part of a kit that includes the medical dosing device and a vessel filled with a drug to be administered, an empty pre-labeled medicine dosing device is supplied for use.

Accordingly, a fluid volume that corresponds to a predetermined dose for a given patient may be drawn into the pre-labeled medicine dosing device from the container immediately prior to drug administration.

TABLE 1

| Drug | Color-Coded Length | Dose (mg) | Concentration (mg/ml) | Medicine Dosing Device (cc) | Conversion Factor (mm/cc) | Color band or zone width (mm) | Total Distance (mm) |
|---|---|---|---|---|---|---|---|
| Epinephrine | Gray | 0.04 | 0.1 | 3 | 16 | 6.4 | 6.4 |
| | Pink | 0.065 | 0.1 | 3 | 16 | 4 | 10.4 |
| | Red | 0.085 | 0.1 | 3 | 16 | 3.2 | 13.6 |
| | Purple | 0.1 | 0.1 | 3 | 16 | 2.4 | 16 |
| | Yellow | 0.13 | 0.1 | 3 | 16 | 4.8 | 20.8 |
| | White | 0.17 | 0.1 | 3 | 16 | 6.4 | 27.2 |
| | Blue | 0.21 | 0.1 | 3 | 16 | 6.4 | 33.6 |
| | Orange | 0.27 | 0.1 | 3 | 16 | 9.6 | 43.2 |
| | Green | 0.33 | 0.1 | 3 | 16 | 9.6 | 52.8 |
| Fentanyl | Gray | 12 | 50 | 3 | 16 | 3.84 | 3.84 |
| | Pink | 20 | 50 | 3 | 16 | 2.56 | 6.4 |
| | Red | 25 | 50 | 3 | 16 | 1.6 | 8 |
| | Purple | 32 | 50 | 3 | 16 | 2.24 | 10.24 |
| | Yellow | 40 | 50 | 3 | 16 | 2.56 | 12.8 |
| | White | 50 | 50 | 3 | 16 | 3.2 | 16 |
| | Blue | 63 | 50 | 3 | 16 | 4.16 | 20.16 |
| | Orange | 80 | 50 | 3 | 16 | 5.44 | 25.6 |
| | Green | 100 | 50 | 3 | 16 | 6.4 | 32 |
| Midazolam-RSI | Gray | 1.2 | 1 | 12 | 5.16 | 6.192 | 6.129 |
| | Pink | 2 | 1 | 12 | 5.16 | 4.128 | 10.32 |
| | Red | 2.5 | 1 | 12 | 5.16 | 2.58 | 12.9 |
| | Purple | 3.2 | 1 | 12 | 5.16 | 3.612 | 16.512 |
| | Yellow | 4 | 1 | 12 | 5.16 | 4.128 | 20.64 |
| | White | 5 | 1 | 12 | 5.16 | 5.16 | 25.8 |
| | Blue | 6.3 | 1 | 12 | 5.16 | 6.708 | 32.508 |
| | Orange | 8 | 1 | 12 | 5.16 | 8.772 | 41.28 |
| | Green | 10 | 1 | 12 | 5.16 | 10.32 | 51.6 |

TABLE 1-continued

| Drug | Color-Coded Length | Dose (mg) | Concentration (mg/ml) | Medicine Dosing Device (cc) | Conversion Factor (mm/cc) | Color band or zone width (mm) | Total Distance (mm) |
|---|---|---|---|---|---|---|---|
| Ketamine | Gray | 6.75 | 10 | 6 | 8 | 5.4 | 5.4 |
| | Pink | 13 | 10 | 6 | 8 | 5 | 10.4 |
| | Red | 17 | 10 | 6 | 8 | 3.2 | 13.6 |
| | Purple | 20 | 10 | 6 | 8 | 2.4 | 16 |
| | Yellow | 26 | 10 | 6 | 8 | 4.8 | 20.8 |
| | White | 33 | 10 | 6 | 8 | 5.6 | 26.4 |
| | Blue | 42 | 10 | 6 | 8 | 7.2 | 33.6 |
| | Orange | 50 | 10 | 6 | 8 | 6.4 | 40 |
| | Green | 66 | 10 | 6 | 8 | 12.8 | 52.8 |
| Etomidate | Gray | 0.9 | 2 | 5 | 9 | 4.05 | 4.05 |
| | Pink | 2 | 2 | 5 | 9 | 4.95 | 9 |
| | Red | 2.5 | 2 | 5 | 9 | 2.25 | 11.25 |
| | Purple | 3.2 | 2 | 5 | 9 | 3.15 | 14.4 |
| | Yellow | 4 | 2 | 5 | 9 | 3.6 | 18 |
| | White | 5 | 2 | 5 | 9 | 4.5 | 22.5 |
| | Blue | 6.3 | 2 | 5 | 9 | 5.85 | 28.35 |
| | Orange | 8 | 2 | 5 | 9 | 7.65 | 36 |
| | Green | 10 | 2 | 5 | 9 | 9 | 45 |
| Atropine | Gray | 0.1 | 0.1 | 5 | 9 | 9 | 9 |
| | Pink | 0.13 | 0.1 | 5 | 9 | 2.7 | 11.7 |
| | Red | 0.17 | 0.1 | 5 | 9 | 3.6 | 15.3 |
| | Purple | 021 | 0.1 | 5 | 9 | 3.6 | 18.9 |
| | Yellow | 0.26 | 0.1 | 5 | 9 | 4.5 | 23.4 |
| | White | 0.33 | 0.1 | 5 | 9 | 6.3 | 29.7 |
| | Blue | 0.42 | 0.1 | 5 | 9 | 8.1 | 37.8 |
| | Orange | 0.5 | 0.1 | 5 | 9 | 7.2 | 45 |
| | Green | 0.5 | 0.1 | 5 | 9 | 0 | 45 |
| Succinylcholine | Gray | 8 | 20 | 3 | 16 | 6.4 | 6.4 |
| | Pink | 13 | 20 | 3 | 16 | 4 | 10.4 |
| | Red | 17 | 20 | 3 | 16 | 3.2 | 13.6 |
| | Purple | 20 | 20 | 3 | 16 | 2.4 | 16 |
| | Yellow | 26 | 20 | 3 | 16 | 4.8 | 20.8 |
| | White | 30 | 20 | 3 | 16 | 3.2 | 24 |
| | Blue | 40 | 20 | 3 | 16 | 8 | 32 |
| | Orange | 53 | 20 | 3 | 16 | 10.4 | 42.4 |
| | Green | 66 | 20 | 3 | 16 | 10.4 | 52.8 |
| Rocuronium | Gray | 4 | 10 | 3 | 16 | 6.4 | 6.4 |
| | Pink | 7 | 10 | 3 | 16 | 4.8 | 11.2 |
| | Red | 9 | 10 | 3 | 16 | 3.2 | 14.4 |
| | Purple | 10 | 10 | 3 | 16 | 1.6 | 16 |
| | Yellow | 13 | 10 | 3 | 16 | 4.8 | 20.8 |
| | White | 16 | 10 | 3 | 16 | 4.8 | 25.6 |
| | Blue | 21 | 10 | 3 | 16 | 8 | 33.6 |
| | Orange | 27 | 10 | 3 | 16 | 9.6 | 43.2 |
| | Green | 33 | 10 | 3 | 16 | 9.6 | 52.8 |
| Lidocaine-RSI | Gray | 6 | 20 | 3 | 16 | 4.8 | 4.8 |
| | Pink | 10 | 20 | 3 | 16 | 3.2 | 8 |
| | Red | 13 | 20 | 3 | 16 | 2.4 | 10.4 |
| | Purple | 15 | 20 | 3 | 16 | 1.6 | 12 |
| | Yellow | 20 | 20 | 3 | 16 | 4 | 16 |
| | White | 25 | 20 | 3 | 16 | 4 | 20 |
| | Blue | 32 | 20 | 3 | 16 | 5.6 | 25.6 |
| | Orange | 40 | 20 | 3 | 16 | 6.4 | 32 |
| | Green | 50 | 20 | 3 | 16 | 8 | 40 |

Method of Administering Drugs

Figure 6:
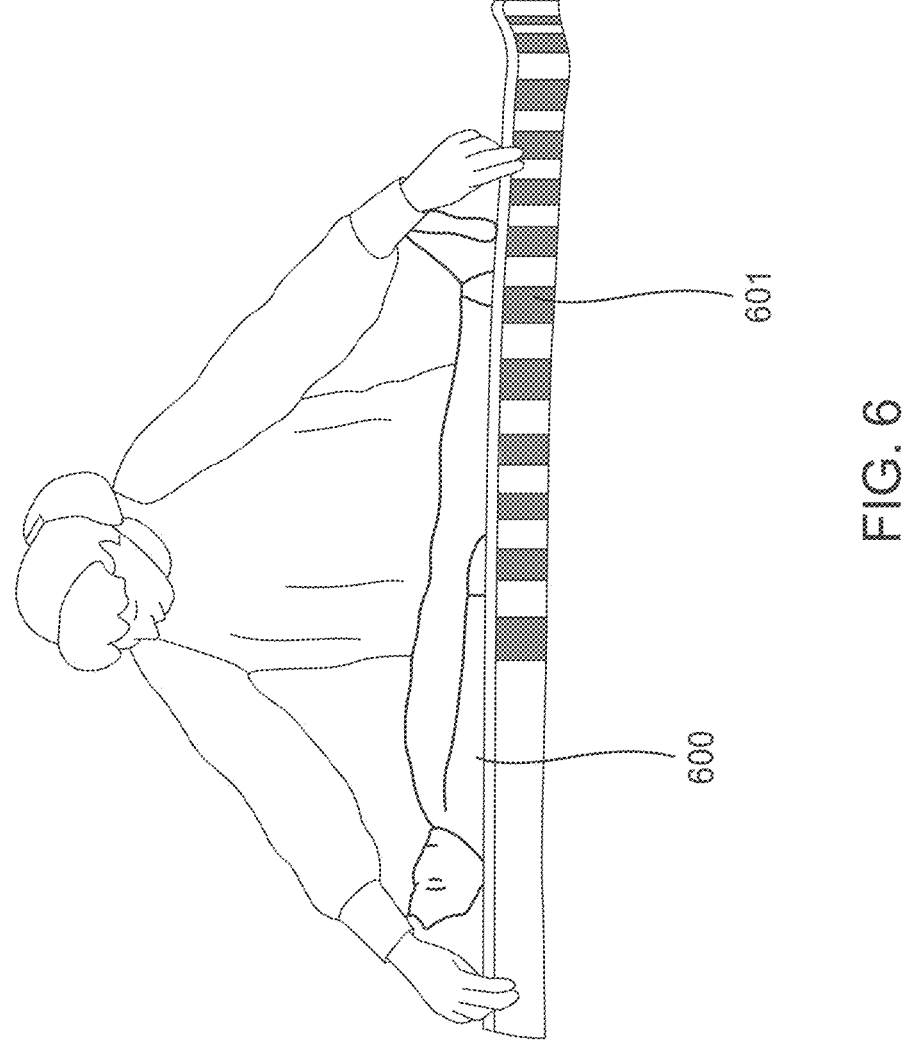
FIG. 6 illustrates a measuring instrument used to determine a color-coded length of a patient.

The medicine dosing device assembled according to the steps discussed above may be used to safely and efficiently deliver drugs. FIG. 5 is a flow diagram 500 of a method for administering drugs to a patient using the disclosed medicine dosing device 10 according to one embodiment. In this particular example, the disclosed method provides steps for efficiently administering a selected medicine to a patient from a prefilled and pre-marked medicine dosing device. As shown in the figure, the method begins at step 501 at which a color-coded length or any other physical characteristic of the patient is determined. In case of the length, a Broselow tape or any other similar type of instrument that provides color-coded length ranges can be used at this step. As shown in FIG. 6, the color-coded length may be obtained by placing a patient 600 along the tape 601 and noting the color-coded length of the patient on the tape. Alternatively, any other physiological characteristic, such as for example, weight, age, body surface area or volume, that can be color coded and correlated to medication doses can be used.

Once the patient length or any other physiological characteristic is determined and/or coded to a specific color range, a pre-filled medicine dispensing device 10 containing medication to be administered is selected at step 502. The medication selection is verified by either reading the name of the medication imprinted along the outer surface of the pre-filled medicine dispensing device or by verifying the color of the plunger rod as discussed above.

After the color code for the patient length or other characteristic is determined and noted and the correctness of the medicine to be administered is verified, the appropriate dose of medication to be dispensed or its corresponding volume is determined at step 503. The appropriate dose may be determined by a physician or other medical professional who calculates the appropriate dose based on at least one patient characteristic. The calculated dose may be a precise amount of a drug to be administered. Additionally, the physician or other medical professional who administers the medication may determine a color code for the patient based on at least one patient characteristic. For example, if the patient length or other characteristic is determined as falling within the blue color range on the measuring tape, the volume of medication to be administered to the patient will be the volume within the blue color band or zone on the medicine dosing device.

Because (in this embodiment) the medicine dispensing unit is prefilled with medication, the appropriate dose of medicine can be obtained by purging any excess of medication from the prefilled syringe until the calculated volume (dose) of the medication is reached as indicated in step 504. In other words, with the prefilled volume of the medicine dispensing device may correspond to the maximum dose that can be administered to a patient. Therefore, unless the calculated dose is the maximum possible dose, some of the medication has to be purged from the prefilled medicine-dosing device prior to administering of the drug.

Thus, according to one embodiment the plunger is pushed along the inside of the barrel toward the distal end 31 of the barrel until the proximal end of the plunger 54 arrives at the calculated dose.

Once the administering medical professional has purged the excess medicine such that the calculated dose is the only medication that remains in the medicine dosing device, the administering medical professional verifies that the calculated dose, and the amount of medication that remains in the medicine dosing device, is within the color coded range determined for the patient. For example, in case of the above mentioned patient whose length or other characteristic was coded as being blue, with the blue band having a leading edge proximate the distal end of the barrel and the trailing edge proximate the proximal end of the barrel, the plunger is pushed toward the distal end of the barrel until the distal end of the plunger is aligned with the calculated dose, and then the administering medical professional ensures that the plunger is between the leading edge and trailing edge of the blue band. Once all the excess fluid is purged from the prefilled dosing device per step 504, the correctness of the medicine dose is verified at step 505 and the medicine is then administered to the patient at step 506.

Alternatively, according to another embodiment, the medicine-dosing device can be used to administer drugs to patients following the method shown in FIG. 7A. In particular, the method for administering drugs can begin with the selection of an emergency medical treatment kit that includes a drug to be administered to the patient (step 701). As shown in FIG. 7B, the medical treatment kit may include a container, such as box, bag, pouch or any other suitable container capable of holding the medicine dosing device therein, labeled on the outside surface with the name of the medication contained in the container among other things. For example, according to one embodiment, in addition to having the name of the drug listed on the label, the label may also include information on the concentration of the drug and/or instruction on how to use the kit to administer the drug. The medical treatment kit may further include a pre-marked medicine dosing device, such as for example a syringe, with the color-coded zones calibrated to the different drug doses for the selected drug. The syringe markings may also include the name of the drug that is to be delivered or any other information that may be helpful in ensuring that the drug is correctly delivered to the patient. The medical treatment kit may also include a needle, such as a blunt filling needle that can be plastic or made of any other suitable material, for facilitating drawing of the drug into the syringe. The medical treatment kit may also contain a container, such a bottle, vial, etc., for holding the drug that is labeled with the drug name on the outside of the container. The container may include a stopper or a lid that helps to contain the drug inside the container. The stopper or lid may be made from, for example, rubber or any other suitable material that can be easily punctured with the filling needle, such that the drug from the container can be easily drawn into the medicine-dosing device.

If more than one drug is included in the kit, the corresponding vials and syringes for each drug may be positioned within the packaging to ensure that there is no confusion as to which vial corresponds to which syringe. Additionally, differently colored plungers will help to ensure that the correct medication is given to the patient in the correct order. For example, in a situation where two drugs are being administered in a specified order, the kit may include a first drug in a first vial with a first syringe marked with the color zones for the first drug, and a second drug in a second vial with a second syringe marked with the color zones for the second drug. To ensure that the first vial and first syringe do not get confused with the second vial and second syringe, the plungers in the syringes may be colored. The color of the label and/or lid of the first vial may be marked with the same color as the plunger of the first syringe, and the color of the label and/or lid of the second vial may be marked with the same color as the plunger of the second syringe. This way, when the drug is being administered, the administrating medical professional can easily to make sure that the correct vial/drug-syringe combination is being used.

Alternatively, or additionally, when the drugs need to be delivered in a particular order, the ends of the plungers may be marked numerically to indicate the order in which the drugs are to be delivered. For example, if the first drug to be administered has a green plunger and the second drug to be administered has a yellow plunger, the end of the green plunger may have a number "1" on the end and the end of the yellow plunger may have a number "2" on the end. The vials may also be marked numerically.

In case drug doses are based on patient's length, the color-coded length of the patient may be determined using an instrument such as a Broselow tape or any other similar type of device that provides color-coded length ranges as discussed above with reference to FIG. 6. Alternatively, other patient characteristics may be used to determine a color-coded range. Appropriate volume of the drug to be administered may be subsequently determined based on the patient length, and the patient length may be correlated to a color code. The determined drug volume may be then drawn into the medicine-dosing device, and the administering medical professional verifies that the determined drug volume is within the color code corresponding to the patient. Once the dose is verified, the drug can then be administered to the patient. According to one embodiment as shown in FIG. 7, when the medicine-dosing device is a syringe with a pre-attached filling needle, the filling needle might be disposed of prior to the administration of the medication.

Figure 8A:
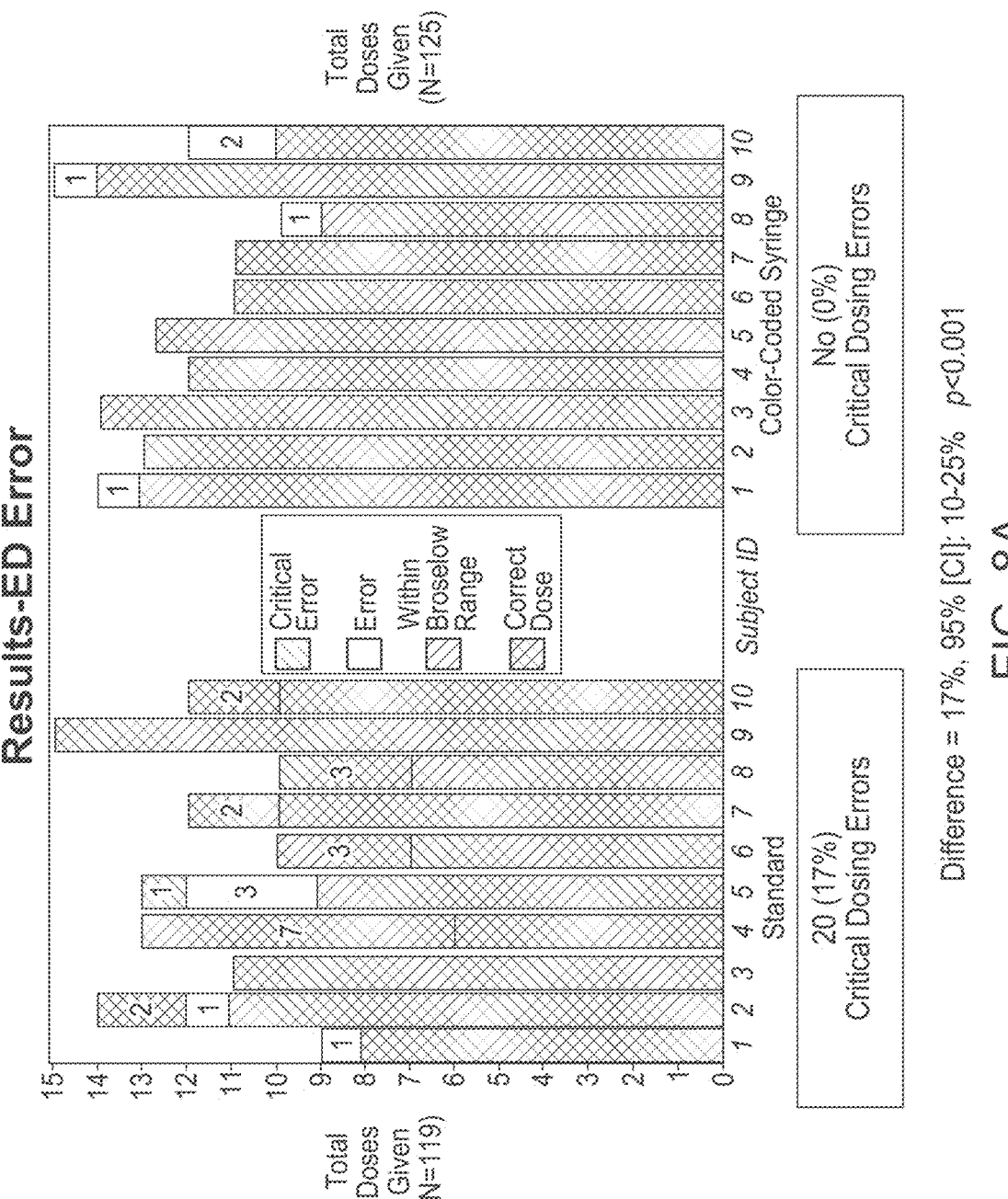
FIGS. 8A-8F includes data showing improvements in the drug delivery using the system and methods of the current disclosure.
Figure 8B:
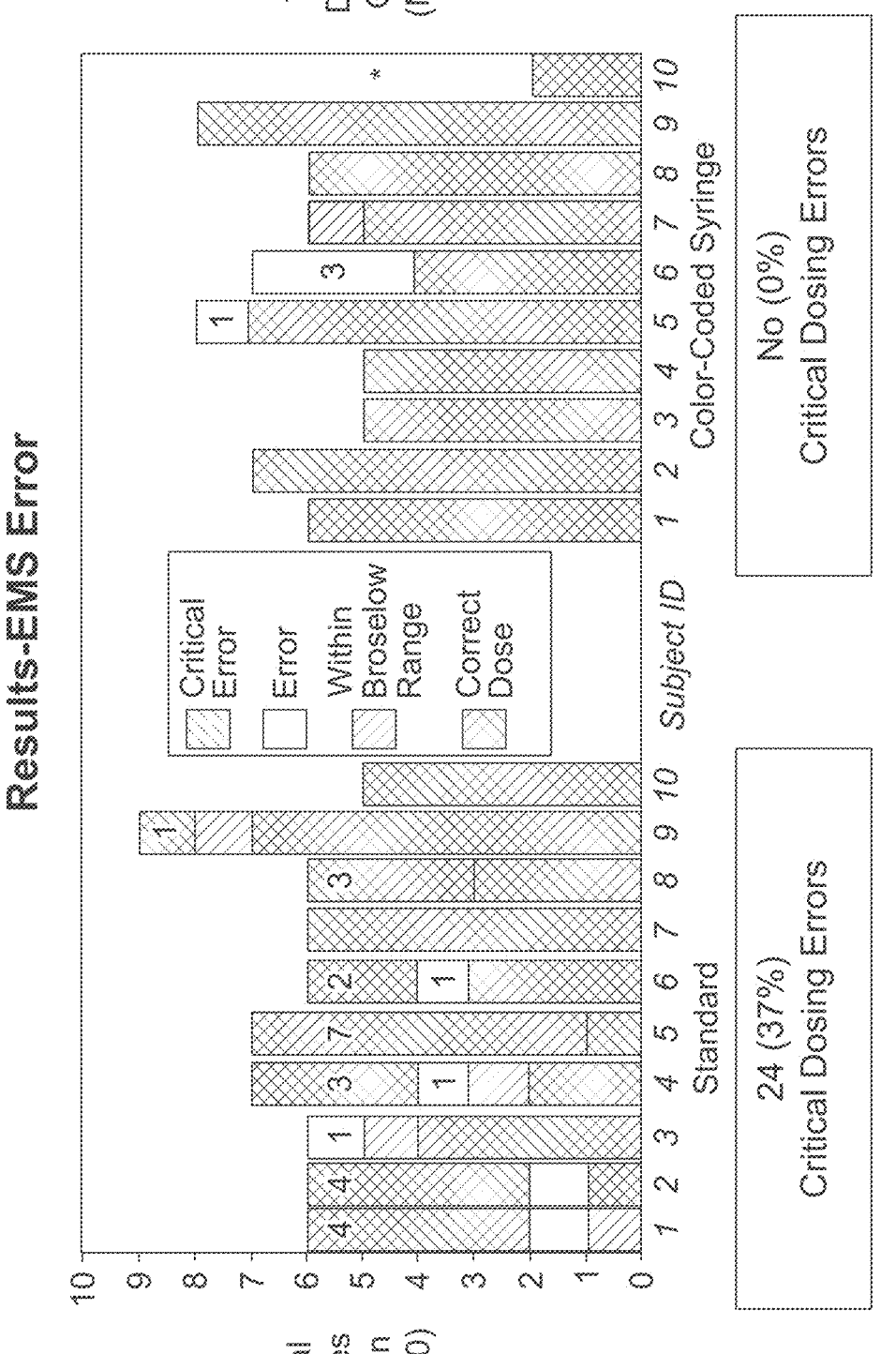
Figure 8C:
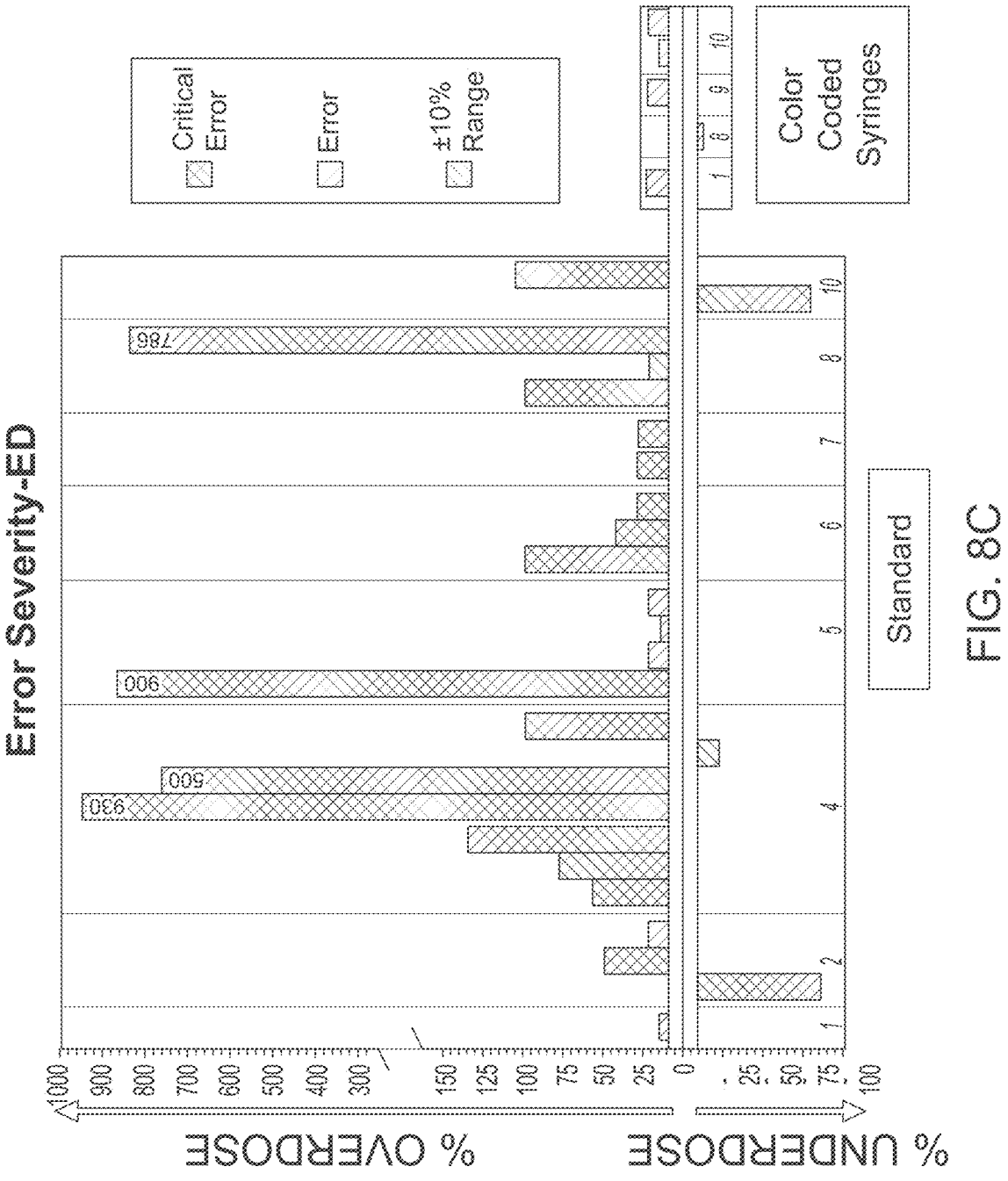
Figure 8D:
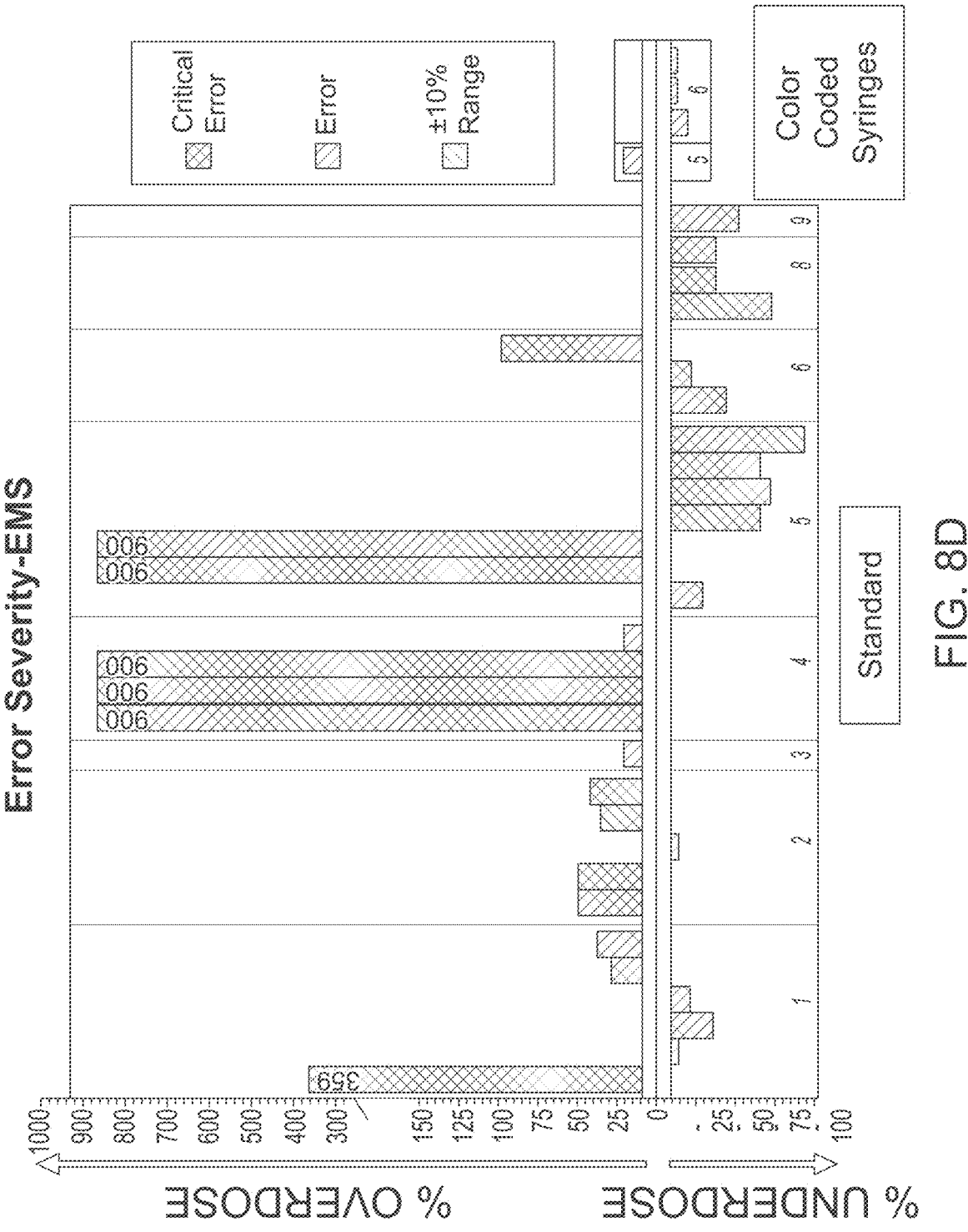
Figure 8E:
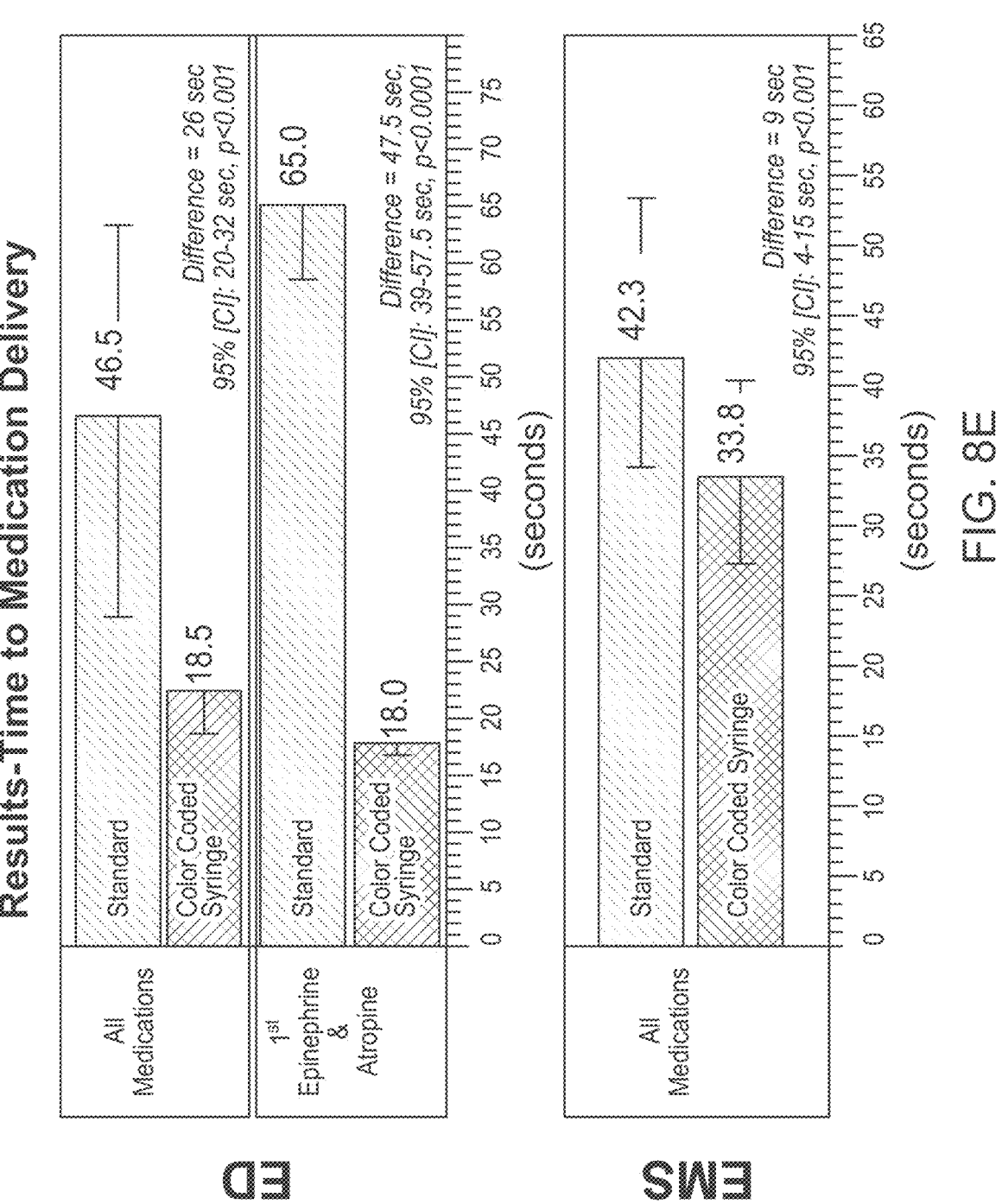
Figure 8F:
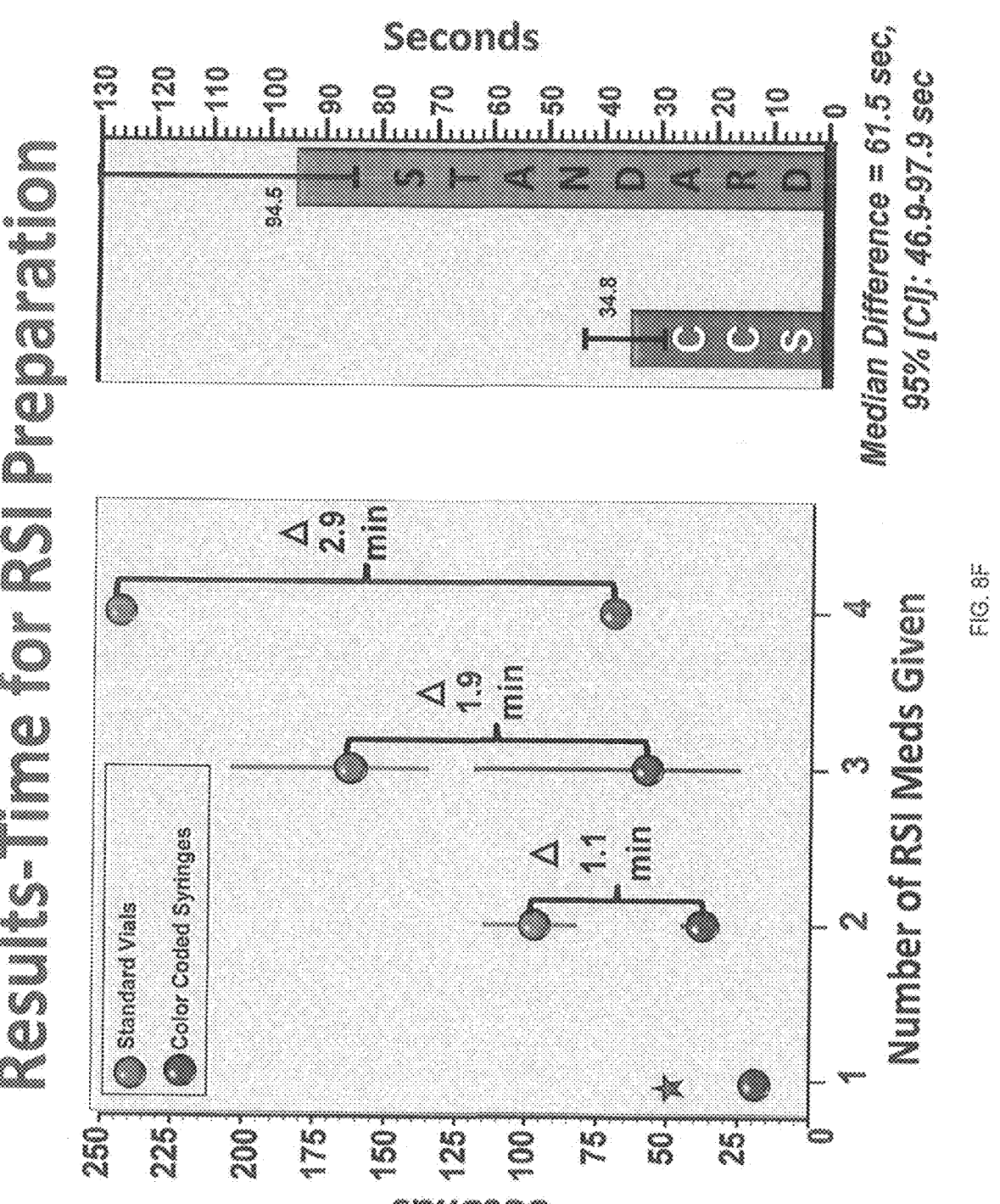

As shown in FIGS. 8A and 8B, eliminating the step of calculating doses that need to be administered in the high stress environment, as well as eliminating the steps of selecting appropriate medicine dosing device helps to eliminate critical dosing errors, such as critical over dose or critical under dose errors, that usually arise when conventional devices and methods are used. Also, frequency and severity of non-critical errors as compared to the traditional methods can be reduced as shown in FIGS. 8C and 8D. Lastly, as shown in FIGS. 8E and 8F, time to prepare and deliver medication, as well as time to deliver medications when preparing for rapid sequence intubations (RSI) may be significantly reduced when the medicine-dosing device according to the current disclosure is used as compared to the conventional devices. As such the pre-labeled medicine dispensing device designed and used in accordance with the disclosed embodiments provides for more simplified, accurate and efficient drug delivery in emergency and critical care situations.

In another embodiment, the dose may be calculated, and the color band/zone may be used to verify that the calculated dose is within a safe range based on at least one patient characteristic. For example, a precise dosage may be calculated based on a patient characteristic, such as patient weight, and to ensure that calculated dose is safe to give a patient, the person administering the drug ensures that the dose is within the correct color band/zone before administering the drug. The color bands/zones may be smaller for certain medications that require more precision. In such situations, a smaller range, or even exact precision, may be required in the correlation between the patient characteristic and the dosage.

By first calculating a dose and then verifying that the determined dose is within a safe range (i.e., color zone) for the patient, errors in dosing can be avoided because everyone in the chain of drug delivery is able to identify when an error has been made. For example, a physician may calculate a dose, but a nurse (or a second doctor) may administer the medication to the patient. If an error in calculation occurs, or if the administering medical professional misreads the calculated dose, the administering professional will know that an error is made before administering the drug to the patient, because the dose is outside of the color zone that corresponds to the patient. (In some embodiments, the patient's color zone may be determined at the time the drug is administered, may be marked on the patient's chart, such as with a marker, barcode that can be scanned, etc., or the child may be asked to wear an arm band in the color that corresponds to the child's safe color zone).

FIG. 9A shows an exemplary flow chart of such an embodiment. A color-coded zone may be determined based on at least one patient characteristic 905. The patient characteristic may be a patient length, patient weight, patient age, patient surface area/volume, and/or the like. In some embodiments, the color-coded zone may be determined based on patient weight, such as by using the chart shown in FIGS. 9C and/or 9D. The drug to be administered to the patient may be determined 910, and a pre-marked dispensing device may be selected 915. In some embodiments, the pre-marked dispensing device may be specifically tailored to the drug (e.g., both the drug name and concentration) being administered to the patient, and the device may have a series of color coded zones that correspond to drug doses that can be administered. The color-coded zones may be of varying widths and may correspond to volumes of the drug that are safe to administer to patients with at least one physical characteristic and/or within a range of the at least one physical characteristic.

A drug dose to be administered to the patient may be determined 920. In some embodiments, the determination of the drug dose is based on calculations made by a physician or other medical professional. For example, the physician may know that a patient having a certain physical characteristic, such as a weight within a predetermined range, should receive a certain amount of the drug (e.g., based on FDA guidelines). The amount of a drug to be given to a patient may be in units of weight (e.g., milligrams). When delivering a drug in liquid form, however, the units are in terms of volume (e.g., milligrams/milliliter). Thus, the medical professional must determine how many milliliters of the drug to deliver to the patient in order to give the proper dose (e.g., milligrams) of the drug to the patient.

Once the drug dose has been determined, the dispensing device may be filled with a volume of the drug based on the determined drug dose 925. The person administering the drug, such as a physician, nurse, technician, physician assistant, and/or the like, may verify that the volume of the drug filled in the dispensing device corresponds with the determined color-coded zone 930. Assuming the volume is within the zone, the drug dose may be administered to the patient using the dispensing device 935. In some embodiments, if the volume is not within the zone, the dose may not be administered to the patient. For example, the drug dose may be re-determined. In other embodiments, the dose may be administered as long as it is not above the determined zone.

Figure 9B:
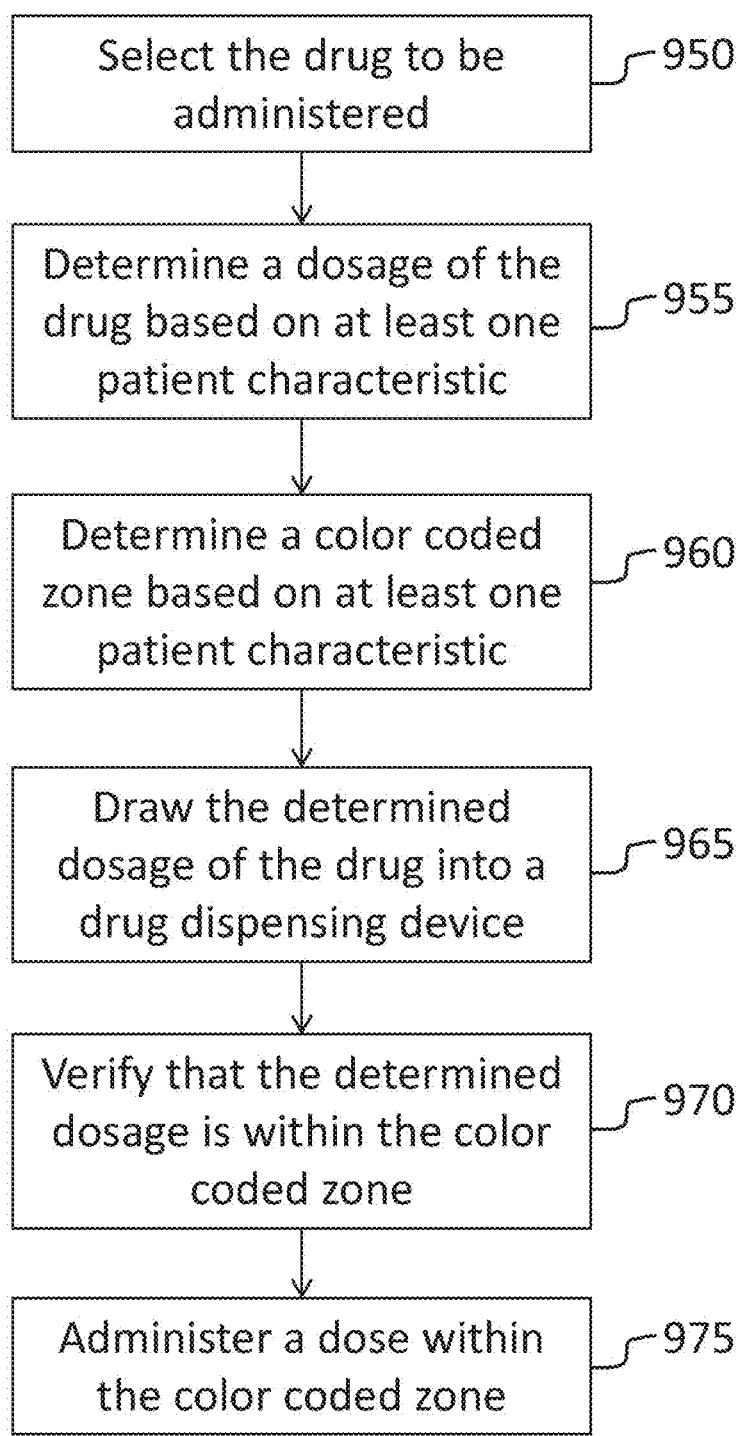
Figures 10A, 10B:
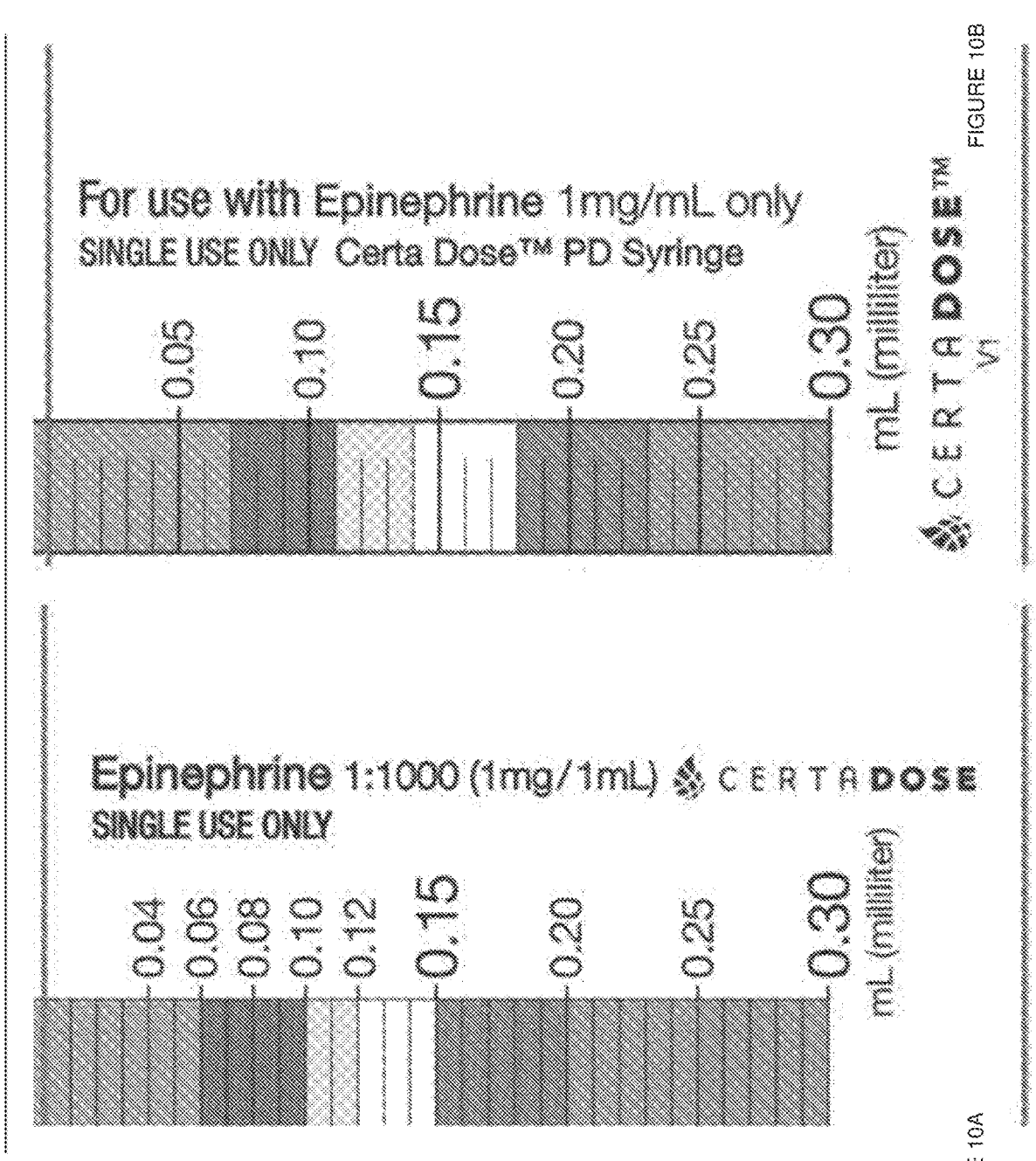
FIGS. 10A-10B illustrate exemplary labels with the color-coded medication doses according to several embodiments.

FIG. 9B shows another exemplary flow chart of such an embodiment. The drug being administered may be selected 950, and a dose of the drug may be determined and/or calculated 955. The dose may be based on a patient characteristic, such as a patient length, patient weight, patient age, patient surface area/volume, and/or the like. A color-coded zone may also be determined based on the same or based on a different patient characteristic 960. The calculated dose may be drawn into the drug dispensing device 965. For example, when the drug dispensing device is a syringe, the calculated dose may be drawn into the syringe from a vial. The syringe may be marked with a plurality of color-coded zones, as shown in FIG. 10B. In order to ensure that a safe dose is administered, the calculated dose should be within the determined color-coded zone 970. If the determined dose is within, and in some embodiments less than, the color-coded zone, the dose is administered to the patient 975. If the determined dose is not within the color-coded zone, for example, if the determined dose is greater than the color-coded zone, the dose is not administered. The excess drug may be expelled from the drug dispensing device, or the dose may be re-calculated (re-determined) in order to ensure that the calculations were performed correctly.

FIG. 9C shows an exemplary chart for determining the color-coded zone for a patient based on patient weight in kilograms (kg). Such a chart may be used in hospitals, where weights may be noted in kilograms for ease of use in dosage calculations.

FIG. 9D depicts another exemplary color-coded chart in which patient weight is shown in pounds (lbs.). In the embodiment of FIG. 9D, the patient length (here, in inches (in.)) is also shown. This embodiment may be particularly useful where doses of medications are delivered at home, since in certain countries (e.g., in the U.S.), patients and caregivers may be more familiar with pounds and inches than they are with kilograms and centimeters. Thus, for example, when a parent is administering epinephrine to their child, they may be able to quickly reference the chart shown in FIG. 9D to determine that their child should be administered a dose falling within the color range that corresponds to their child's weight and/or height.

FIGS. 10A-B show exemplary color-coded zones for a drug, epinephrine, at a concentration of 1 mg/1 ml. The color-coded zones shown in FIG. 10A may be used when the color-coded zone is used to determine the dose to be administered to the patient (e.g., using the process shown in FIGS. 5 and 7A). In these embodiments, the patient length is used to determine the color-coded zone, and the color-coded zone determines the dose to be administered to the patient. In a typical implementation of the disclosed embodiments, a medical professional administering a drug may fill the syringe with the drug to the level of the maximum dose for the color-coded zone corresponding to the patient. For example, if the patient's length (or weight, etc.) falls within the white zone, the medical professional administers 0.15 mL of the drug. This may be a slight overdose for patients at the low end of the white color coded zone, and a slight underdose for patients at the high end of the white color coded zone (of course, the slight overdose/underdose is within a safe range of doses for patients that fall within the white zone). In other embodiments, the doses corresponding to the color zone may be an accurate dose for patients at the low end of their respective color-coded zone, and may be a slight underdose for patients in the middle and high end of the color zone.

FIG. 10B shows color coded zones that may be used when the processes shown in FIGS. 9A-9B are used. Here, the calculations may be precise, and the colors are used to double check that the dose is in a safe range. Because dose is calculated and the color-coded zones are used to verify that a proper dose is applied, the color-coded zones can be more accurate. As was discussed with reference to FIGS. 9A-9B, the administering professional fills a syringe to a level corresponding to the exact dose calculated for the patient and then ensures that the calculated dose is included within the color-coded zone corresponding to the patient.

In the embodiment of FIG. 10B the zones are not configured so that a slight overdose/underdose is administered to patients on either side of each zone. Instead, each color zone extends only to the maximum acceptable dose for any patient within a zone (e.g., to the maximum acceptable dose for the lightest or shortest patients within the zone). As a result, the volumes of the color-coded zones are shifted between FIG. 10A and FIG. 10B. As an example, consider a case in which a patient weighs 14 kg, and is therefore at the top of the 'yellow' range. In the embodiment of FIG. 10A, the patient would receive 0.12 mL of epinephrine. In the embodiment of FIG. 10B, the dose may be calculated to be 0.14 mL of epinephrine. When this dose is in the medicine dosing device, the administering professional sees that the dose is appropriate for the yellow zone, double checks that the patient is categorized for the yellow zone, and then administers the drug. Thus, although the patient receives a higher dose in the embodiment of FIG. 10B, this higher dose is accurate and safe. To the contrary, if a physician were to calculate that the patient should receive 0.20 mL of the drug, the administering professional would see that this dose falls in the blue zone; knowing that the patient is categorized within the yellow zone, the administering professional would not administer the drug. This prevents an overdose of the medication and ensures that the patient receives the correct amount of the drug.

In an exemplary implementation, if a physician calculates a dose for the patient of 0.15 mL, the medical professional administering the drug will fill the syringe (whether by dispelling the drug from a pre-filled device or drawing medication into the device) to the 0.15 mL marker. Next, the medical professional checks the patient's color-coded zone.

If the patient is within the white zone, the professional administers the drug; if the patient is within any other zone, the medical professional does not administer the drug, and instead ensures that the dose is recalculated. In some embodiments, it may be particularly important for the medical professional to ensure that the patient is not overdosed with medication. Thus, if the patient is within a color zone that is higher than the calculated dose, the administering medical professional may administer the drug and then ensure that the remainder of the dose is given (e.g., a 'blue' zone patient may be given a 'white' zone dose, followed by the remaining dose at a later time. Thus, the 0.15 mL dose may be administered, and then if the proper dose should have been 0.20 mL, the remaining 0.05 mL may be administered).

Figures 11, 12:
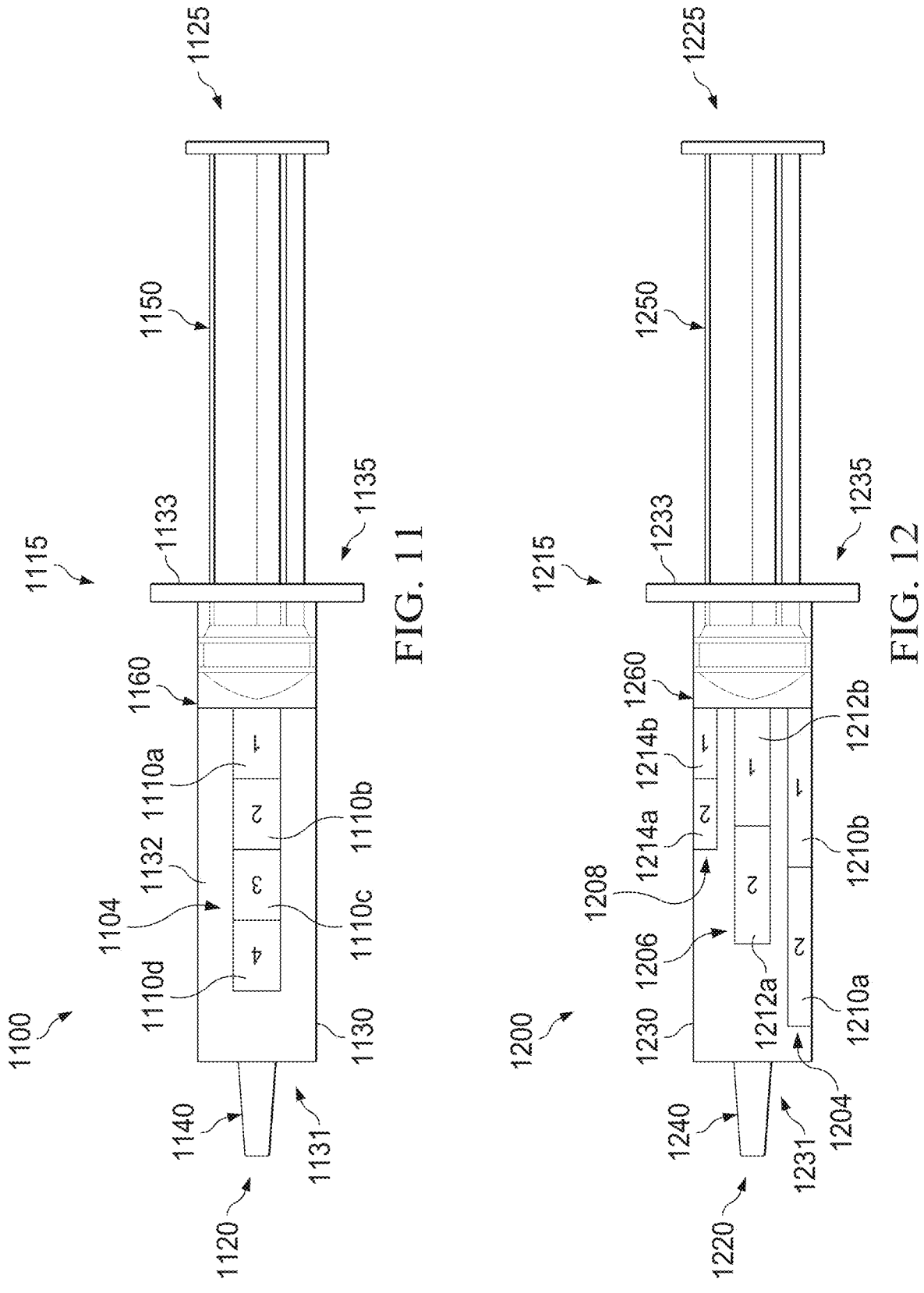
FIG. 11 depicts an embodiment of a dosing system including a pre-labeled medicine dosing/dispensing device designed to facilitate delivery of sequential doses of medication to a patient in a safe manner.
FIG. 12 illustrates a dosing system including a pre-labeled medicine dosing/dispensing device having stair-stepped dosing indicators designed to facilitate delivery of sequential doses of medication to any one of multiple different-sized patients.

Attention is now directed to FIG. 11, which depicts an embodiment of a dosing system including a pre-labeled medicine dosing/dispensing device 1100 designed to facilitate delivery of sequential doses of medication to a patient in a safe manner. As shown, the dosing device 1100 is printed, labeled or otherwise marked with a color dosing bar 1104 having four dosing segments 1110. In one embodiment the color dosing bar 1104 is of a color (i.e., green) that is correlated with a parameter of a patient (e.g., the patient's weight or length). Each of the dosing segments 1110 identifies a volume of the medication corresponding to a given medication dose to be provided to the patient. For example, a first dosing segment 1110a corresponds to a first dose to be provided to the patient, a second dosing segment 1110b corresponds to a second dose to be provided to the patient, a third dosing segment 1110c corresponds to a third dose to be provided to the patient, and a fourth dosing segment 1110d corresponds to a fourth dose to be provided to the patient.

The dosing system of FIG. 11 has particular utility in situations in which the practice of medicine requires that sequential doses of the same medicine be provided to a patient. Such situations often arise in the context of emergency treatment where available resources and time may be limited. For example, in an emergency situation involving a cardiac arrest, the same dose of a particular medicine must generally be given to the cardiac patient during each of a number of successive 3-minute intervals. In some situations, up to 20 doses of a medication must be sequentially given to a patient before the patient can be safely transported to a hospital setting for further treatment. When conventional dosing instruments are utilized in such emergency scenarios, critical time can be lost in calculating/measuring medicine dose as well as in getting different preparations of the medicine ready for administration to the patient.

These shortcomings of conventional dosing approaches can be overcome by utilizing the sequential dosing system of FIG. 11. Specifically, the dosing segments 1110 enable a predetermined number (4 in the case of FIG. 11) doses of a medication to be prepared in advance and sequentially delivered to a patient through the device 1100. In one embodiment an operator of the dosing device 1100 need not perform any mathematical calculations in order to arrive at a correct sequence of dosages to be delivered to a patient. For example, once a parameter of the patient (e.g., weight or length) has been correlated to a particular dosing color (green in the case of FIG. 11), a dosing device 1100 having a color dosing bar 1104 having a color the same as the dosing color correlated with the patient is selected. The dosing segments 1110 then effectively serve to inform the operator of the dispensing device of the proper volumes of medication to be administered in each successive dose in light of the patient's size, concentration of the medication, and desired medication dose (e.g., mg/kg of body weight) without requiring the operator to engage in any calculations. This sequential delivery of multiple, pre-prepared doses of medication through a single instrument in a manner not requiring a medical professional to engage in mathematical calculations or the like to determine dosing levels is not possible using conventional syringes or other conventional drug delivery devices.

Referring to FIG. 11, the medicine dosing device 1100 according to one embodiment is a syringe 1115 that includes a proximal end 1125 and a distal end 1120 opposite the proximal end. The syringe includes a vessel, such as a syringe barrel 1130 for holding therein a medicine that is to be dispensed, and a plunger 1150 that extends proximally from an opening located at the proximal end 1135 of the syringe barrel to the proximal end of the plunger at the proximal end 1125. The syringe barrel 1130 and plunger 1150 are both manufactured from material such as plastic, glass or any other suitable transparent medical grade material that is inert or will not disrupt the chemical balance of the fluid inside.

As illustrated in FIG. 11, the syringe barrel 1130 is elongate and substantially cylindrical and includes a distal end 1131 and a proximal end 1135. A chamber 1132 capable of receiving a plunger and retaining a fluid therein is defined by the inner circumferential surface of the 1130 barrel between the distal and proximal ends 1131 and 1135. A flange 1133, which can serve as a finger grip to provide for an easier handing of the syringe, is integrally formed with the proximal end of the barrel and defines an opening for receiving the plunger 1150. Proximate this opening, along the inner surface of the barrel, may be a ridge (not shown), that prevents the plunger from slipping out of the barrel once it is engaged with the barrel.

The opening defined by the flange 1133 is in communication with the chamber 1132 and an orifice located at the distal end 1120 of the syringe barrel. A tip 1140 for attaching a needle, nozzle or tubing for expelling the liquid contained within the syringe barrel 1130 is integrally formed with the distal end 1120 of the barrel and in communication with the orifice. In some embodiments, the tip may be configured based on the type of drug that the syringe is used to deliver. For example, oral tips may be used on syringes configured for medicines that are oral, and in particular, the oral tip may be different from an intravenous ("IV") or intermuscular ("IM") tip, thereby ensuring that the medicine is delivered by the right route. Similarly, syringes configured for IV and IM drugs may be configured with IV and IM tips, respectively, such that they, too, can only be delivered via the right route.

In one embodiment the barrel 1130 is marked with a reference line 1160 (zero line). In cases in which the syringe barrel 1130 is pre-filled with medication, syringe doses may be calculated from the proximal end 1135 of the barrel 1130 or from the reference line 1160. Sequential doses may then be delivered to a patient where each dose comprises a volume of medication corresponding to one of the dosing segments 1110.

If the syringe 1115 is provided to an operator in an empty state, the syringe 1115 would be filled by the operator with medication from, for example, a medication vial. In this case the orientation of the label 1104 would be reversed relative to the orientation shown in FIG. 11. That is, the label 1104 would be oriented such that the dosing segment 1110 corresponding to the first of multiple sequential doses of the medication would be proximate the distal end 1120 of the barrel 1130 and the dosing segment 1110 corresponding to the last dose would be relatively closer to the proximal end 1135. The medication within the vial may be drawn into the syringe 1115 immediately prior to administering of the sequential doses. In such embodiments, the plunger rod 1150 may remain inside the syringe barrel 1130 until the medication is drawn into the syringe 1115. Either approach saves valuable time for the operator relative to the case in which single-dose syringes are used, since these require the operator to refill the syringe from the medication vial prior to administering each sequential dose. Use of the syringe 1115 also obviates the need for the operator to externally track how many doses have actually been provided to a patient, since the volume of medication remaining in the syringe will explicitly indicate how many doses remain in the barrel 1130 relative to the full state of barrel 1130.

The disclosed sequential dosing system is also pertinent to situations in which ambulances or other mobile medical care systems must stock a limited supply of medication ready for a vast array of patient needs. These medications may have to meet the needs of a diverse population of patients and it is not feasible or practical to have multiple preparations of the same medication ready (e.g., cardiac arrest medication). One way of addressing these needs is to use color-coding in the form of, for example, multiple color bars, to represent various size patients on the same dosing device while still preserving sequential dosing function by partitioning each color bar into multiple dosing segments.

Turning now to FIG. 12, an illustration is provided of a dosing system including a pre-labeled medicine dosing/dispensing device 1200 designed to facilitate delivery of sequential doses of medication to any one of multiple different-sized patients. As shown, the dosing device 1200 is printed, labeled or otherwise marked with three color dosing bars 1204, 1206, 1208, each of which is respectively partitioned into two dosing segments 1210, 1212, 1214. In one embodiment the color dosing bars 1204, 1206, 1208 are respectively colored blue, gold and orange, with each different color being correlated with a different patient size. Each of the dosing segments 1210, 1212, 1214 identifies a volume of the medication corresponding to a given medication dose to be provided to a patient correlated with a corresponding one of the color dosing bars 1204, 1206, 1208. For example, a first dosing segment 1210a of color dosing bar 1204 corresponds to a first dose to be provide to a patient correlated with the dosing color blue, and a second dosing segment 1210b of corresponds to a second dose to be provided to the same patient.

Like the system of FIG. 11, the dosing system of FIG. 12 has particular utility in situations in which the practice of medicine requires that sequential doses of the same medicine be provided to a patient. Such situations often arise in the context of emergency treatment where available resources and time may be limited. For example, in an emergency situation involving a cardiac arrest, the same dose of a particular medicine must generally be given to the cardiac patient during each of a number of successive 3-minute intervals. In some situations, up to 20 doses of a medication must be sequentially given to a patient before the patient can be safely transported to a hospital setting for further treatment. When conventional dosing instruments are utilized in such emergency scenarios, critical time can be lost in calculating/measuring medicine dose as well as in getting different preparations of the medicine ready for administration to the patient.

These shortcomings of conventional dosing approaches can be overcome by utilizing the sequential dosing system of FIG. 12. Specifically, the dosing segments 1210, 1212, 1214 enable a predetermined number (2 in the case of FIG. 12) doses of a medication to be prepared in advance and sequentially delivered to a patient through the device 1200. In one embodiment an operator of the dosing device 1200 need not perform any mathematical calculations in order to arrive at a correct sequence of dosages to be delivered to a patient. For example, once a parameter of the patient (e.g., weight or length) has been correlated to a particular dosing color (blue, gold or orange in the case of FIG. 12), a dosing device 1200 having a color dosing bar 1204, 1206, 1208 having a color the same as the dosing color correlated with the patient is selected. The dosing segments 1210, 1212, 1214 of the one of the color dosing bars 1204, 1206, 1208 correlated with the patient then effectively serve to inform the operator of the dispensing device of the proper volumes of medication to be administered in each successive dose in light of the patient's size, concentration of the medication, and desired medication dose (e.g., mg/kg of body weight) without requiring the operator to engage in any calculations. This sequential delivery of multiple, pre-prepared doses of medication through a single instrument in a manner not requiring a medical professional to engage in mathematical calculations or the like to determine dosing levels is not possible using conventional syringes or other conventional drug delivery devices.

Referring to FIG. 12, the medicine dosing device 1200 according to one embodiment is a syringe 1215 that includes a proximal end 1225 and a distal end 1220 opposite the proximal end. The syringe includes a vessel, such as a syringe barrel 1230 for holding therein a medicine that is to be dispensed, and a plunger 1250 that extends proximally from an opening located at the proximal end 1235 of the syringe barrel to the proximal end of the plunger at the proximal end 1225. The syringe barrel 1230 and plunger 1250 are both manufactured from material such as plastic, glass or any other suitable transparent medical grade material that is inert or will not disrupt the chemical balance of the fluid inside.

As illustrated in FIG. 12, the syringe barrel 1230 is elongate and substantially cylindrical and includes a distal end 1231 and a proximal end 1235. A chamber capable of receiving the plunger 1250 and retaining a fluid therein is defined by the inner circumferential surface of the 1230 barrel between the distal and proximal ends 1231 and 1235. A flange 1233, which can serve as a finger grip to provide for an easier handing of the syringe, is integrally formed with the proximal end of the barrel and defines an opening for receiving the plunger 1250. Proximate this opening, along the inner surface of the barrel, may be a ridge (not shown), that prevents the plunger from slipping out of the barrel once it is engaged with the barrel.

The opening defined by the flange 1233 is in communication with the chamber of the syringe 1215 and an orifice located at the distal end 1220 of the syringe barrel. A tip 1240 for attaching a needle, nozzle or tubing for expelling the liquid contained within the syringe barrel is integrally formed with the distal end 1220 of the barrel and in communication with the orifice. In some embodiments, the tip 1240 may be configured based on the type of drug that the syringe is used to deliver. For example, oral tips may be used on syringes configured for medicines that are oral, and in particular, the oral tip may be different from an intravenous ("IV") or intermuscular ("IM") tip, thereby ensuring that the medicine is delivered by the right route. Similarly, syringes configured for IV and IM drugs may be configured with IV and IM tips, respectively, such that they, too, can only be delivered via the right route.

In one embodiment the barrel 1230 is marked with a reference line 1260 (zero line). In cases in which the syringe barrel 1230 is pre-filled with medication, syringe doses may be calculated from the proximal end 1235 of the barrel 1230 or from the reference line 1260. Sequential doses may then be delivered to a patient where each dose comprises a volume of medication corresponding to one of the dosing segments 1210, 1212, 1214.

If the syringe 1215 is provided to an operator in an empty state, the syringe 1215 would be filled by the operator with medication from, for example, a medication vial. In this case the orientation of the dosing bars 1204, 1206, 1208 would be reversed relative to the orientation shown in FIG. 12. That is, the dosing bars 1204, 1206, 1208 would be oriented such that the dosing segment 1210, 1212, 1214 corresponding to the first of multiple sequential doses of the medication would be proximate the distal end 1220 of the barrel 1230 and the dosing segment 1210, 1212, 1214 corresponding to the last dose would be relatively closer to the proximal end 1235. The medication within the vial may be drawn into the syringe 1215 immediately prior to administering of the sequential doses. In such embodiments, the plunger 1250 may remain inside the syringe barrel 1230 until the medication is drawn into the syringe 1215. Either approach saves valuable time for the operator relative to the case in which single-dose syringes are used, since these require the operator to refill the syringe from the medication vial prior to administering each sequential dose. Use of the syringe 1215 also obviates the need for the operator to externally track how many doses have actually been provided to a patient, since the volume of medication remaining in the syringe will explicitly indicate how many doses remain in the barrel 1230 relative to the full state of barrel 1230.

Syringe with Prophylaxis and Treatment Dosing Indicators

Figure 13:
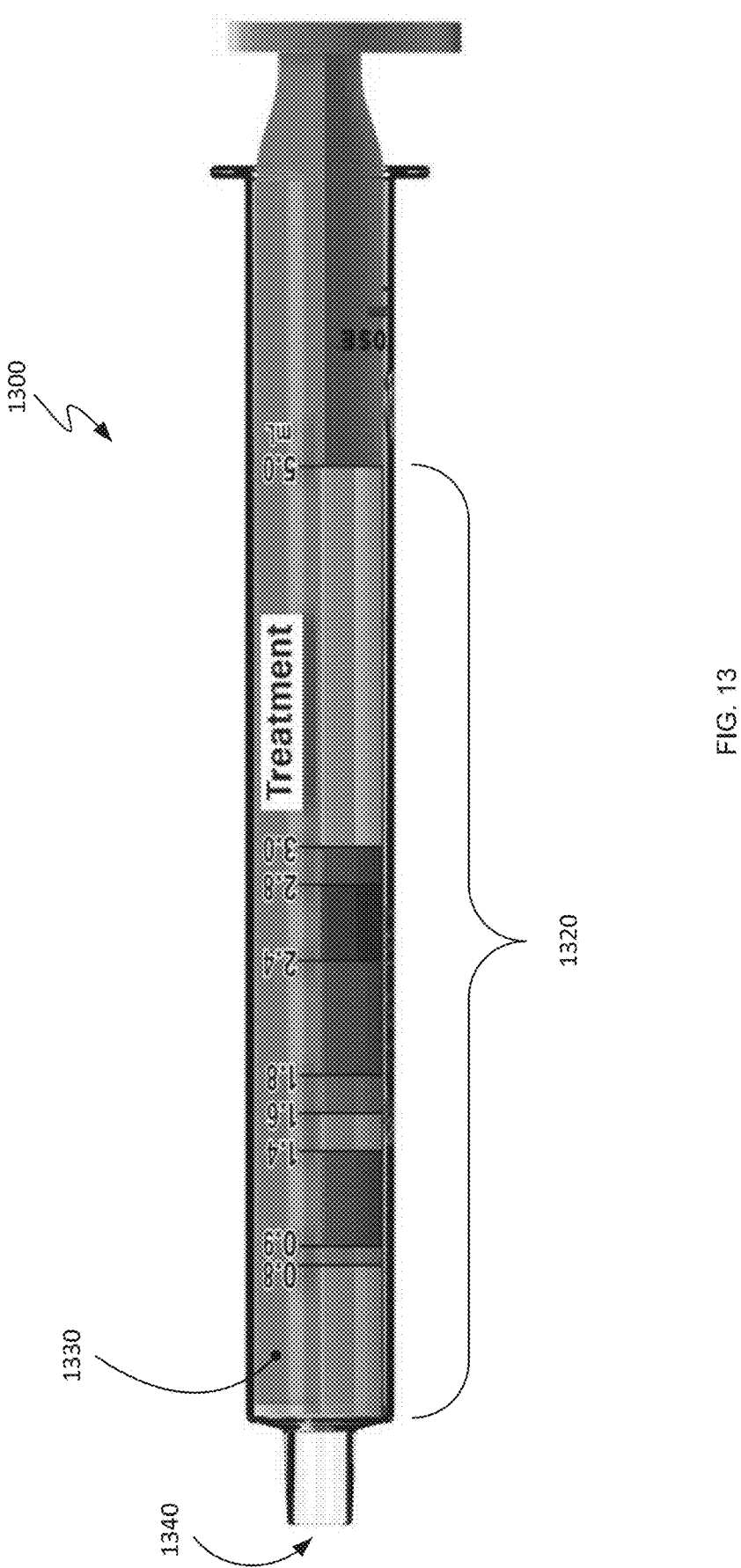
Figure 14:
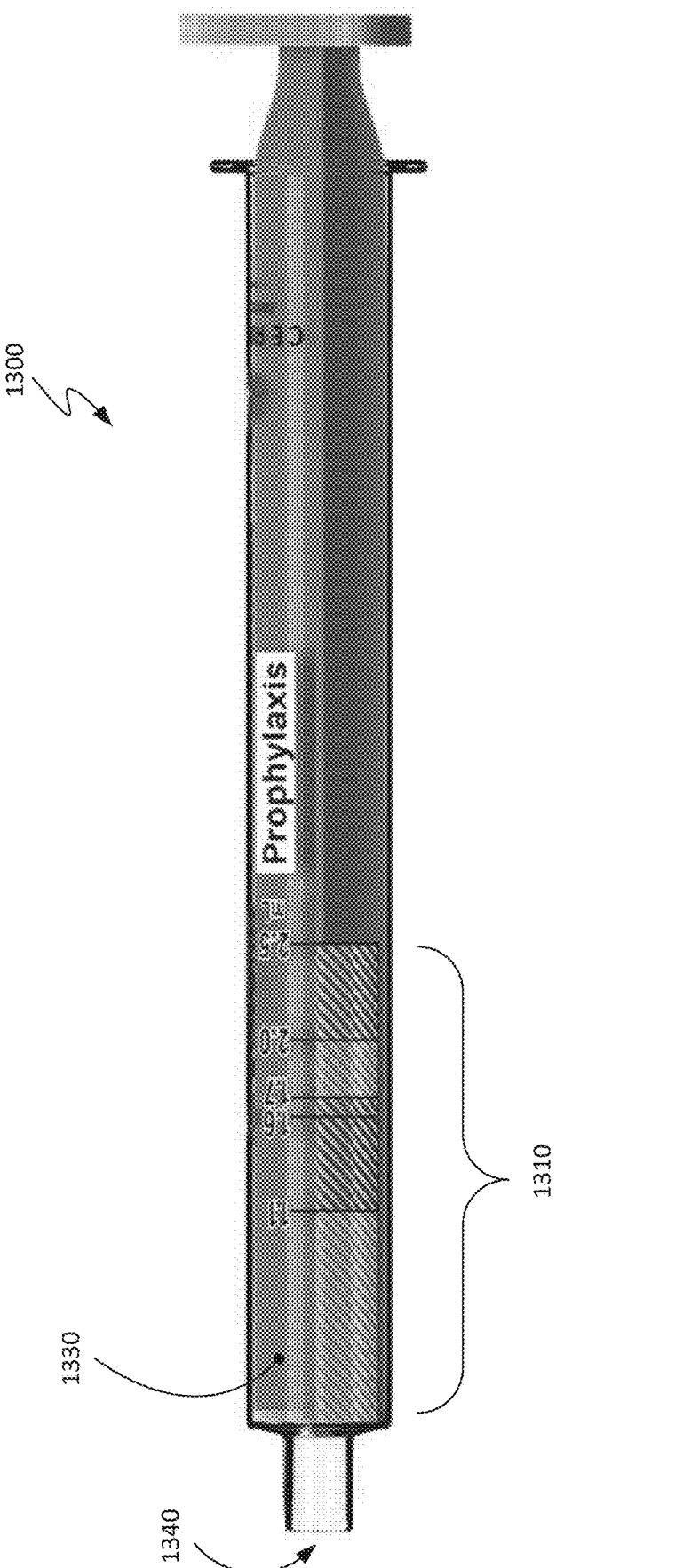
Figure 15:
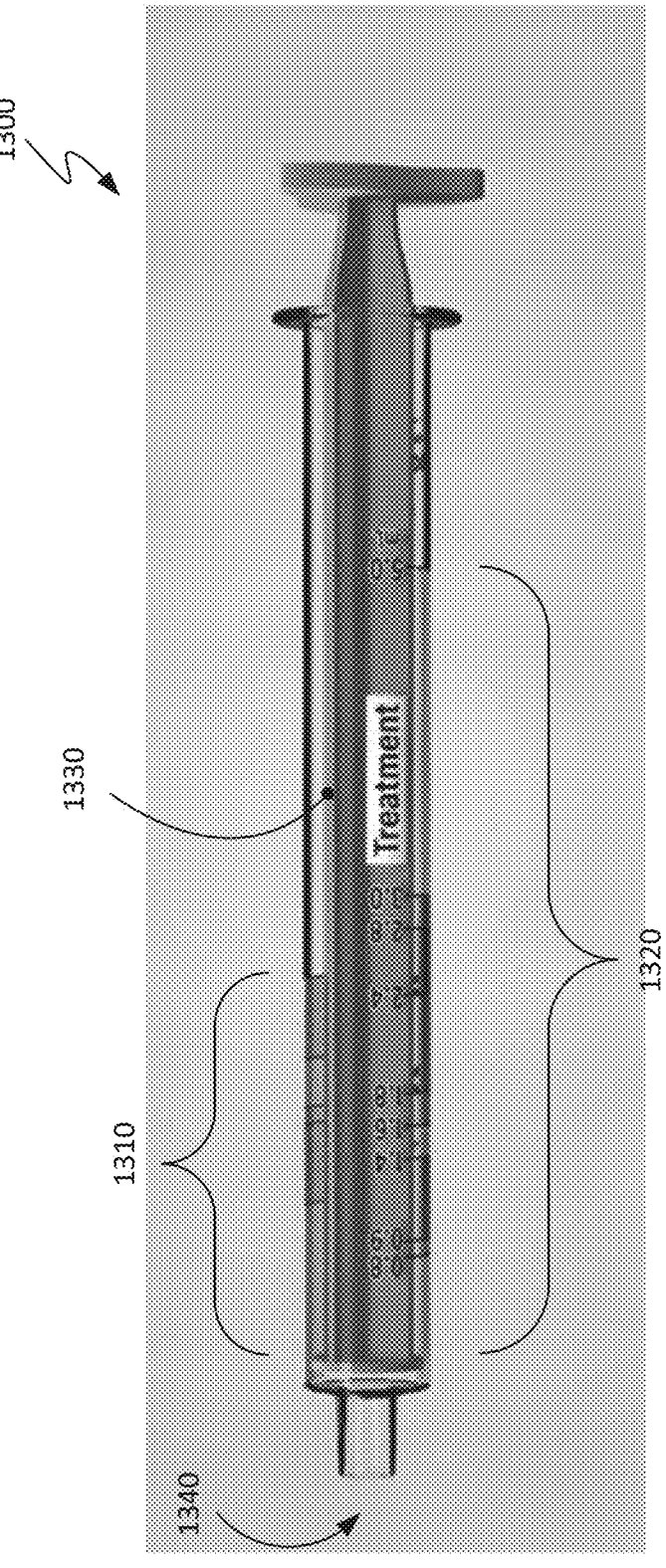
Figures 16, 16A, 16B, 16C, 16D:
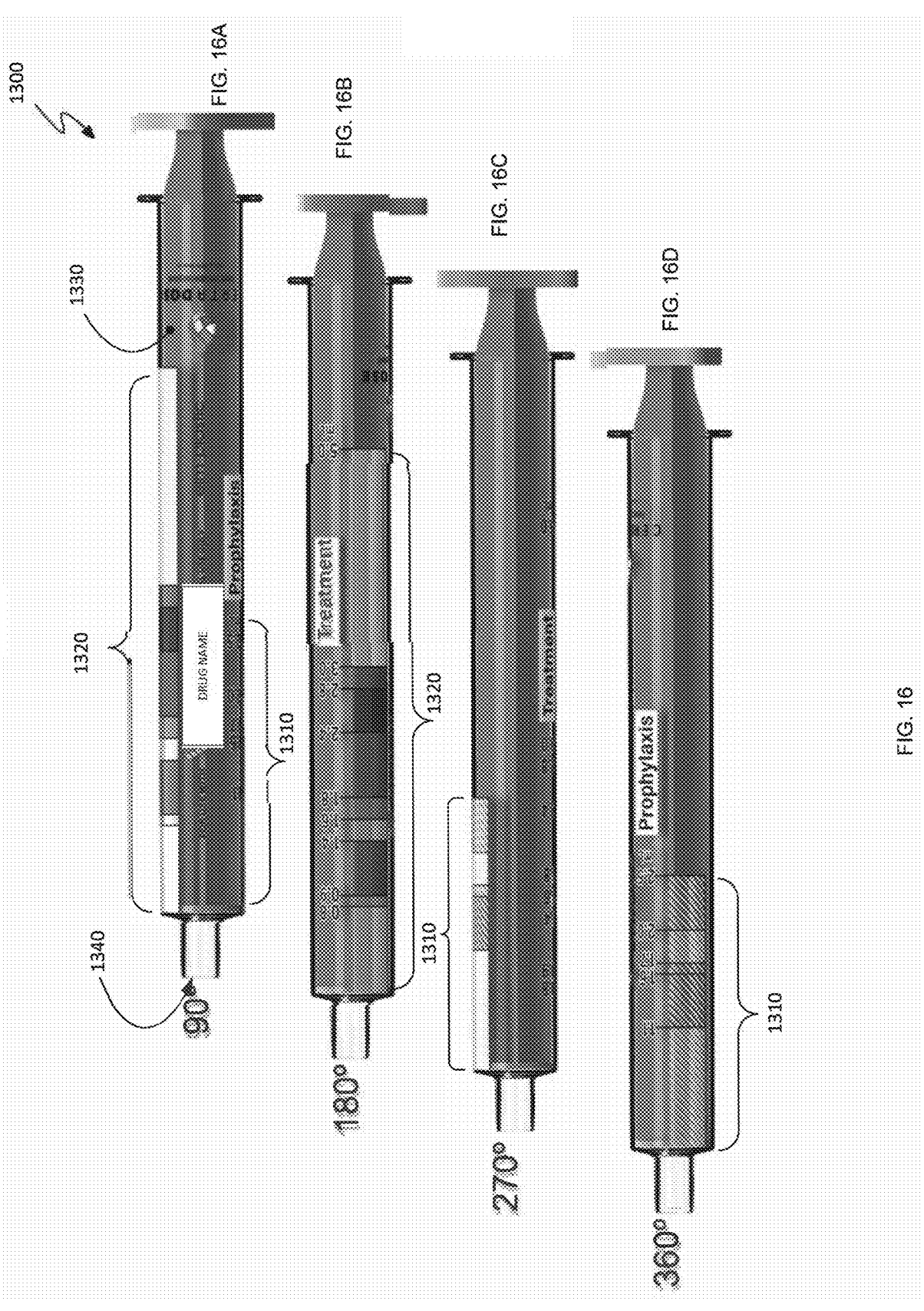
Figures 17A, 17B:
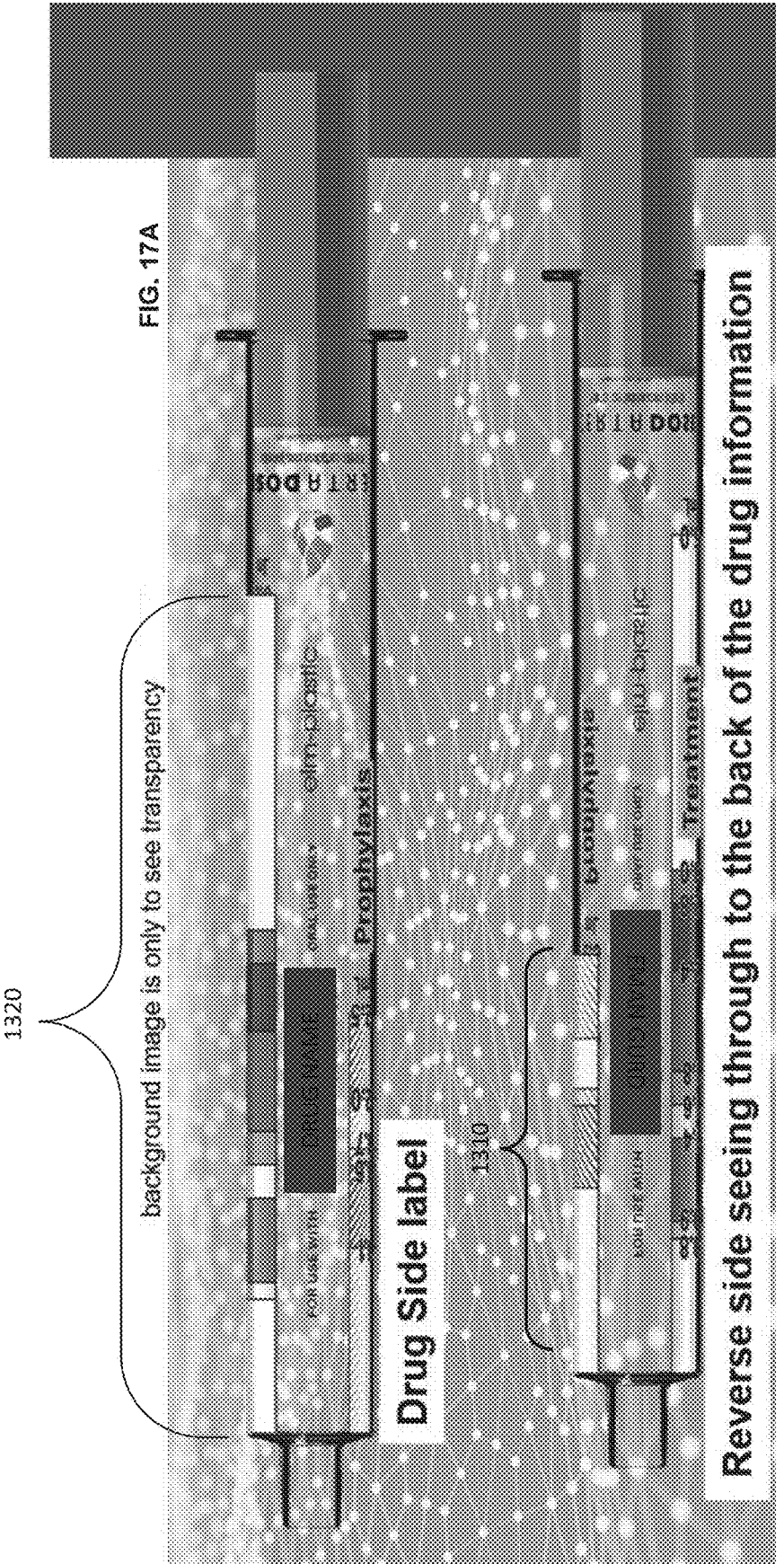

Attention is now directed to FIGS. 13-17, which depict a medicine dispensing device in the form of a syringe 1300 configured to deliver either or both of treatment dosages and prophylaxis dosages of a particular drug. As shown, the syringe 1300 includes a first series of color-coded zones of varying widths 1310 corresponding to prophylaxis dosages and a second series of color-coded zones of varying widths 1320 corresponding to treatment dosages. In the embodiment of FIG. 13 the first series of color-coded zones 1310 and the second series of color-coded zones 1320 are separated by approximately 180° on an external surface of a barrel 1330 of the syringe 1300. Each of the color-coded zones within the first series of zones 1310 and the second series of zones 1320 corresponds to a pre-determined dose of the drug that is correlated to one of the physical characteristics of a patient. The first series of zones 1310 and the second series of zones 1320 are each marked such that the smallest dose of the drug to be administered corresponds to a color-coded zone that is proximate an opening 1340 through which the particular drug is to be dispensed.

Figures 18A, 18B:
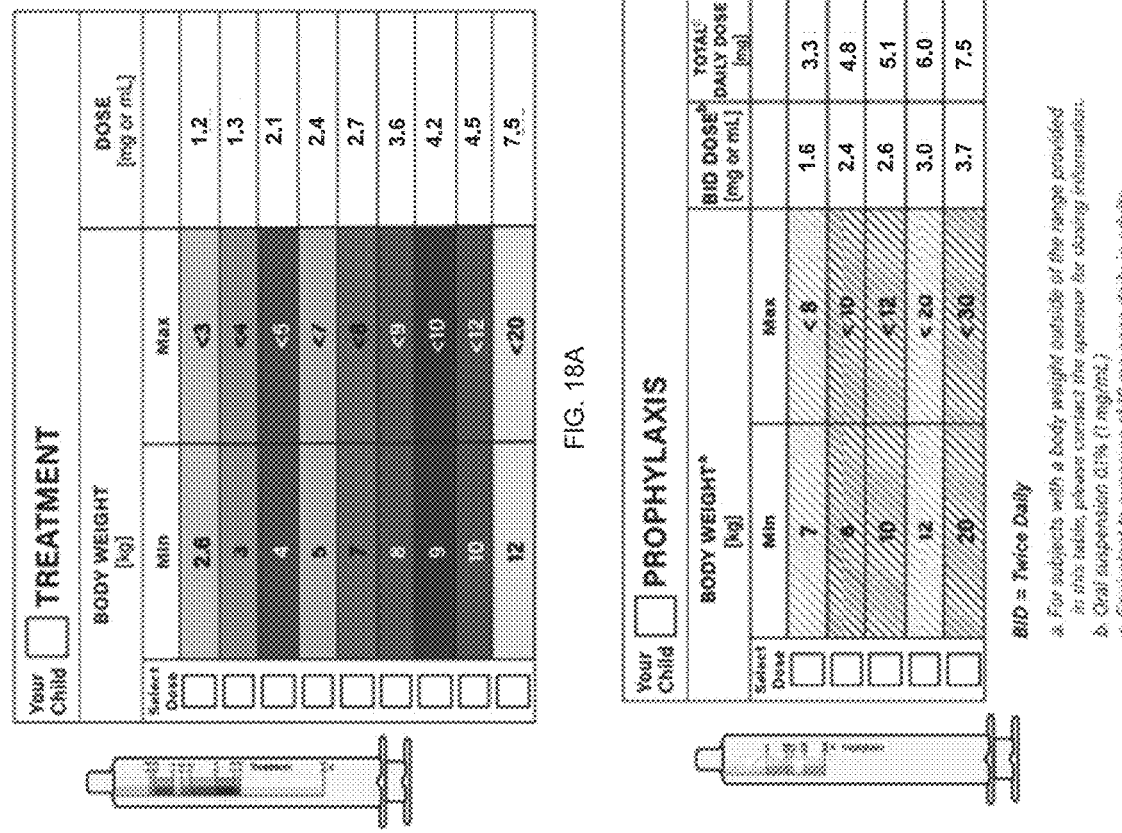
FIGS. 18A and 18B are exemplary tables identifying prophylaxis or treatment doses corresponding to a patient's color zone.

The syringe 1300 advantageously enables both prophylaxis and treatment doses of a drug to be given from the same syringe. In this case the medication concentration in the syringe 1300 is the same for prophylaxis and treatment applications, but different dosage levels will typically be prescribed for prophylaxis and treatment. In a typical usage scenario, a doctor or health care provider will instruct a caregiver which dosing option (i.e., prophylaxis or treatment) is needed and instructs the caregiver to determine the color zone associated with the patient. This enables the caregiver to fill the syringe with either the prophylaxis or treatment dose corresponding to the patient's color zone by consulting the dosing tables of FIGS. 18A and 18B (which are for illustrative purposes only and are not associated with a particular drug) and administer the corresponding dose to the patient using the syringe.

Dispensing Device with Multi-Shade Color Bands

Figures 20A, 20B:
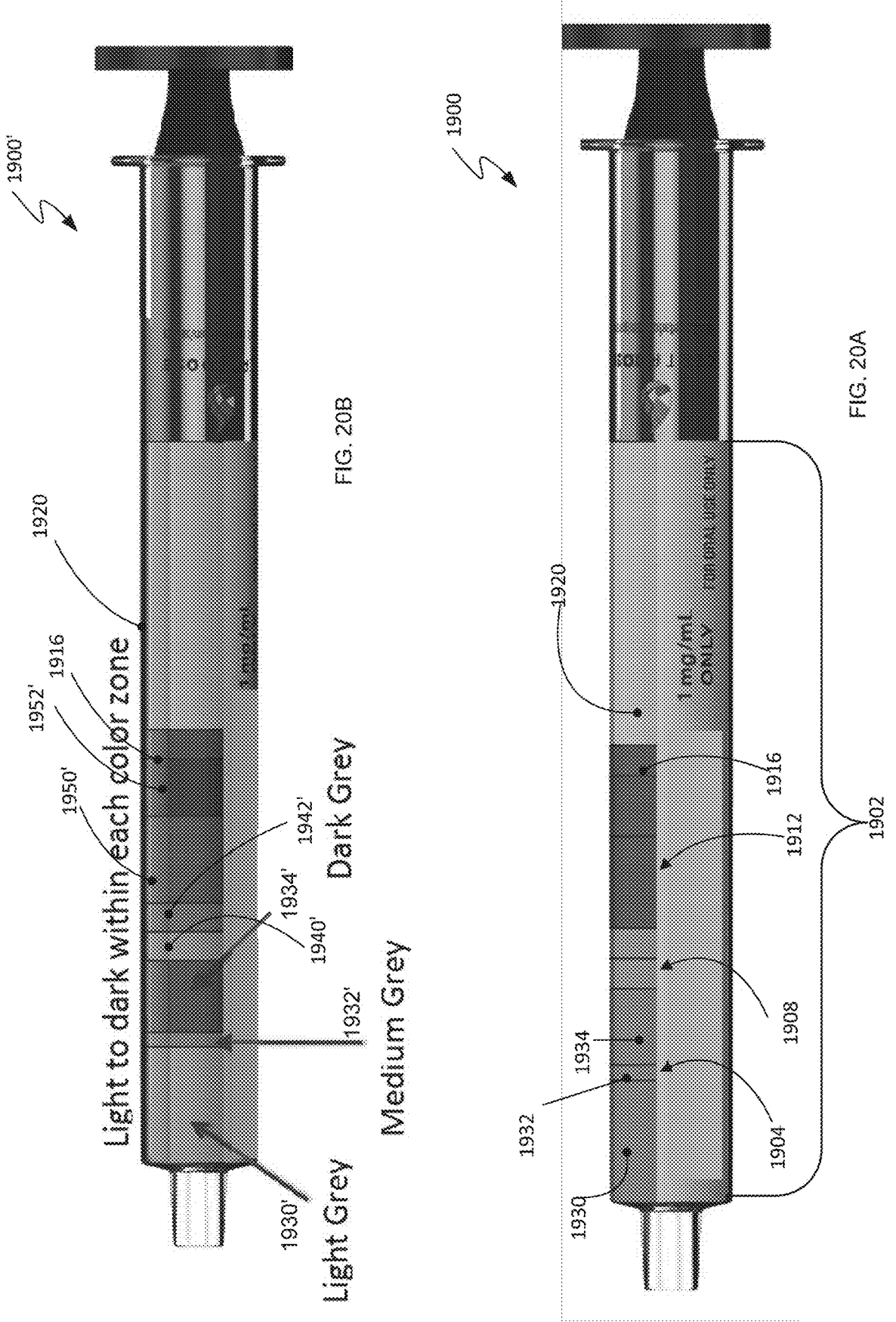

Turning now to FIGS. 19 and 20, a syringe 1900 having a series of multi-segment color-coded bands of varying widths 1902 is illustrated. As shown, the syringe 1900 includes a grey dosing band 1904, pink dosing band 1908, red dosing band 1912, purple dosing band 1916 and a yellow dosing band 1920. In one embodiment certain of the dosing bands may be partitioned into multiple segments. For example, the grey dosing band 1904 may be partitioned into a first grey segment 1930, a second grey segment 1932 and a third grey segment 1934, each corresponding to a different range of patent weight or other physical characteristic of the patent. In the embodiment of FIGS. 19A and 20A, each of the first grey segment 1930, second grey segment 1932 and third grey segment 1934 are of the same shade of grey. In the embodiment of FIGS. 19B and 20B, the grey dosing band 1904 includes a light grey segment 1930', a medium grey segment 1932', and a dark grey segment 1934'. Similarly, in the embodiments of FIGS. 19B and 20B, the pink dosing band 1908 includes a light pink segment 1940' and a dark pink segment 1942'. The red dosing bank 1912 may be similarly partitioned into a light red segment 1950' and a dark red segment 1952'.

Syringe System Providing Dosing Indications for Multiple Different Conditions

As is known, in particular cases drug manufacturers may offer certain drugs in only a single concentration. For example, it may not be feasible for a drug manufacturer to provide multiple concentrations of a drug used to treat a rare medical condition. Similarly, a given drug (e.g., penicillin) may be used to treat relatively more serious conditions (e.g., pneumonia) in addition to less serious conditions (e.g., an ear infection). Since a more serious condition may require a larger dose than a less serious condition, a color-coded syringe correlated to a physical parameter of a patient such as those described herein may be unable to simultaneously accommodate the dosing schemes for both the more and less serious conditions.

For example, consider a situation in which penicillin is being used to treat two twin children, one having been diagnosed with an ear infection and the other with pneumonia. Assume each of the twins weighs 10 kg. and that the relevant pharmacy has only one concentration of penicillin for children (e.g., 100 mg per 5 ml). In this case a doctor may order 100 mg of penicillin per day for the one of the twins having an ear infection ("twin A") and 200 mg of penicillin per day for the twin diagnosed with pneumonia ("twin B"). So twin A would receive 5 ml of penicillin per day and twin B would receive 10 ml. per day. Even though twin A and twin B weigh the same and the penicillin concentration for each is the same, each would receive a different dose (volume of medication) since dosing is dependent upon the underlying diagnosis and not just the size of the child or concentration of the medication.

In accordance with one aspect of the disclosure, one way that a pharmaceutical company or other provider of medicine could address this situation would be to provide a syringe having dual dosing indications or scales on the same syringe. Each dosing indication on the syringe would be associated with a particular medical condition or diagnosis and would have its own legend (e.g., color coding or marking scheme). In this type of system, the colors within each dosing indication scheme could still match a standard system for weight, but hash marks or other indicia could be used to differentiate the scales.

Figure 21:
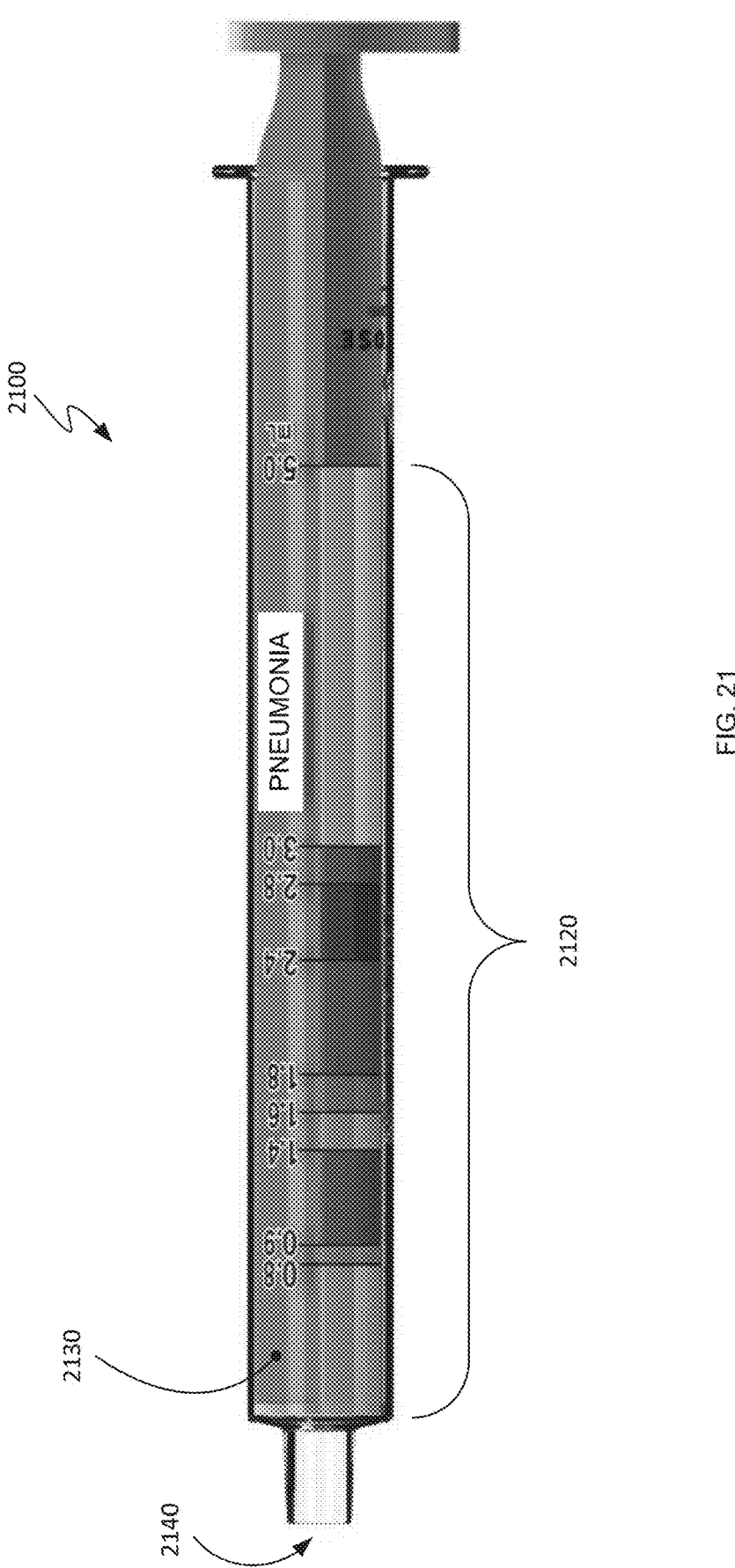
FIGS. 21-22 depict a medicine dispensing device in the form of a syringe configured with dosing indications associated with different medical conditions.
Figure 22:
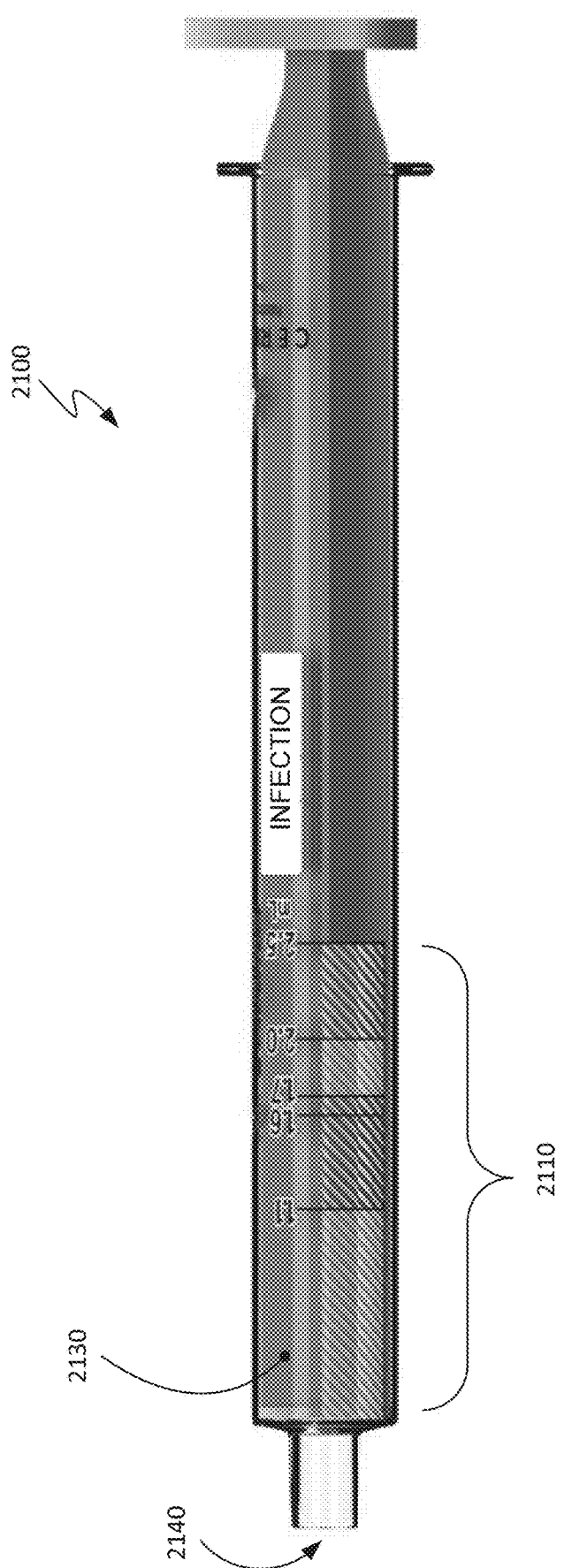

Attention is now directed to FIGS. 21-22, which depict a medicine dispensing device in the form of a syringe 2100 configured with dosing indications associated with different medical conditions. In this way the same syringe 2100 can be used to deliver a particular drug to treat the different medical conditions. As shown, the syringe 2100 includes a first series of color-coded zones of varying widths 2110 corresponding to dosages for a first medical condition and a second series of color-coded zones of varying widths 2120 corresponding dosages associated with a second medical condition. In the embodiment of FIGS. 21-22, the first series of color-coded zones 2110 and the second series of color-coded zones 2120 are separated by approximately 180° on an external surface of a barrel 2130 of the syringe 2100. Each of the color-coded zones within the first series of zones 2110 and the second series of zones 2120 corresponds to a pre-determined dose of the drug that is correlated to one of the physical characteristics of a patient. The first series of zones 2110 and the second series of zones 2120 are each marked such that the smallest dose of the drug to be administered corresponds to a color-coded zone that is proximate an opening 2140 through which the particular drug is to be dispensed.

Figures 23A, 23B:
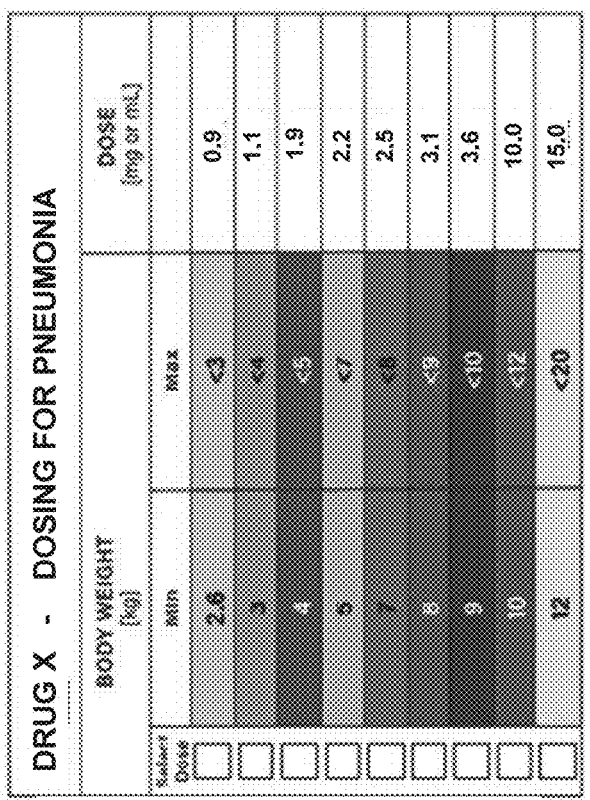
FIGS. 23A and 23B are exemplary dosing tables for use with the syringe of FIGS. 21-22 which advantageously enable the syringe to deliver the same drug for different medical conditions having different dosing requirements.

As may be appreciated from the exemplary dosing tables depicted in FIGS. 23A and 23B, the dual indications on the syringe 2100 advantageously enable the same syringe 2100 to deliver the same drug for different medical conditions having different dosing requirements. In a typical usage scenario a caregiver will determine the color zone associated with a patient and determine the appropriate dose to be dispensed by consulting the one of the tables in FIGS. 23A and 23B applicable to the patient's medical condition (the values within the tables of FIGS. 23A and 23B are for illustrative purposes only and are not associated with a particular drug). This enables the caregiver to fill the syringe with the dose corresponding to the patient's color zone and medical condition or diagnosis and administer the corresponding dose to the patient using the syringe 2100.

Figure 24:
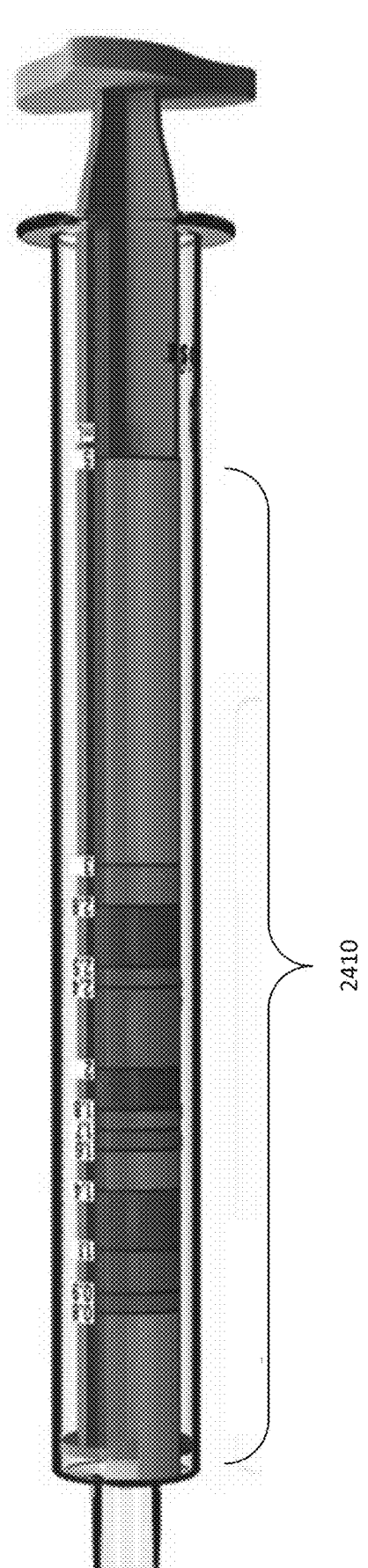
FIG. 24 illustrates a syringe having a single color-coded dosing scale.
Figures 25A, 25B:
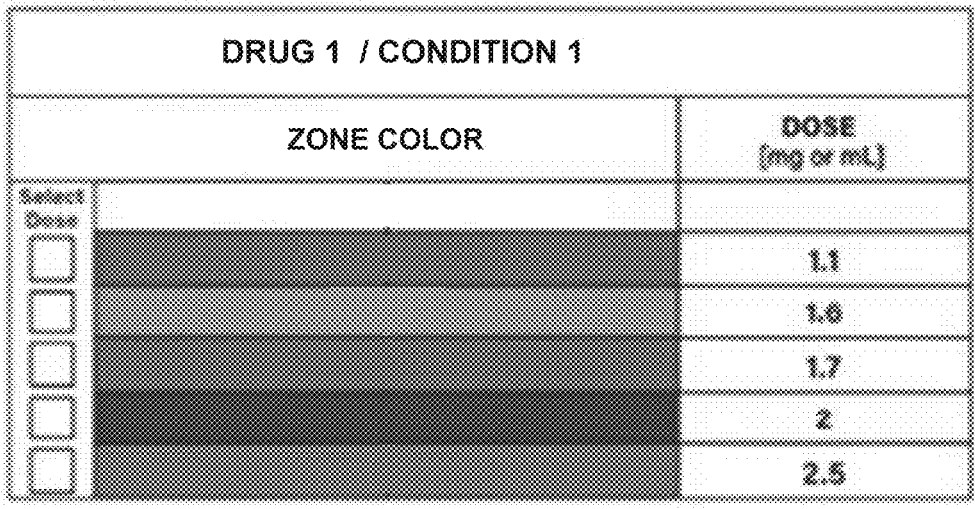
FIGS. 25A and 25B are different dosing tables for a particular drug for use in conjunction with the syringe of FIG. 24 in connection with dosing for different medical conditions.

FIGS. 24-25 illustrate an alternative approach for using a single syringe to provide doses of the same drug for different medical conditions or diagnoses. Specifically, FIG. 24 illustrates a syringe 2400 having a single color-coded dosing scale 2410. FIGS. 25A and 25B are different dosing tables 2502 and 2504, respectively, for a particular drug for use in conjunction with the syringe 2400 in dosing for different medical conditions. The colors within the dosing tables 2502, 2504 of FIGS. 25A and 25B correspond to the colors within the color-coded dosing scale 2410. In this way the dosage volumes within the dosing tables 2502, 2504 of FIGS. 25A and 25B are matched to corresponding color-coded dosing zones of the scale 2410. In the embodiment of FIGS. 24 and 25, the color-coded zones of the scale 2410 and dosing tables 2502, 2504 of FIGS. 25A and 25B could be agnostic relative to patient weight. That is, the dosing tables 2502, 2504 of FIGS. 25A and 25B could simply be used to map dosing volumes to different color-coded volume zones included within the scale 2410 on syringe 2400. In one embodiment a physician, pharmacist, nurse or other authorized medical personnel would determine the zone corresponding to a patient's size or weight and communicate this zone information or color to the patient or caregiver responsible for delivering the drug dispensed by the syringe 2400.

Alternatively, the scale 2410 could correspond to a color-coded dosing scale based on weight that is peculiar to a particular drug. In this case the tables of FIGS. 25A and 25B could be used to determine doses for different medical conditions provided that the color-coded zone within the scale 2410 corresponding to the patient/s size or weight is known.

Attention is now directed to FIGS. 26A-C and FIGS. 27A-C, which illustrate alternate embodiments of dosing systems in which color is used to represent dosing volume for multiple scenarios in a manner that is not explicitly tied to patient weight. The embodiments of FIGS. 26A-C and FIGS. 27A-C may find application in, for example, situations in which it is desired to provide volumetric dosing indications for multiple conditions or scenarios (e.g., prophylaxis and treatment) where the same volume may be prescribed for patients of different size under different scenarios.

Figures 26A, 26B:
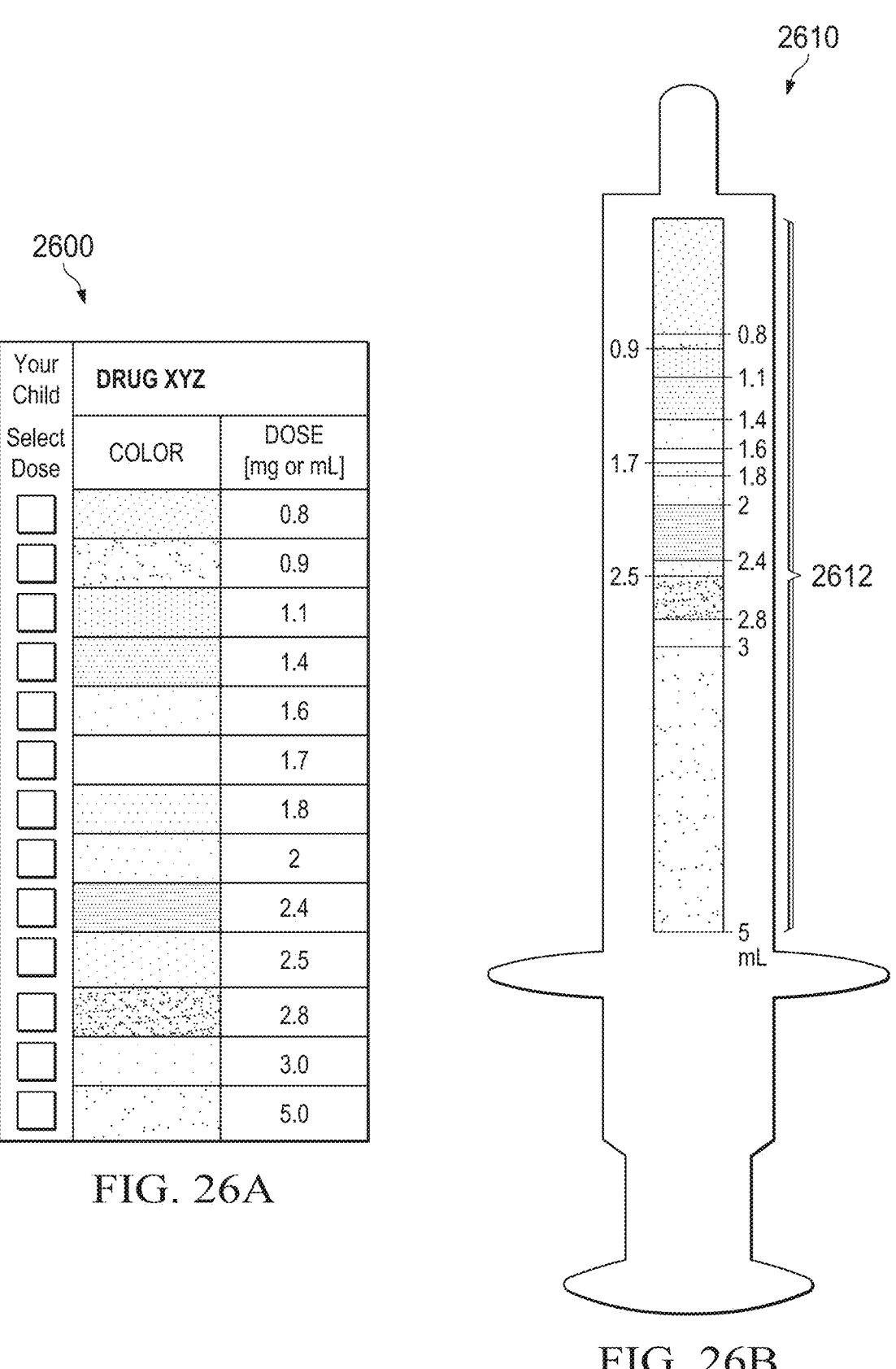
FIGS. 26A-26C is a first embodiment of a dosing system in which color is used to represent dosing volume for multiple scenarios or medical conditions.
Figure 26C:
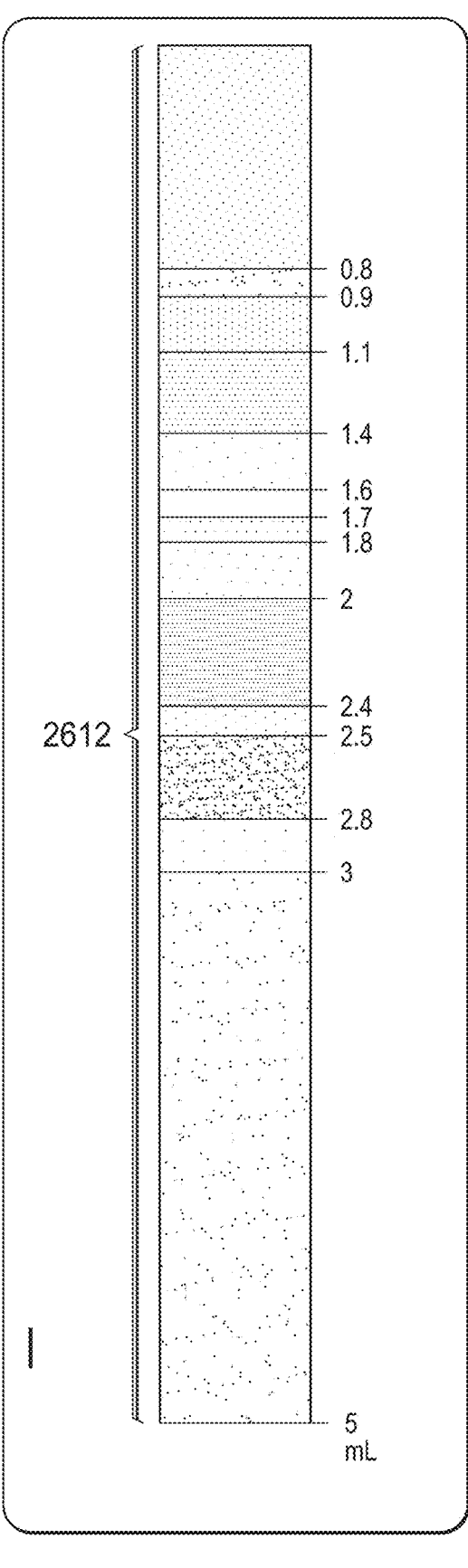

Referring to the dosing system of FIGS. 26A-26C, FIG. 26A illustrates a dosing table 2600 for use with a color-coded syringe 2610 depicted in FIG. 26B. A color-coded label 2612 attached to an exterior surface of the barrel of the syringe 2610 is shown flattened out in FIG. 26C. Although the dosing table 2600 explicitly references only volumes associated with color-coded zones, each color-coded zone may implicitly be correlated with patient weight with respect to a given medical condition. In this embodiment a doctor, pharmacist or other medical professional would assign a given dose (i.e., color and/or volume) for a given patient with respect to a given condition (e.g., prophylaxis or treatment of a particular disease or condition). As an example, consider the case in which a 14 kg child is prescribed a treatment dose of 1.4 ml (1 mg/kg dose) and a 28 kg child is prescribed a prophylaxis dose of 1.4 ml (0.5 mg/kg). As shown, this corresponds to the purple zone in the dosing table of FIG. 26A. The patient or caregiver would then utilize the syringe of FIG. 26B to then administer the child a dose of medication corresponding to the purple zone (1.4 ml).

The dosing system of FIGS. 26A-C, in which correlation with weight or patient size is implicit rather than explicit, is advantageously flexible from a manufacturing and medical indication perspective. Moreover, the system improves dosing accuracy by limiting the number of possible doses on a standard graduated syringe to the ranges that are commonly used for one or more indications, and correlates these to color. This serves as a cognitive forcing strategy designed to reduce dosing errors in a manner consistent with that advocated by, for example the Institute of Safe Medical Practice (ISMP).

Figures 27A, 27B:
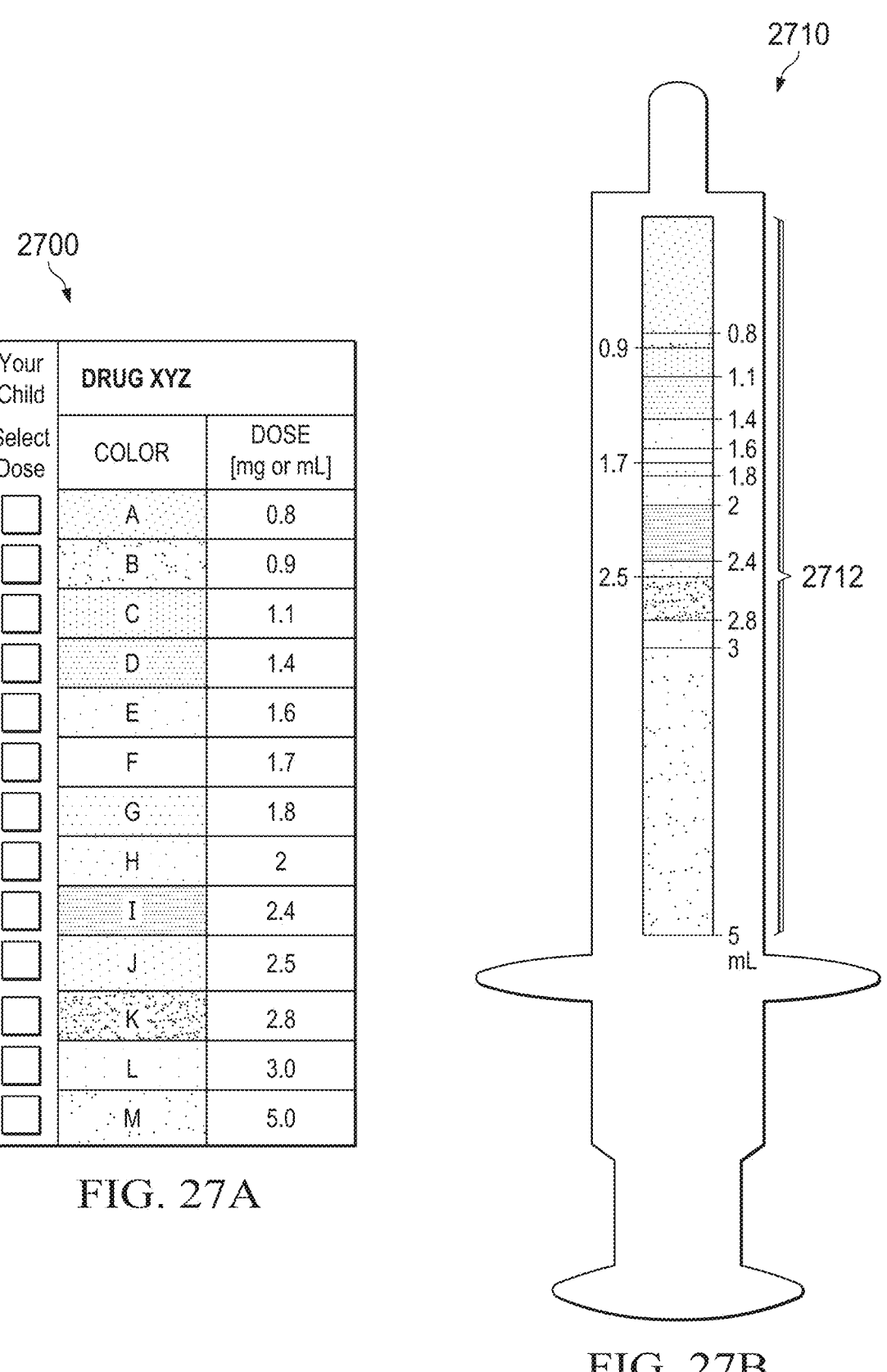
FIGS. 27A-27C is a second embodiment of a dosing system in which color is used to represent dosing volume for multiple scenarios or medical conditions.
Figure 27C:
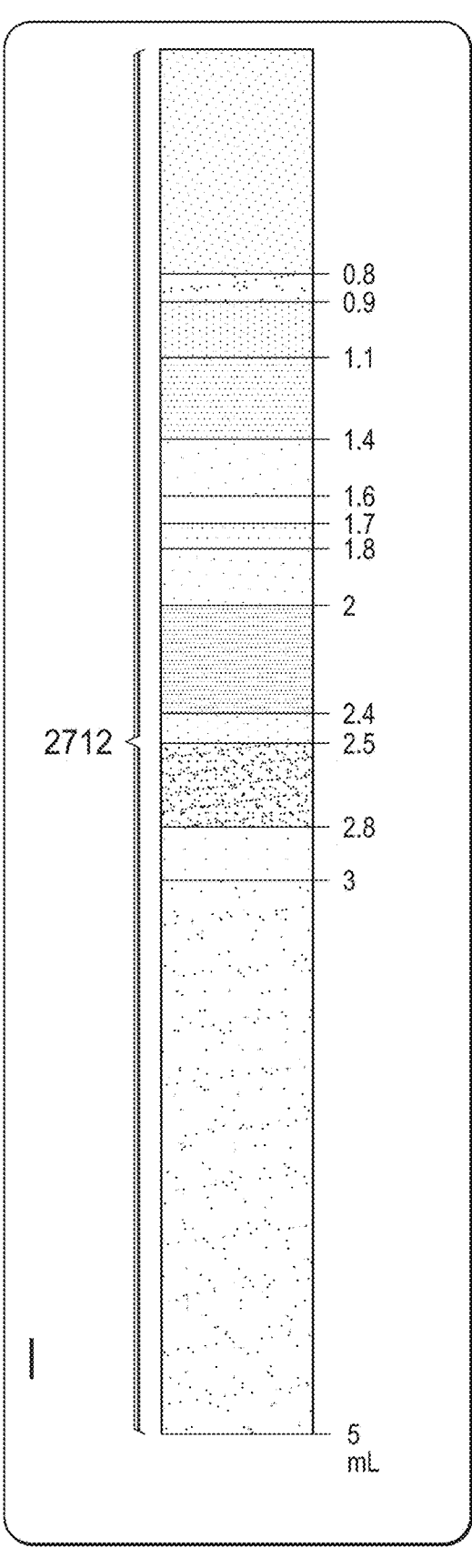

Referring now to the dosing system of FIGS. 27A-27C, FIG. 27A illustrates a dosing table 2700 for use with a color-coded syringe 2710 depicted in FIG. 27B. A color-coded label 2712 attached to an exterior surface of the barrel of the syringe 2710 is shown flattened out in FIG. 27C. The dosing system of FIGS. 27A-27C is substantially similar to the dosing system of FIGS. 26A-26C. However, in the dosing system of FIGS. 27A-27C the color-coded zones in the table 2700 further include alphabetic labels to further enhance dosing accuracy. For example, again considering the case of a condition requiring a dose of 1.4 ml, a physician or pharmacist could convey the dose information by prescribing a dose corresponding to one or both of zone "D" and the "purple" color zone. By specifying an alphabetic label in addition to a color zone the risk of erroneous dosing is further reduced.

Figures 28A, 28B:
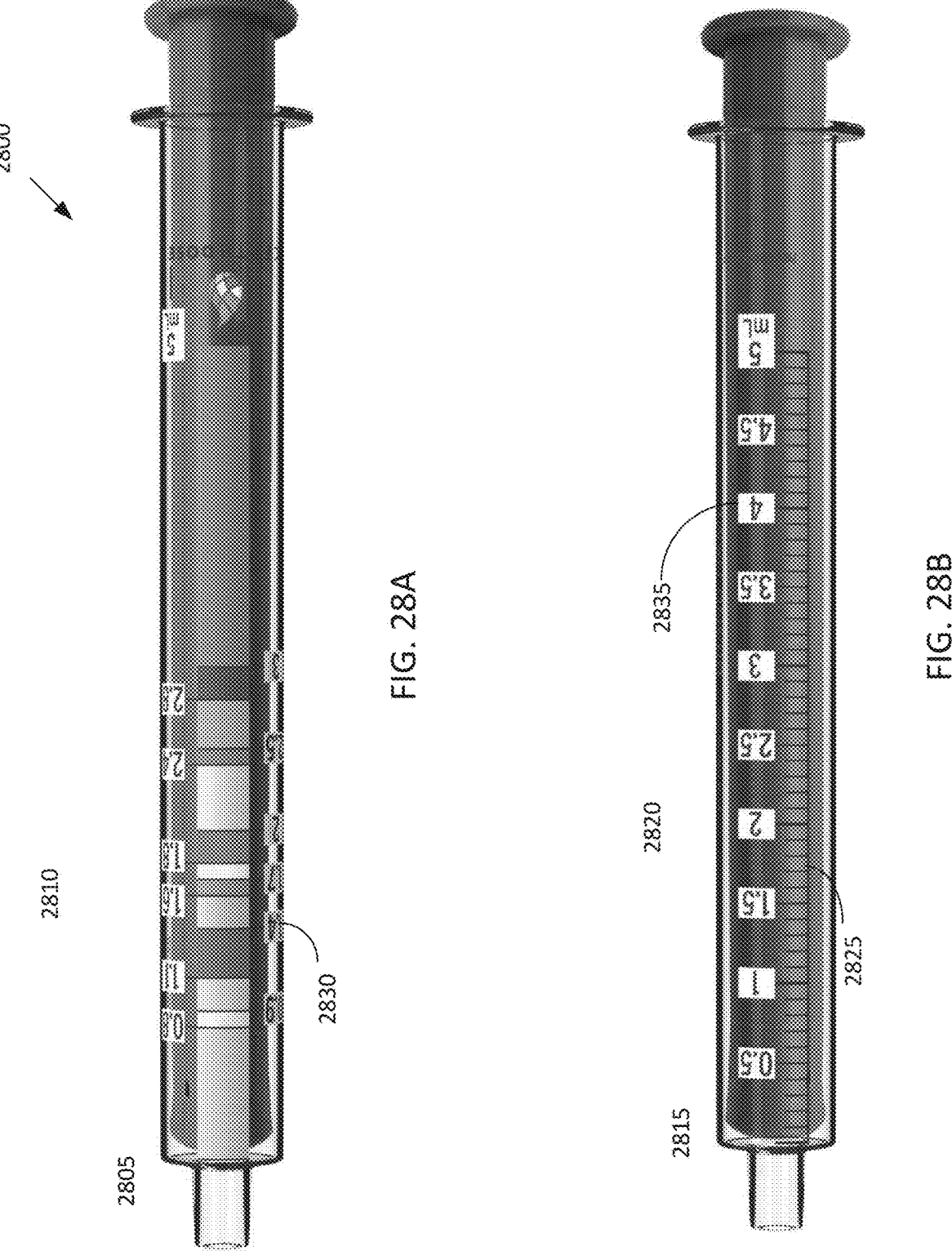
FIGS. 28A-28B show an embodiment of a medicine dispensing device according to the present disclosure having color-coded zone markings and numerical volumetric markings.

FIGS. 28A and 28B show an embodiment of a medicine dispensing device 2800 according to the present disclosure. The medicine dispensing device 2800 has a single color-coded scale 2810 on a first side 2805 and a linear volumetric scale 2820 on a second side 2815. The single-color coded scale 2810 may comprise one or more zones corresponding to dosing tables for one or more conditions. In embodiments, the single color-coded scale 2810 may correspond to two dosing tables, each dosing table being particular to one medical condition to be treated by the same drug, and colors from each of the two dosing tables may be interspersed along the single color-coded dosing scale.

As shown, the medicine dispensing device 2800 is transparent apart from the single color-coded scale 2810, the lines 2825 of the linear volumetric scale 2810, and the numeric indicators 2830 and 2835 along the single color-coded scale 2810 and the linear volumetric scale 2810, respectively. The numeric indicators 2830 and 2835 may comprise black text on an opaque white background to provide improved visual contrast of the numbers as compared to black text on a translucent background. The design of the medicine dispensing device 2800 allows a person administering a dose to see easily the drug within the device in relation to both the color code and the numeric value of the dose.

Figure 29A:
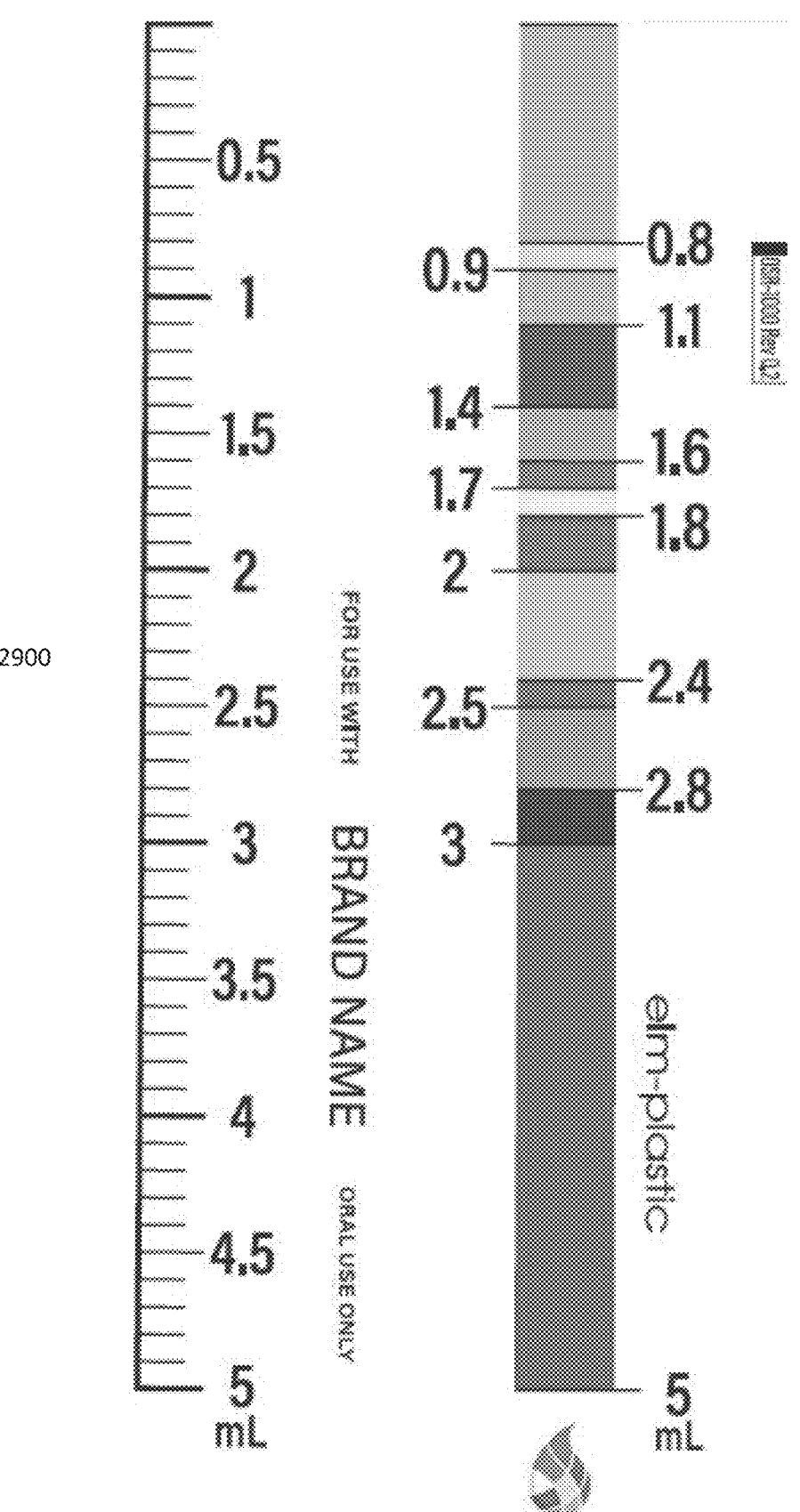

FIGS. 29A-C show a flat label 2900 which may be printed and affixed to a transparent vessel of a medicine dispensing device to manufacture one according to the present disclosure (e.g., the medicine dispensing device 2800). FIG. 29A shows a view with a white background for clarity, but in embodiments, a manufacturing process may comprise printing a label with white blocks 2910 on a transparent material as shows in FIG. 29B and then printing a color coded scale 2930 and numerals 2940 on the white blocks 2910, and printing a linear volumetric scale 2950 on the transparent material 2950. This method may be used to easily manufacture medicine dispensing devices of similar size with different color dosing scales that correspond to different drugs, different scenarios, and different conditions.

Each of the methods for printing dosing labels described above may be applied to the manufacturing of medicine dispensing devices having stair-step dosing indicators described below with reference to FIGS. 30-34G.

To summarize the overall features and functions of the medicine dispensing system previously described in FIGS. 21-29C, the dosing system is comprised of these aspects: A) a color pattern on the device (e.g., syringe), with bars of varying widths correlating to doses, B) one or more tables that have the same colors in the same order (in one table) or split up (into one or more tables), with the colors matching the colors on the syringe and correlating to a specific volume on the syringe, and C) the volume marked by a color can match the dose that is selected for a particular condition.

Dispensing Device with Stair-Step Dosing Indicators

Another aspect of the disclosure provides a medicine dispensing device having two or more "stair-step" dosing indicators on a surface thereof. The term "stair-step" refers to the visual impression of two or more linear blocks of different heights next to each other which resemble stairs. These linear blocks may be represented by wide or thin rectangular blocks, lines, or similar shapes. Each linear block may be referred to as a dosing indicator (or dosing indicia, in the plural), and may correspond to a height to which liquid medicine within the medicine dispensing device may be filled. In several of the embodiments shown herein, each of the stair-step dosing indicia correspond to a different dose of liquid medicine and do not overlap with each other. In many embodiments, each of the two or more stair-step dosing indicia are a different color from each other of the two or more stair-step dosing indicia.

Any of the methods for associating a particular color with any value described throughout this disclosure may be applied to associating a value with a particularly colored stair-step dosing indicator of the medicine dispensing devices described herein. That is, a color of a stair-step dosing indicator may be based on the various methods described in this disclosure for associating patient characteristics (e.g., height, weight, surface area, etc.) medication concentration, volumetric capacity of a dispensing device, medication indication or condition, medication type, and/or scenario. For example, the dosing tables shown and described with reference to FIGS. 25A-27C may be used to determine what color is associated with a particular dose for a patient having a given length and condition, and the color of a particular one of the stair-step dosing indicia may correspond to that particular dose. All or some of the stair-step dosing indicia on a given medicine dispensing device may correspond to a given dosing table.

An advantage of the layout of the stair-step dosing indicia of the present disclosure is that each color may be easily seen separate from each other color because they each comprise their own linear block. This layout may allow some users to more clearly differentiate between doses that are near each other and which may have just a small volume of difference between them; for example, it may be beneficial for users with imperfect vision. In embodiments, each of the stair-step dosing indicia may also have a visible, numeric volumetric indicator.

FIG. 30 shows a medicine dispensing device in the form of a syringe 3000 having two visible stair-step indicia 3010 and 3020. As shown, the lower dose stair-step indicator 3010 shows a distance to which liquid medicine may be drawn into the syringe 3000, and has a numeric volumetric indicator for 5 ml. The higher dose stair-step indicator 3020 shows a longer distance which liquid medicine may be drawn into the syringe 3000, and has a numeric volumetric indicator for 7.5 ml. Each of the stair-step indicia 3010, 3020 is a different color, and they have a space between them. The syringe 3000 itself is translucent, and the stair-step indicia 3010, 3020 may be opaque or translucent. In either case, the liquid medication may be visually aligned with the top of the desired dosing indicator to measure and/or visually confirm the proper dosage.

FIG. 31A shows a syringe 3100 with visible, numeric volumetric indicators 3102, 3104, 3106, and 3108 on a first side, and FIG. 31B shows the syringe 3100 with a plurality of stair-step indicators 3112, 3114, 3116, and 3118. In embodiments, medicine dispensing devices may have more or fewer stair-step indicators, and they may be spaced out at different intervals across the surface of the barrel of the syringe.

Figure 32:
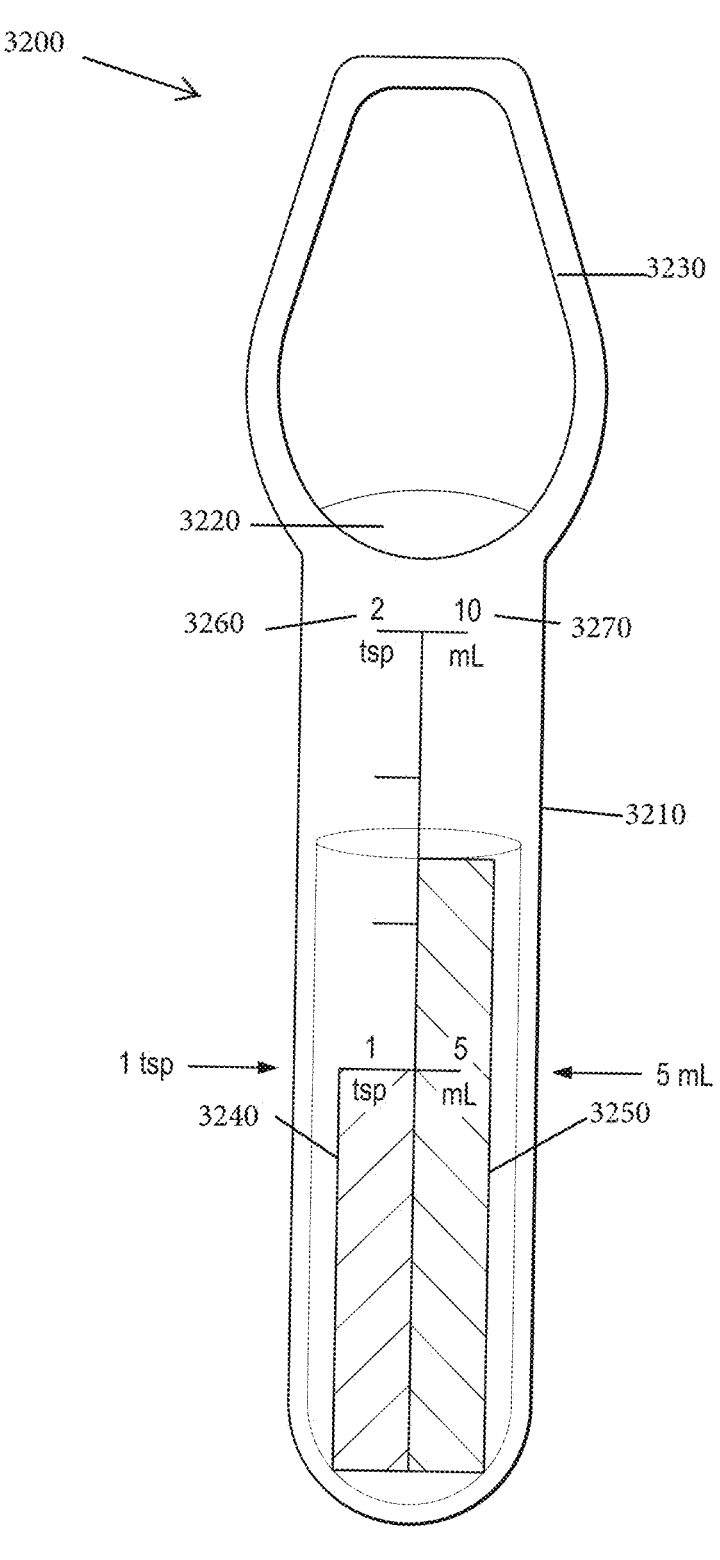
FIG. 32 illustrates a medicine dispensing device in the form of a spoon for administering liquid medication implementing stair-step dosing indicia.

FIG. 32 shows an embodiment of a medicine dispensing device in the form of a spoon 3200. The spoon 3200 has a hollow barrel portion 3210 configured to receive and hold a volume of liquid medication through a barrel opening 3220 adjacent a spoon head 3230. The hollow barrel portion 3210 may also be used as a handle of the spoon 3200 while administering the medication. The hollow barrel 3210 may be transparent or translucent and may comprise one or more stair-step indicators. In the embodiment shown, there are two stair-step dosing indicia 3240 and 3250. The hollow barrel 3210 also comprises numerical volumetric indicators 3260, 3270. An advantage of the medicine dispensing spoon 3200 is that it allows accurate dosing and visual confirmation of accurate doses for medication that is administered by spoon, which can be especially difficult to administer properly due to variations in size and lack of markings on conventional spoons.

Figure 33A:
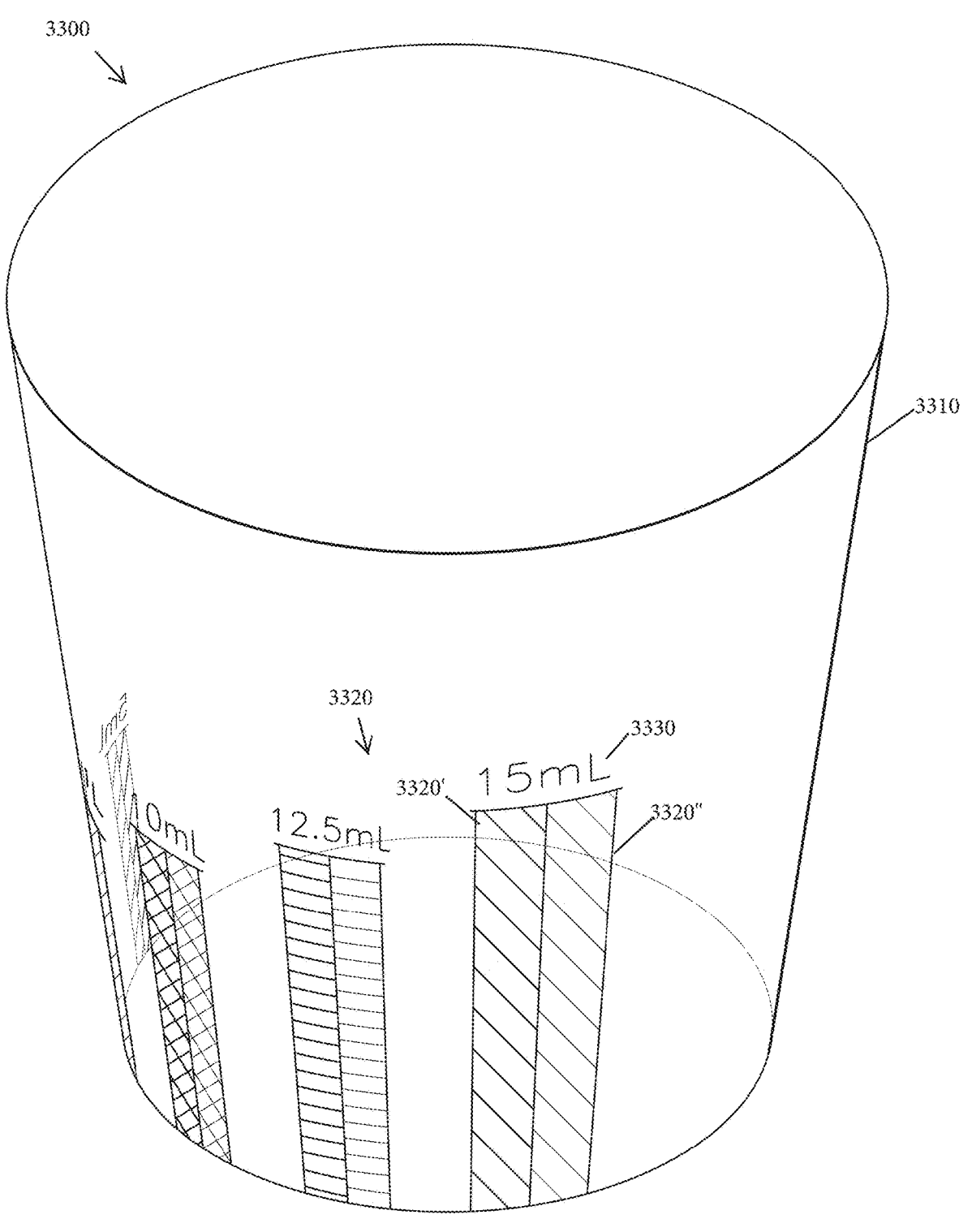
FIG. 33A shows a front perspective view of a medicine dispensing device of the present disclosure having a set of stair-step dosing indicia comprising different colors and two transparency levels for each dose.

Attention is now directed to FIGS. 33A-G, which depicts a first embodiment of a medicine dispensing device 3300 for administering a liquid medicine. FIG. 33A is a front perspective view of the medicine dispensing device 3300, which includes a cup 3310 configured to contain a liquid medicine to be dispensed to a patient. The cup includes a side wall, a circular bottom element and an open top. As shown in FIG. 33A, a plurality of stair-step dosing indicia 3320 are spaced around a circumference of a surface of the side wall of the cup. Each dosing indicia 3320 is of a different height relative to a reference level and corresponds to a different dose of the liquid medicine.

Figure 33B:
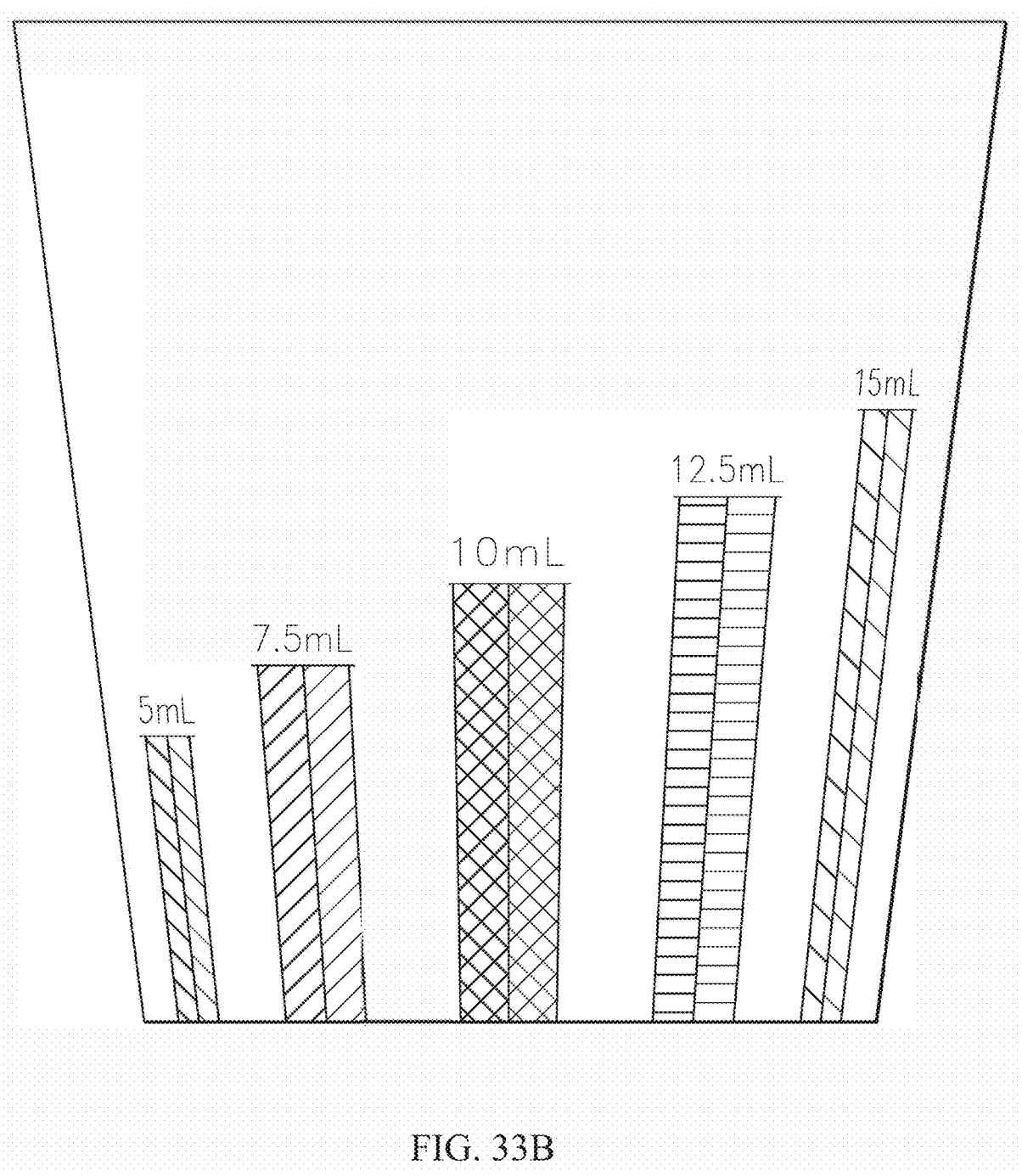
FIG. 33B shows a front elevation view of the medicine dispensing device of FIG. 33A.
Figure 33C:
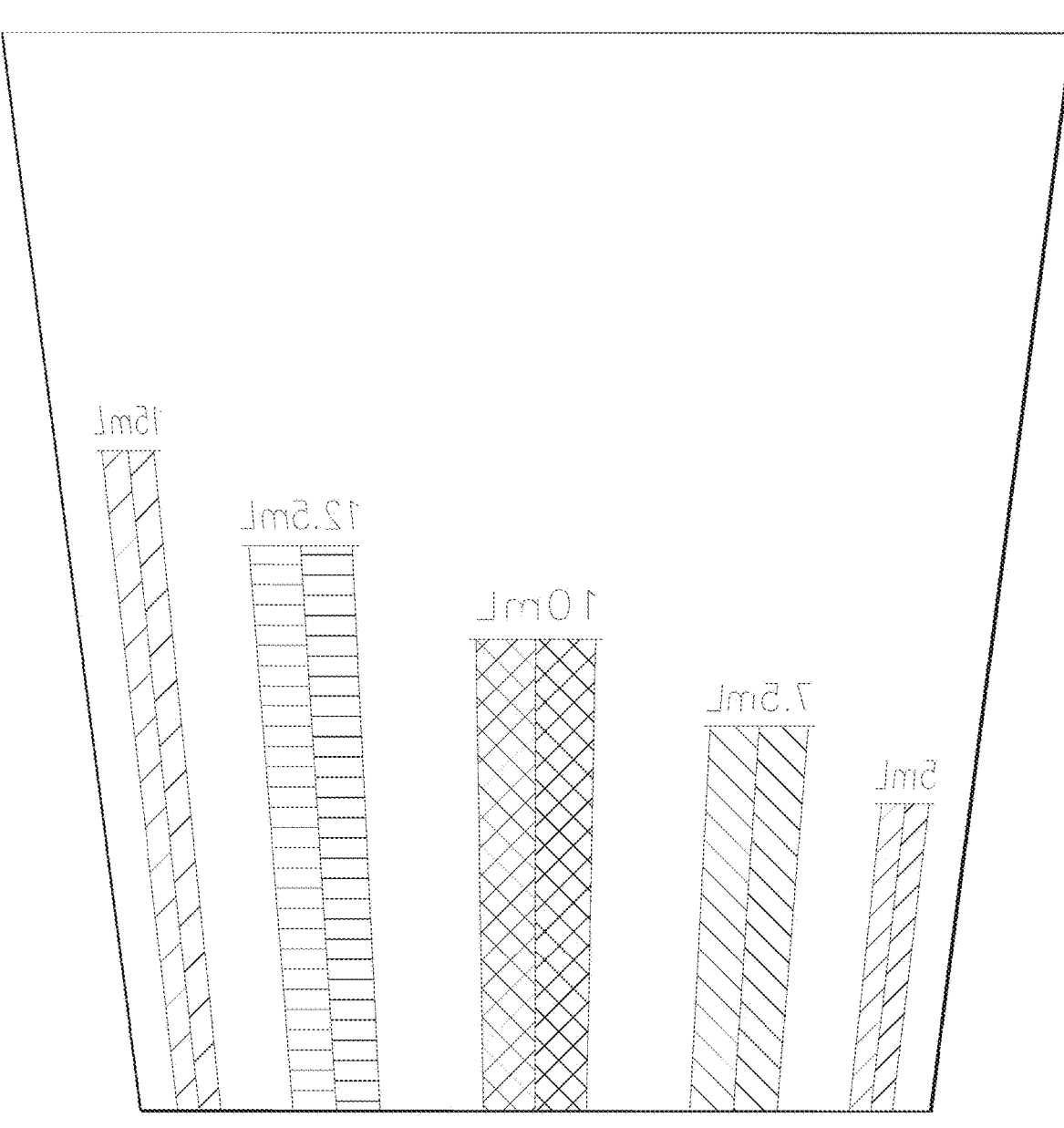
FIG. 33C shows a rear elevation view of the medicine dispensing device of FIG. 33A.
Figure 33D:
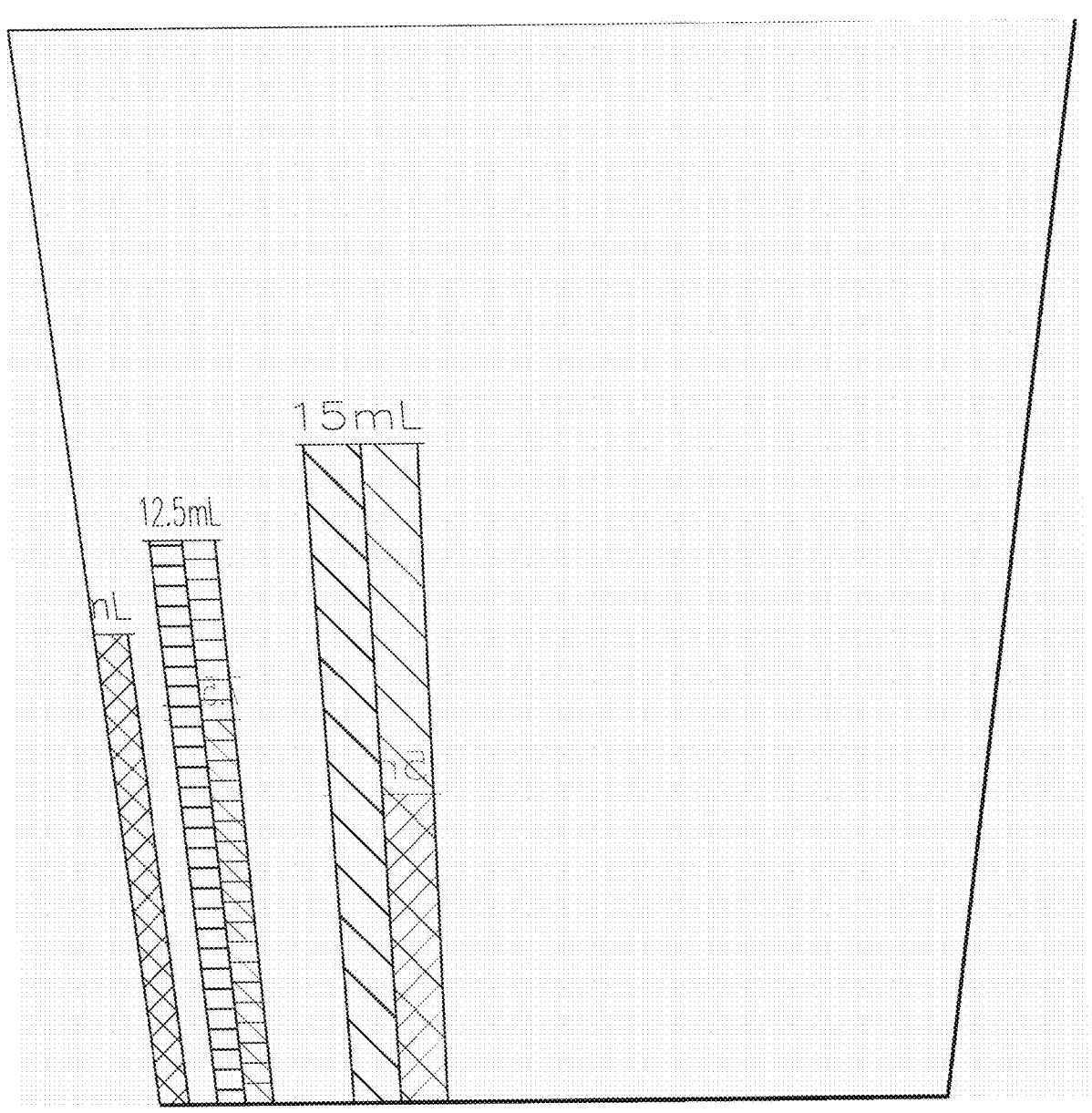
FIG. 33D shows a right-side view of the medicine dispensing device of FIG. 33A.
Figure 33E:
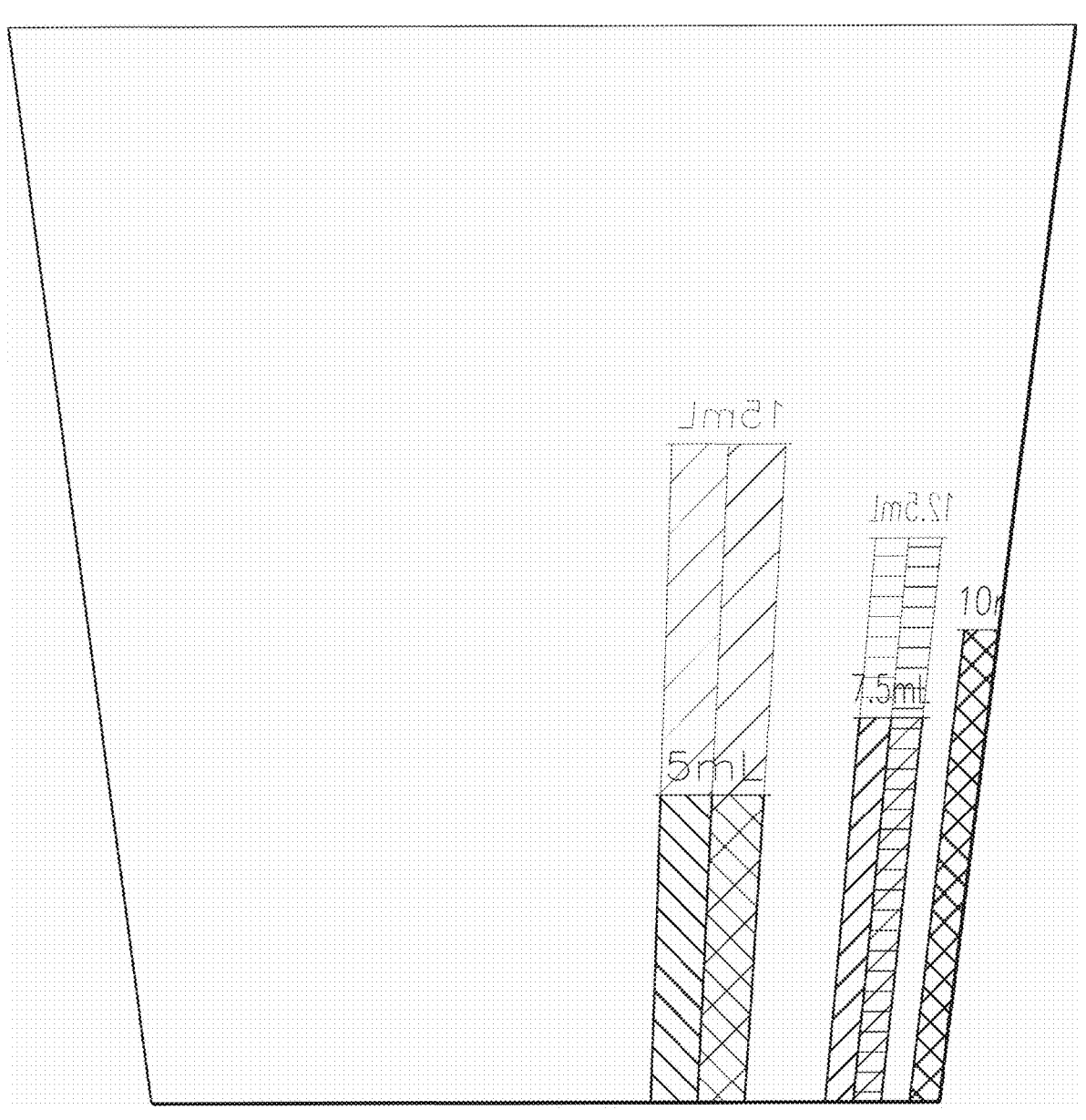
FIG. 33E shows a left side view of the medicine dispensing device of FIG. 33A.
Figure 33F:
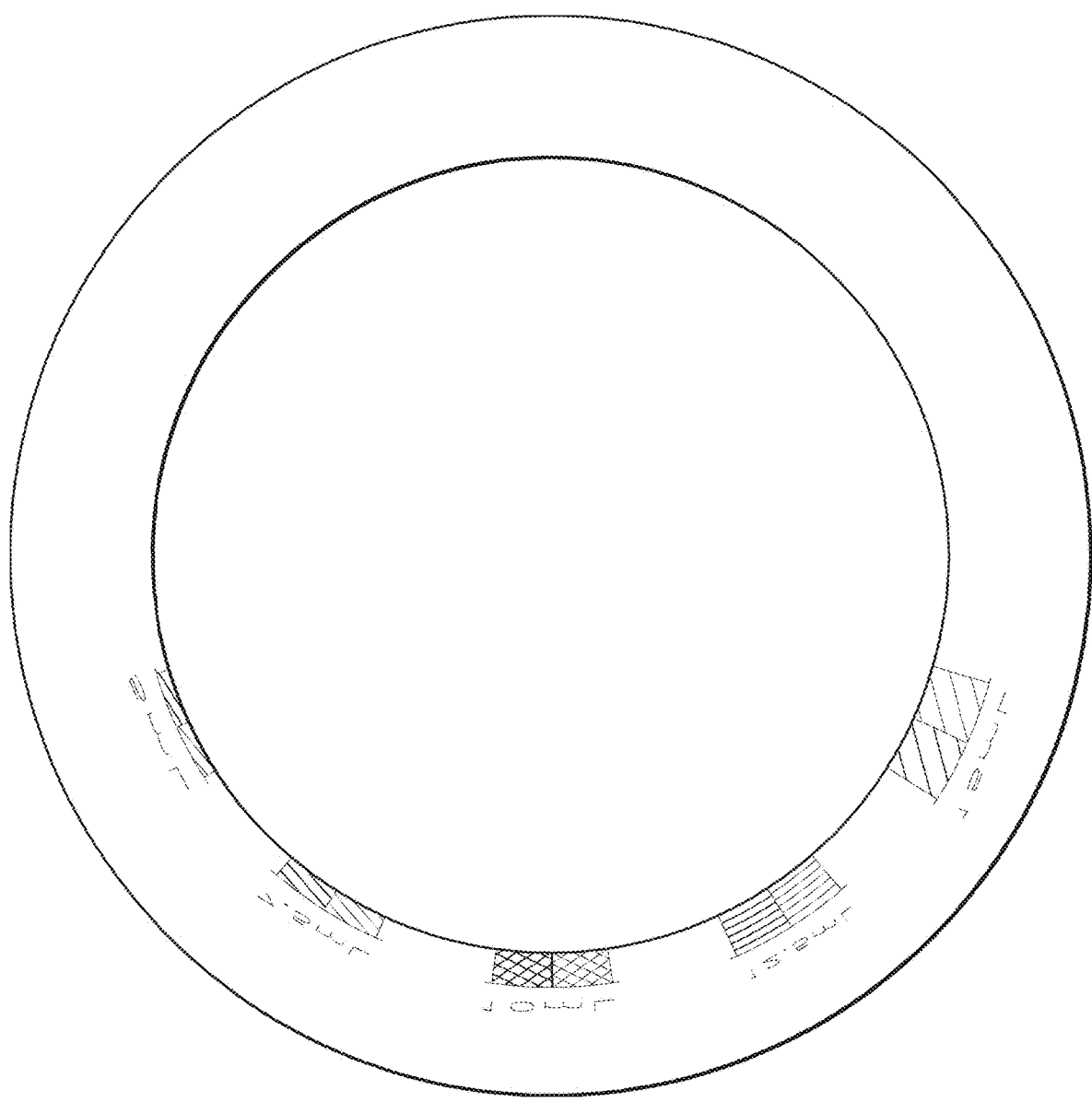
FIG. 33F shows a top view of the medicine dispensing device of FIG. 33A.
Figure 33G:
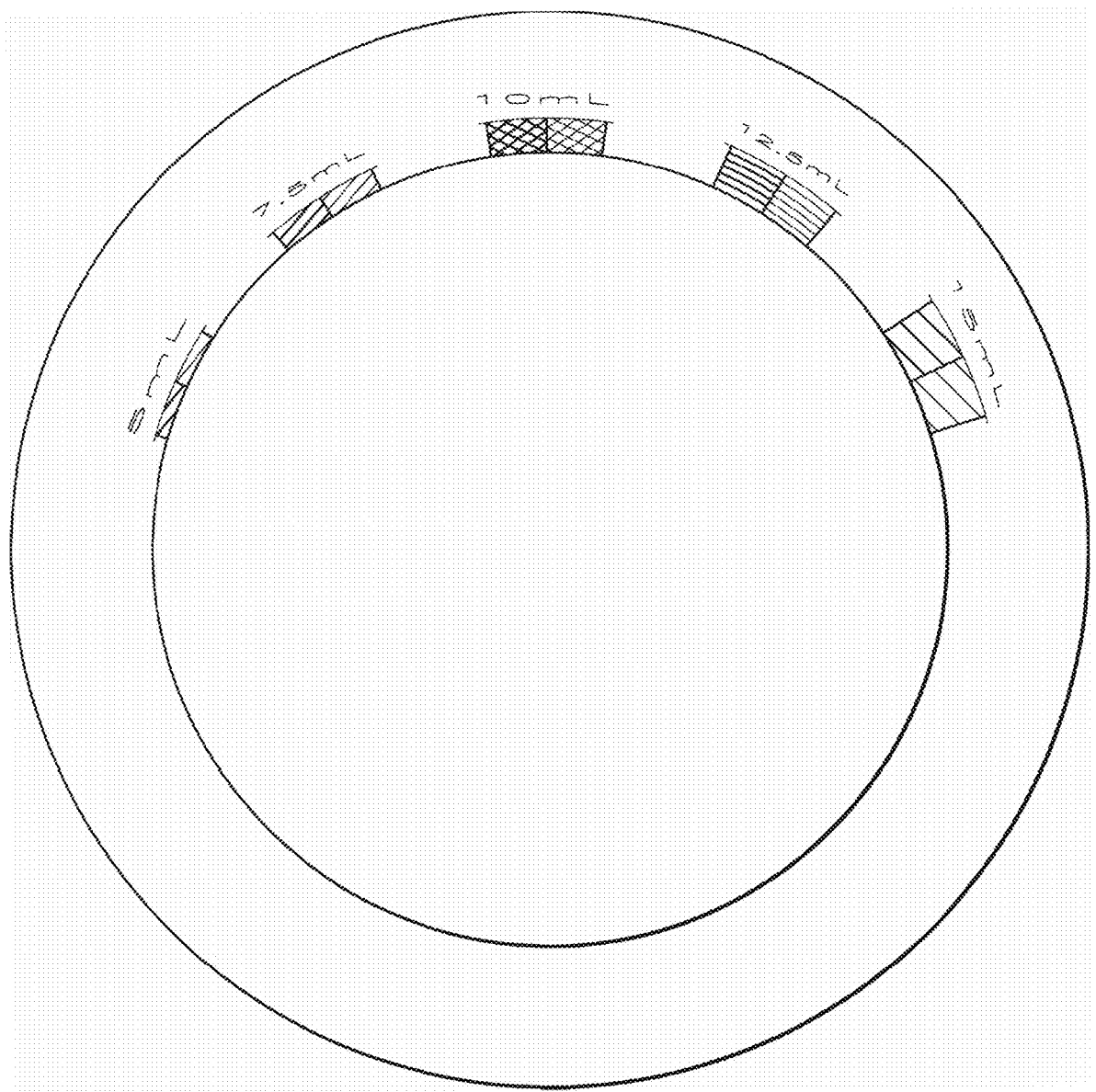
FIG. 33G shows a bottom view of the medicine dispensing device of FIG. 33A.

FIG. 33B is a front side view of the medicine dispensing device 3300; FIG. 33C is a rear elevation view of the medicine dispensing device 3300; FIG. 33D is a right side view of the medicine dispensing device 3300; FIG. 33E is a left side view of the medicine dispensing device 3300; FIG. 33F is a top view of the medicine dispensing device 3300; FIG. 33G is a bottom view of the medicine dispensing device 3300.

In the embodiments shown in FIGS. 33A-33G, there are five sets of stair-step dosing indicia. In other embodiments there may be more or fewer, and they may be spaced further apart from each other or closer together.

In one implementation the plurality of dosing indicia 3320 present on the cup 3310 are correlated to a plurality of values of a physical characteristic of a patient. Any of the methods described throughout the present disclosure Each of the plurality of stair-step dosing indicia 3320 may be of a different color. In addition, each of the plurality of dosing indicia may include a first portion of a first transparency 3320' and a second portion of a second transparency 3320" different from the first transparency. The first portion of a first transparency 3320' may be opaque and comprise a first color, and the second portion of a second transparency 3320" may be translucent and be a lighter version of the first color. A first of the plurality of dosing indicia 3320 may be separated from a second of the plurality of dosing indicia by approximately 180 degrees on the surface of the side wall of the cup 3310, as shown, or alternatively may be spaced by 90 degrees, 270 degrees, 360 degrees, or any number of degrees between 0-360. In the implementation shown, the medicine dispensing device 3200 is frustoconical, but in other embodiments it may be a different shape, such as rectangular, conical, or cylindrical. Each of the plurality of dosing indicia 3320 may further include a volumetric indication 3330.

In the embodiment of the medicine dispensing device 3300 shown, the relatively more transparent portion 3320" of a given dosing indicia 3320 permits a user to view the fluid level of the liquid medicine within the cup 3310 in relation to a line at the top of the indicia 3320. Generally, any level of the liquid medicine below the line at the top of the relevant dosing indicia 3320 is acceptable from the perspective of preventing overdosing. The more opaque portion 3320' of a given dosing indicia 3320 helps keep color zones visible when the liquid medicine within the cup 3310 has a color that can confound the user (e.g. grape or cherry). In alternate embodiments each dosing indicia may have substantially transparent and substantially opaque portions (as illustrated in FIGS. 34A-34G), may have only opaque portions, or may have only transparent portions.

Figure 34A:
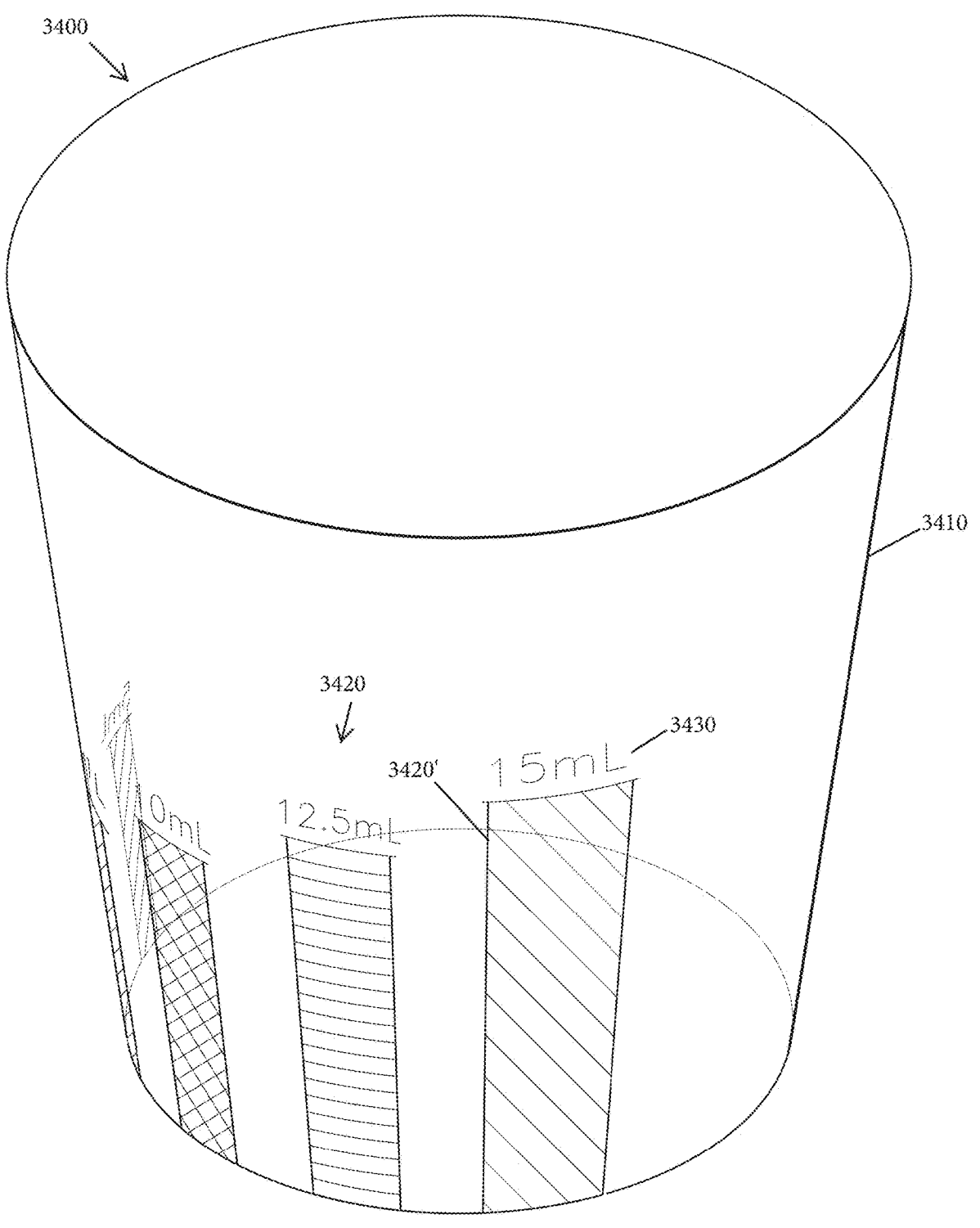
FIG. 34A shows a front perspective view of a medicine dispensing device of the present disclosure having a set of stair-step dosing indicia comprising different colors for each dose.

FIGS. 34A-34G illustrate a medicine dispensing device 3400 for administering a liquid medicine which utilizes an alternative set of stair-step dosing indicia 3420. As shown in a first front perspective view of the device 3400 illustrated in FIG. 34A, the device 3400 which includes a cup 3410 configured to contain a liquid medicine to be dispensed to a patient. The cup includes a side wall, a circular bottom element and an open top. As shown in FIG. 34A, the plurality of dosing indicia 3420 are spaced around a circumference of a surface of the side wall of the cup 3410. Each dosing indicia 3420 is of a different height relative to a reference level and corresponds to a different dose of the liquid medicine. In the embodiment shown, each stair-step dosing indicia is a different color. However, unlike the embodiment in FIGS. 33A-33G, there is no second corresponding portion having a different transparency.

Figure 34B:
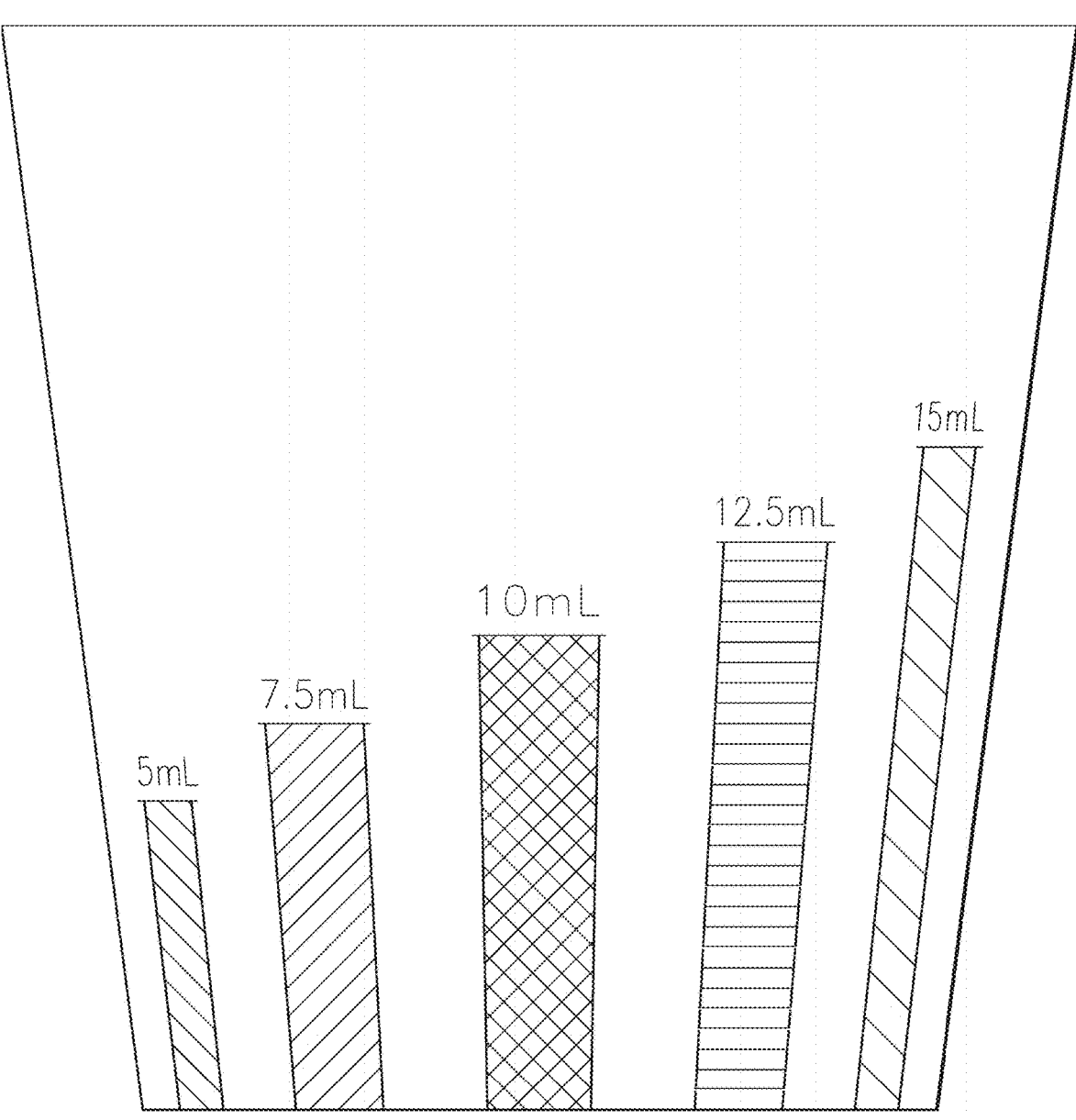
FIG. 34B shows a front elevation view of the medicine dispensing device of FIG. 34A.
Figure 34C:
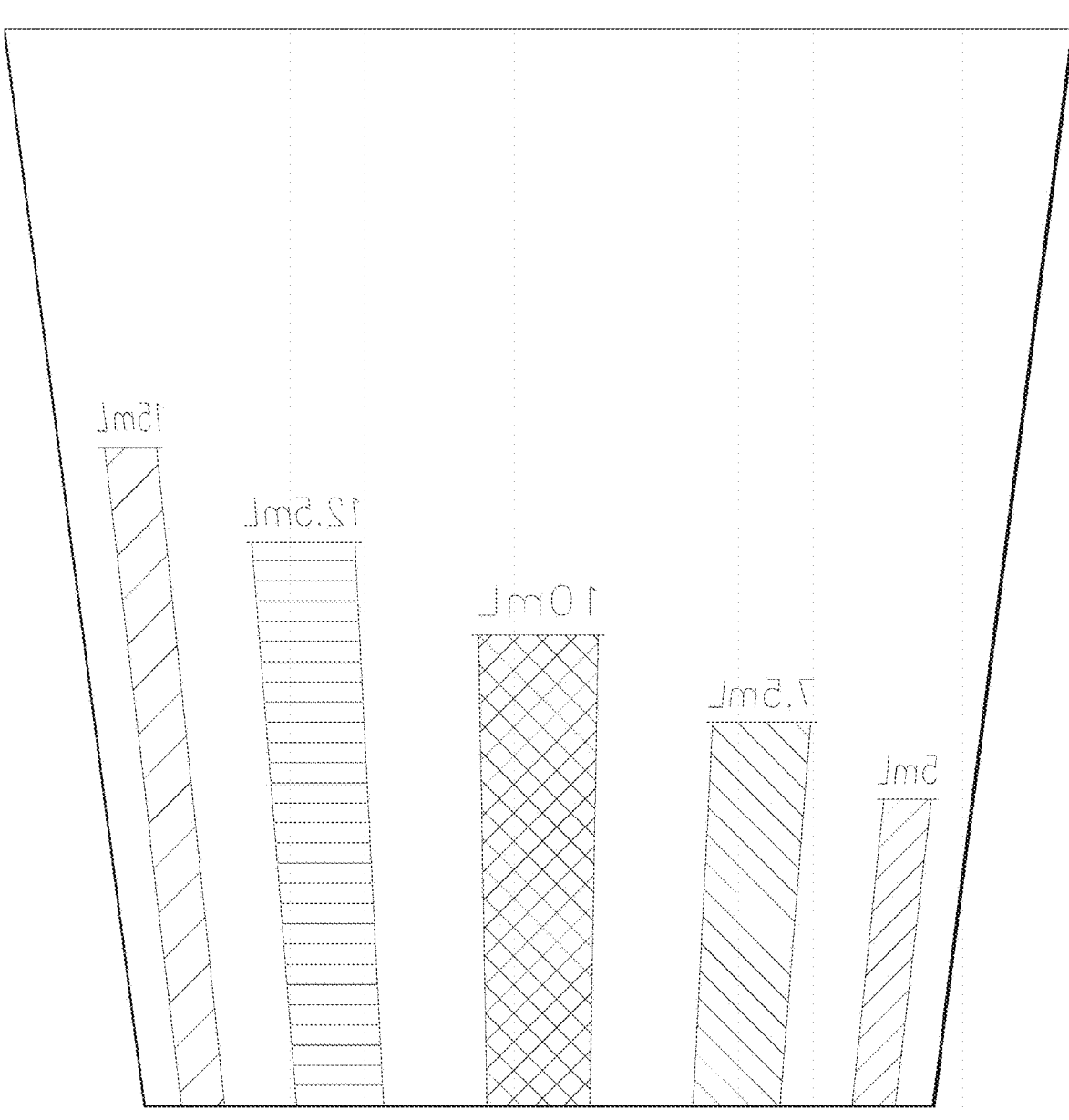
FIG. 34C shows a rear elevation view of the medicine dispensing device of FIG. 34A.
Figure 34D:
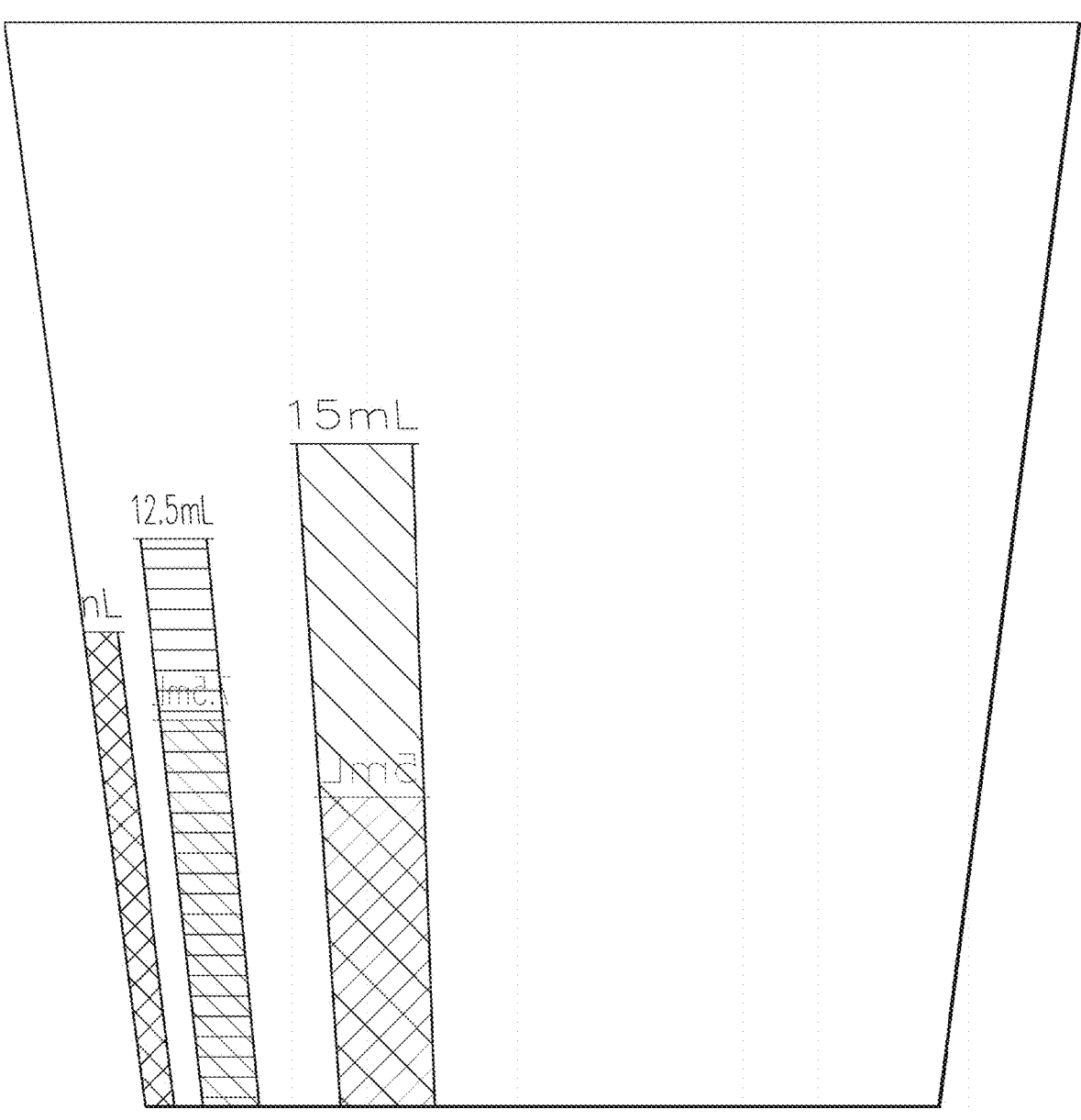
FIG. 34D shows a right-side view of the medicine dispensing device of FIG. 34A.
Figure 34E:
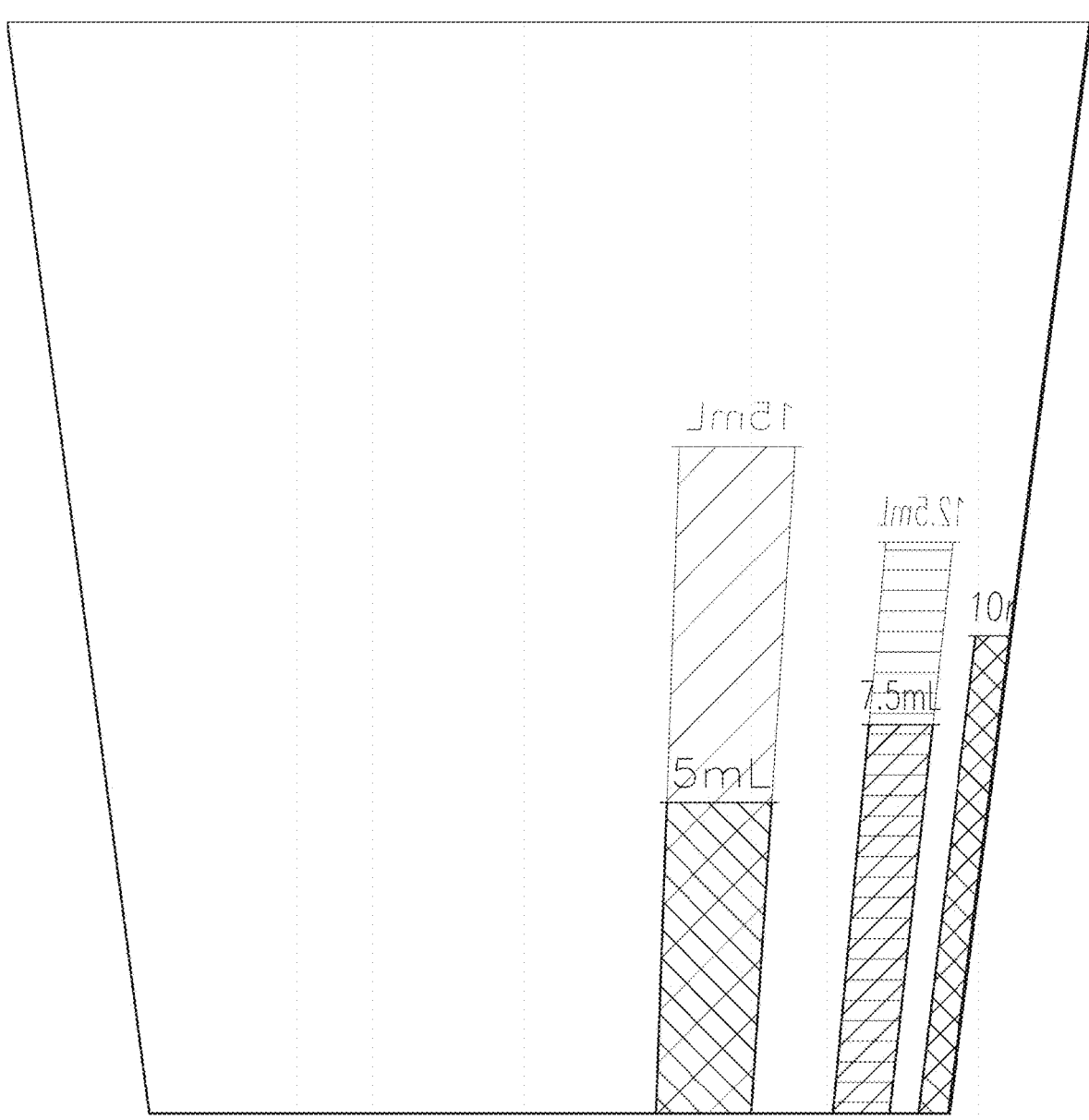
FIG. 34E shows a left side view of the medicine dispensing device of FIG. 34A.
Figure 34F:
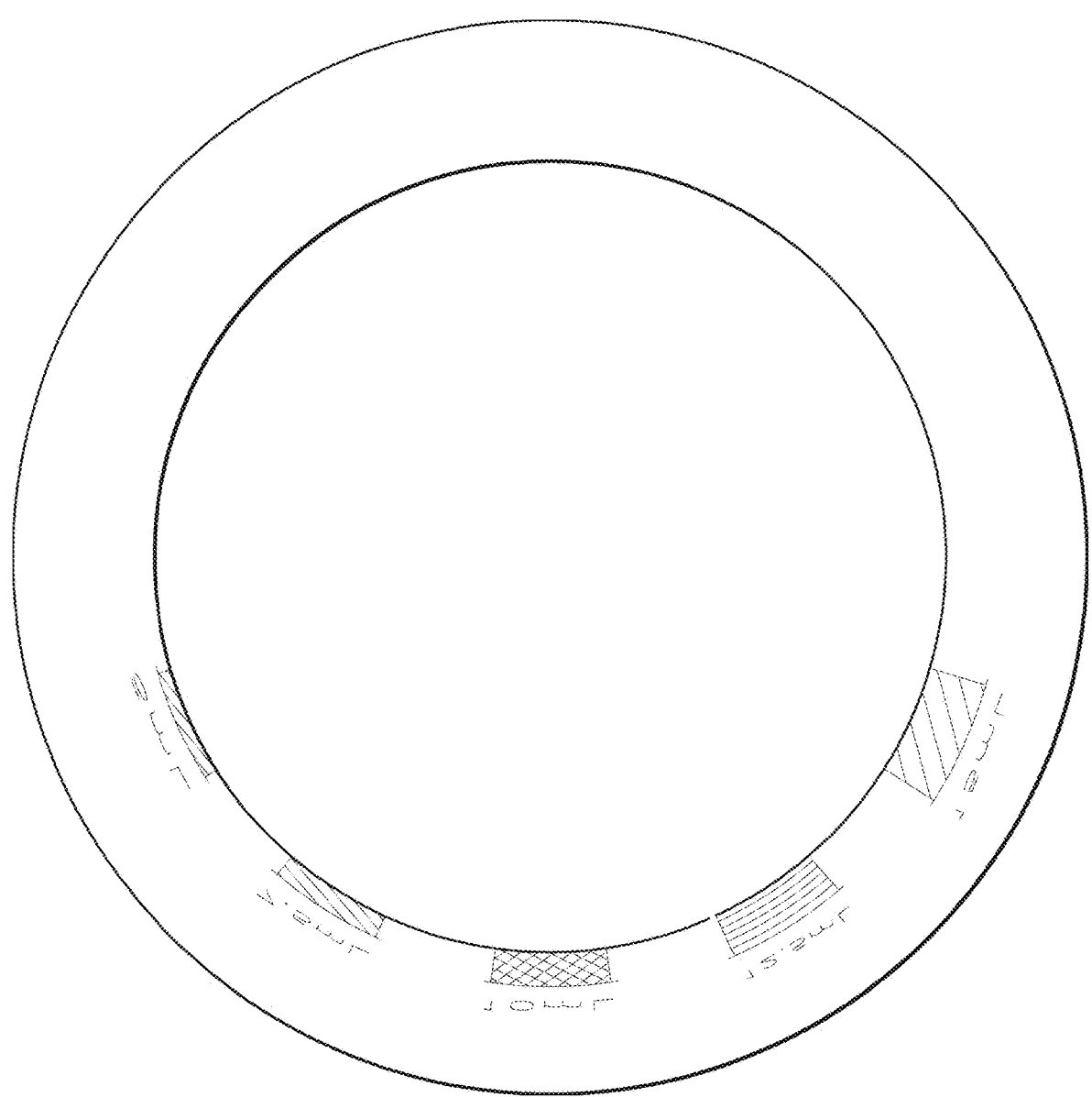
FIG. 34F shows a top view of the medicine dispensing device of FIG. 34A.
Figure 34G:
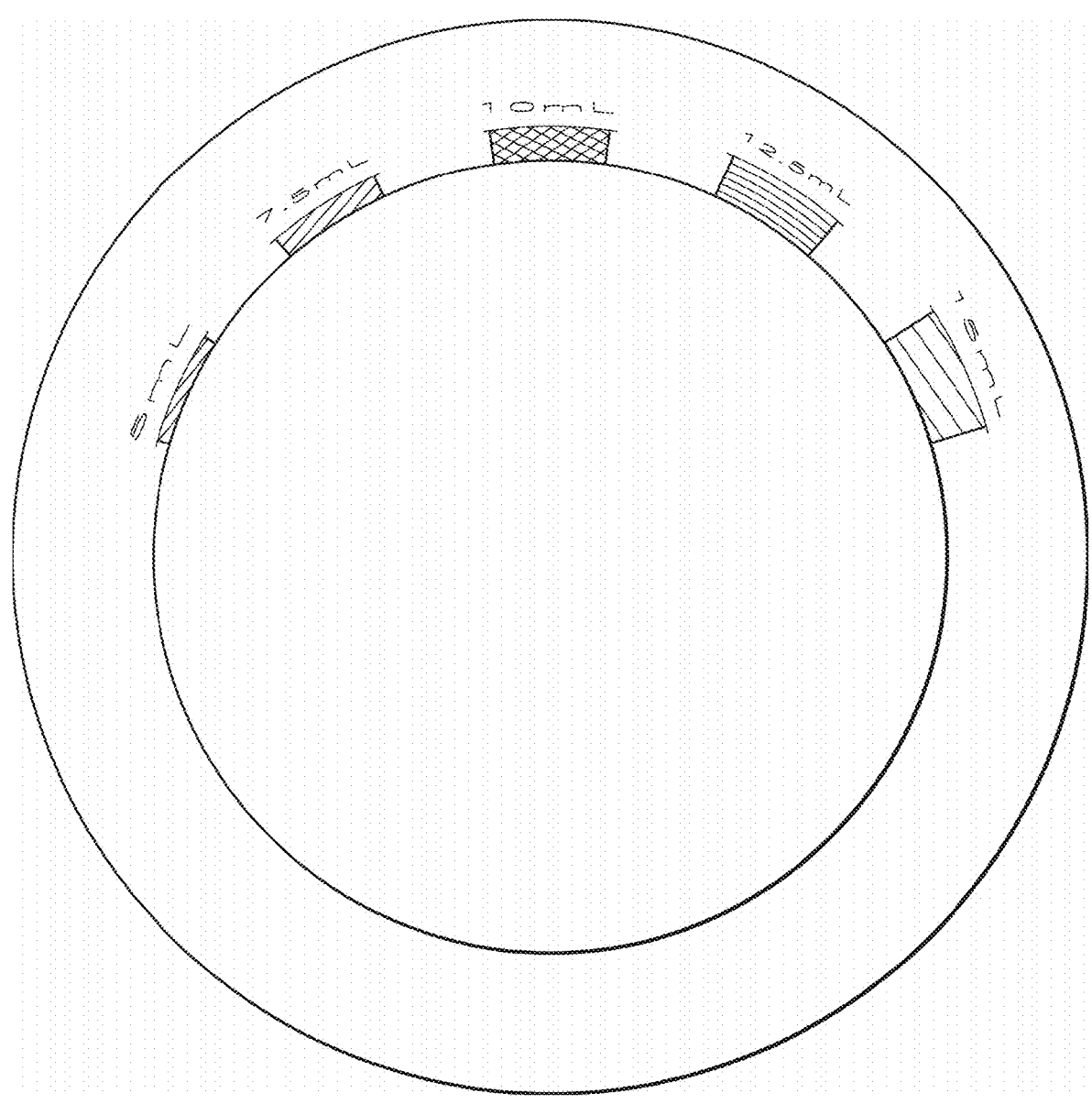
FIG. 34G shows a bottom view of the medicine dispensing device of FIG. 34A.

FIG. 34B is a front side view of the medicine dispensing device 3400; FIG. 34C is a rear elevation view of the medicine dispensing device 3400; FIG. 34D is a right side view of the medicine dispensing device 3400; FIG. 34E is a left side view of the medicine dispensing device 3400; FIG. 34F is a top view of the medicine dispensing device 3400; FIG. 34G is a bottom view of the medicine dispensing device 3400.

In one implementation the plurality of dosing indicia 3420 present on the cup 3410 are correlated to a plurality of values of a physical characteristic of a patient. Each of the plurality of dosing indicia 3420 may be of a different color. A first of the plurality of dosing indicia 3420 may be separated from a second of the plurality of dosing indicia by approximately 180 degrees on the surface of the side wall of the cup 3410, which in one implementation is frustoconical. Each of the plurality of dosing indicia 3420 may further include a volumetric indication 3430.

Example embodiments of the devices, systems and methods have been described herein. As may be noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices which may further include any and all elements/features from any other disclosed methods, systems, and devices, including any and all features corresponding to scientific data exchange. In other words, features from one and/or another disclosed embodiment may be interchangeable with features from other disclosed embodiments, which, in turn, correspond to yet other embodiments. Furthermore, one or more features/elements of disclosed embodiments may be removed and still result in patentable subject matter (and thus, resulting in yet more embodiments of the subject disclosure). Still further, some embodiments are distinguishable from the prior art due to such embodiments specifically lacking one or more features which are found in the prior art. In other words, claims to some embodiments of the disclosure may include one or more negative limitations to specifically note that the claimed embodiment lacks at least one structure, element, and/or feature that is disclosed in the prior art.

The invention claimed is:

1. A medicine dispensing device, comprising:
   a cup configured to contain a liquid medicine to be dispensed by the medicine dispensing device, the cup including a side wall, a circular bottom element and an open top; and a plurality of dosing indicia spaced apart from each other around and in relation to a circumference of a surface of the side wall, each dosing indicia of the plurality of dosing indicia being of a different height relative to a reference level and corresponding to a different dose of the liquid medicine;
   wherein each of the dosing indicia of the plurality of dosing indicia comprises a bar; and
   wherein each of the dosing indicia of the plurality of dosing indicia comprises a first portion of a first transparency and a second portion of a second transparency, wherein the first transparency is opaque and the second transparency is translucent.

2. The medicine dispensing device of claim 1 wherein the plurality of dosing indicia are correlated to a plurality of values of a physical characteristic of a patient.

3. The medicine dispensing device of claim 1 wherein each of the dosing indicia of the plurality of dosing indicia are of a different color.

4. The medicine dispensing device of claim 1 wherein the first portion of the first transparency and the second portion of the second transparency of each of the dosing indicia of the plurality of dosing indicia comprise a same color of a different shade.

5. The medicine dispensing device of claim 1 wherein a first dosing indicia of the plurality of dosing indicia is separated from a second dosing indicia of the plurality of dosing indicia by approximately 180 degrees on the surface of the side wall.

6. The medicine dispensing device of claim 1 wherein the side wall is frustoconical.

7. The medicine dispensing device of claim 1 wherein the reference level is proximate an upper surface of the circular bottom element.

8. The medicine dispensing device of claim 1 wherein each of the dosing indicia of the plurality of dosing indicia further comprises a volumetric indication.

9. A medicine dispensing device, comprising:
   a syringe having a barrel configured to contain a liquid medicine to be dispensed by the medicine dispensing device; and
   a plurality of color-coded dosing indicia spaced around and relative to a circumference of a surface of the barrel, each dosing indicia of the plurality of color-coded dosing indicia being of a different height relative to a reference level and corresponding to a different dose of the liquid medicine;
   wherein each of the dosing indicia of the plurality of color-coded dosing indicia are of a different color than each of the other dosing indicia of the plurality of color-coded dosing indicia; and
   wherein each of the dosing indicia of the plurality of color-coded dosing indicia comprises a first portion of a first transparency and a second portion of a second transparency, wherein the first transparency is opaque and the second transparency is translucent.

10. The medicine dispensing device of claim 9 wherein the plurality of color-coded dosing indicia are correlated to a plurality of values of a physical characteristic of a patient.

11. The medicine dispensing device of claim 9 wherein each of the dosing indicia of the plurality of color-coded dosing indicia comprises a bar.

12. The medicine dispensing device of claim 9 wherein the first portion of the first transparency and the second portion of the second transparency of each of the dosing indicia of the plurality of color-coded dosing indicia comprise a same color of a different shade.

13. The medicine dispensing device of claim 9 wherein a first dosing indicia of the plurality of color-coded dosing indicia is separated from a second dosing indicia of the plurality of color-coded dosing indicia by approximately 180 degrees on a surface of the barrel.

14. The medicine dispensing device of claim 9 wherein the reference level is proximate an end of the barrel.

15. A medicine dispensing device, comprising:

a spoon comprising a spoon head portion having a concave surface configured to receive and hold a liquid medicine to be dispensed by the medicine dispensing device; and a handle portion comprising a hollow barrel configured to hold a volume of the liquid medicine, the hollow barrel having a plurality of color-coded dosing indicia spaced about and relative to a circumference of the hollow barrel, each dosing indicia of the plurality of color-coded dosing indicia being of a different length relative to a reference and corresponding to a different dose of the liquid medicine; and wherein each of the dosing indicia of the plurality of color-coded dosing indicia comprises a first portion of a first transparency and a second portion of a second transparency, wherein the first transparency is opaque and the second transparency is translucent.

16. The medicine dispensing device of claim 15 wherein the plurality of color-coded dosing indicia are correlated to a plurality of values of a physical characteristic of a patient.

17. The medicine dispensing device of claim 15 wherein:

each of the dosing indicia of the plurality of color-coded dosing indicia are of a different color; and the first portion of the first transparency and the second portion of the second transparency of each of the dosing indicia of the plurality of color-coded dosing indicia comprise a same color of a different shade.

18. The medicine dispensing device of claim 15 wherein each of the dosing indicia of the plurality of color-coded dosing indicia further comprises a volumetric indication.

19. The medicine dispensing device of claim 15 wherein each of the dosing indicia of the plurality of color-coded dosing indicia comprises a bar.

20. The medicine dispensing device of claim 9 wherein each of the dosing indicia of the plurality of color-coded dosing indicia further comprises a volumetric indication.

* * * * *